United States Patent [19]

Liang

[11] Patent Number: 4,808,721

[45] Date of Patent: Feb. 28, 1989

[54] HERBICIDAL PYRIDINESULFONYLUREAS

[75] Inventor: Paul H. Liang, Wilmington, Del.

[73] Assignee: E. I. Du Pont de Nemours and Company, Wilmington, Del.

[21] Appl. No.: 90,889

[22] Filed: Aug. 28, 1987

Related U.S. Application Data

[63] Continuation-in-part of Ser. No. 39,491, Apr. 16, 1987, abandoned, which is a continuation-in-part of Ser. No. 939,428, Dec. 8, 1986, abandoned.

[51] Int. Cl.$^4$ .......................................... C07D 213/71
[52] U.S. Cl. .................................................... 546/293
[58] Field of Search ......................................... 546/293

[56] References Cited

U.S. PATENT DOCUMENTS

| | | | |
|---|---|---|---|
| 4,435,206 | 3/1984 | Levitt | 71/92 |
| 4,521,597 | 6/1985 | Kristensson | 544/3 |
| 4,522,645 | 6/1985 | Levitt | 71/93 |
| 4,549,898 | 10/1985 | Bohner | 71/90 |

*Primary Examiner*—John M. Ford

[57] ABSTRACT

This invention relates to herbicidal pyridinesulfonylureas which are highly active as preemergence and postemergence herbicides.

2 Claims, No Drawings

HERBICIDAL PYRIDINESULFONYLUREAS

RELATED APPLICATIONS

This application is a continuation in-part of my copending application, U.S. Ser. No. 039,491, filed Apr. 16, 1987 now abandoned, which is a continuation-in-part of my copending application, U.S. Ser. No. 939,428, filed Dec. 8, 1986, now abandoned.

BACKGROUND OF THE INVENTION

Pyridinesulfonylureas of the instant application show high activity as preemergence and postemergence herbicides. In particular, safety to corn is demonstrated by the herbicides.

EP-A-13,480 discloses herbicidal sulfonamides of the formula

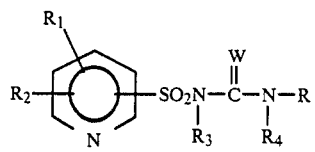

wherein $R_1$ is H, Cl, Br, F, $C_1$-$C_4$ alkyl, $C_1$-$C_4$ alkoxy, $C_1$-$C_4$ alkylthio, $NO_2$ or $CO_2R_5$.

U.S. Pat. No. 4,435,206, issued Mar. 6, 1984 and U.S. Pat. No. 4,522,645, issued June 11, 1985 disclose 2-pyridinesulfonylurea substituted in the 3-position by $R_1$, wherein $R_1$ is H, Cl, Br, F, $C_1$-$C_4$ alkyl, $C_1$-$C_4$ alkoxy, $C_1$-$C_4$ alkylthio, $NO_2$, $CF_3$, $CO_2R_5$ or $SO_2NR_6R_7$.

U.S. Pat. No. 4,339,267 discloses herbicidal sulfonamides of the formula

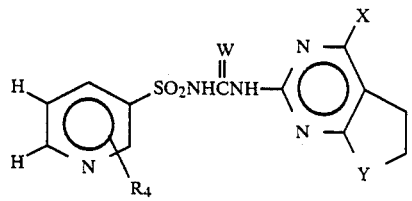

wherein $R_4$ is H, Cl, Br, F, $C_1$-$C_4$ alkyl, $C_1$-$C_4$ alkoxy, $NO_2$, $CO_2R_6$ or $SR_{13}$.

EP-A-30,433 discloses herbicidal sulfonamides of the formula

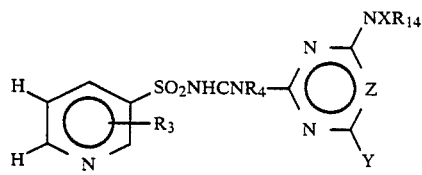

wherein
X is H;
$R_{14}$ is H or $CH_3$; and
$R_3$ is H, F, Cl, Br, $CH_3$, $OCH_3$, $NO_2$, $CO_2R_{11}$ or $S(O)_nR_{12}$.

U.S. Pat. No. 4,456,469 discloses herbicidal sulfonamides of the formula

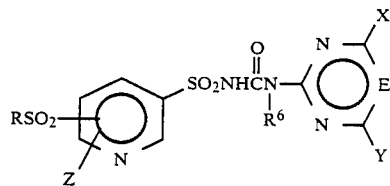

wherein
R is $C_1$-$C_6$ alkyl, $C_3$-$C_6$ alkenyl, $C_2$-$C_4$ alkoxyalkyl, $C_5$-$C_6$ cycloalkyl, R'OCH$_2$CH$_2$OCH$_2$, R'OCH$_2$CH$_2$OCH$_2$CH$_2$,

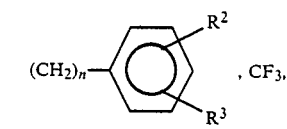

$CF_3CH_2$, HGLCCF$_2$ or HCF$_2$; and
Z is H, F, Cl, Br, $CH_3$, $OCH_3$ or $SCH_3$.

U.S. Pat. No. 4,487,626 discloses herbicidal sulfonamides of the formula

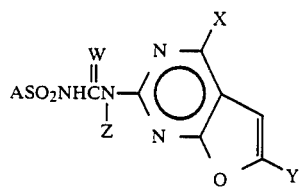

wherein
A is

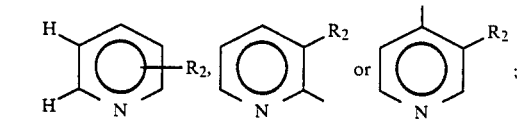

and
$R_2$ is H, F, Cl, Br, $C_1$-$C_4$ alkyl, $C_1$-$C_4$ alkoxy, $NO_2$, $CO_2R_{15}$, $S(O)_mR_{16}$, $SO_2NR_{18}R_{19}$ or $SO_2N(OCH_3)CH_3$.

U.S. Pat. No. 4,421,550 discloses herbicidal sulfonamides of the formula

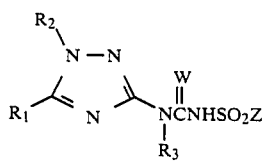

wherein
Z is

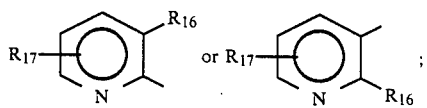

and $R_{16}$ is H, $C_1$-$C_4$ alkyl, $C_1$-$C_4$ alkoxy, F, Cl, Br, $CF_3$, $CO_2R_{20}$, $SO_2NR_{10}R_{11}$, $SO_2N(OCH_3)CH_3$ or $S(O)_nR_{13}$.

U.S. Pat. No. 4,496,392 discloses herbicidal sulfonamides of the formula

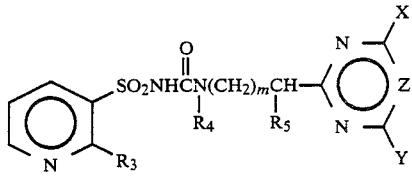

wherein $R_3$ is Cl, $SO_2CH_3$ or $SO_2N(CH_3)_2$.

EP-A-84,224 discloses herbicidal sulfonamides of the formula

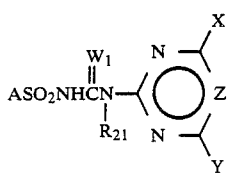

wherein
A is

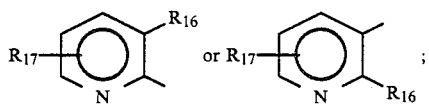

and
$R_{16}$ is H, $C_1$-$C_4$ alkyl, $C_1$-$C_4$ alkoxy, F, Cl, Br, $CF_3$, $CO_2R_9$, $SO_2NR_{10}R_{11}$, $SO_2N(OCH_3)CH_3$ or $S(O)_nR_{13}$.

EP-A-125,846 discloses herbicidal sulfonamides of the formula

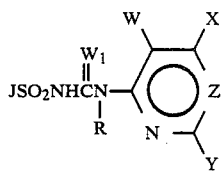

wherein
J is

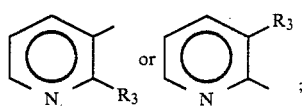

and
$R_3$ is Cl, $SO_2CH_3$, $SO_2N(CH_3)_2$, $OCH_3$, $NO_2$ or $N(CH_3)_2$.

EP-A-155,767 discloses herbicidal sulfonamides of the formula

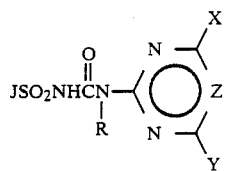

wherein
J is

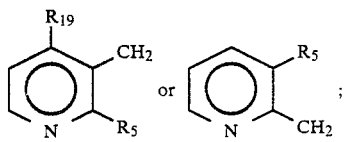

and
$R_5$ is H, $CH_3$, Cl, Br, $CO_2R_{15}$, $C(O)NR_{16}R_{17}$, $SO_2NR_{16}R_{17}$, $SO_2N(OCH_3)CH_3$, $SO_2R_{18}$ or $NO_2$.

EP-A-161,905 discloses herbicidal sulfonamides of the formula

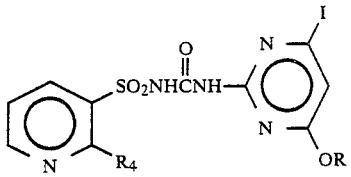

wherein $R_4$ is $CH_3$, $CH_2CH_3$, $OCH_3$, $OCH_2CH_3$, F, Cl, Br, $SO_2NR_{16}R_{17}$, $SO_2N(OCH_3)CH_3$, $S(O)_nR_{19}$, $C_3$-$C_4$ alkenyloxy or $C_3$-$C_4$ alkynyloxy.

EP-A-164,269 discloses herbicidal sulfonamides of the formula

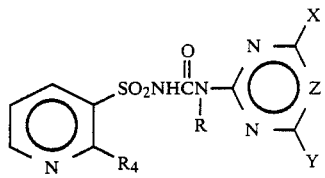

wherein $R_4$ is $CH_3$, $CH_2CH_3$, $OCH_3$, $OCH_2CH_3$, F, Cl, Br, $SO_2NR_{11}R_{12}$, $SO_2N(OCH_3)CH_3$ or $S(O)_nR_{13}$.

EP-A-171,286 discloses herbicidal sulfonamides of the formula

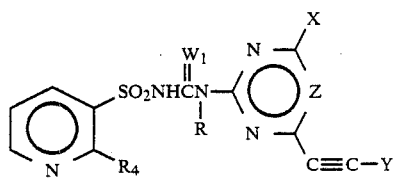

wherein $R_4$ is $CH_3$, $CH_2CH_3$, $OCH_3$, $OCH_2CH_3$, F, Cl, Br, $SO_2NR_{18}R_{19}$, $SO_2N(OCH_3)CH_3$, $S(O)_nR_{21}$, $C_3$-$C_4$ alkenyloxy, $CH_2OCH_3$ or $CH_2OCH_2CH_3$.

South African Patent Application No. 83/4305, published Dec. 14, 1983, discloses herbicidal sulfonamides of the formula

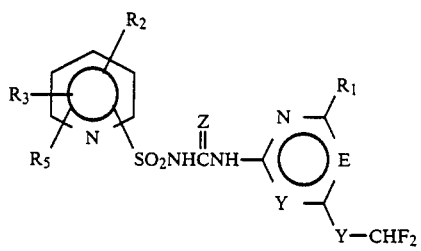

wherein
R$_2$ is H, C$_1$-C$_3$ alkyl, C$_1$-C$_3$ haloalkyl, halogen, NO$_2$, C$_1$-C$_3$ alkoxy, C(W)R$_8$, SO$_2$NR$_6$R$_7$, S(O)$_n$C$_1$-C$_3$ alkyl or C(O)R$_9$;
R$_3$ is H, halogen, C$_1$-C$_3$ alkyl, OCH$_3$, NO$_2$ or CF$_3$;
R$_5$ is H, NO$_2$, F, Cl, Br, CH$_3$, CF$_3$, S(O)$_n$C$_1$-$_{C3}$ alkyl, C(O)C$_1$-C$_4$ alkoxy or C$_1$-C$_3$ alkoxy;
Y is O or S.

South African Patent Application No. 83/6639, published Mar. 8, 1984, discloses herbicidal sulfonamides of the formula

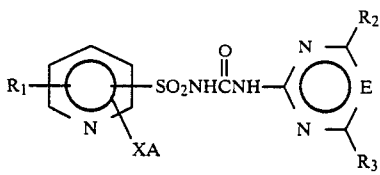

wherein
A is a C$_3$-C$_6$ alkynyl radical, a C$_1$-C$_6$ alkyl radical which is substituted by halogen, C$_1$-C$_4$ alkoxy, C$_1$-C$_4$ alkylthio, C$_1$-C$_4$ alkylsulfinyl, C$_1$-C$_4$ alkylsulfonyl, C$_1$-C$_4$ haloalkoxy, C$_1$-C$_4$ haloalkylthio, C$_1$-C$_4$ haloalkylsulfinyl or C$_1$-C$_4$ haloalkylsulfonyl, or is a C$_2$-C$_4$ alkenyl radical which is unsubstituted or substituted as for C$_1$-C$_6$ alkyl, or is a phenyl radical which is unsubstituted or substituted by halogen, cyano, nitro, C$_1$-C$_4$ alkyl, C$_1$-C$_4$ haloalkyl, an -X-C$_1$-C$_4$ alkyl, C$_1$-C$_4$ alkoxycarbonyl, amino, mono- or di(C$_1$-C$_4$ alkyl)amino, carbamoyl, mono- or di-(C$_1$-C$_4$ alkyl)carbamoyl, sulfamoyl, mono- or di-(C$_1$-C$_4$ alkyl)sulfamoyl radical;
R$_1$ is hydrogen, halogen, C$_1$-C$_4$ alkyl, C$_1$-C$_4$ alkoxy, C$_1$-C$_4$ haloalkyl, C$_1$-C$_4$ haloalkoxy, C$_2$-C$_5$ alkoxyalkoxy, C$_1$-C$_5$ alkylthio, C$_1$-C$_5$ alkylsulfinyl or C$_1$-C$_5$ alkylsulfonyl; and
X is O, S, SO or SO$_2$.

U.S. Pat. No. 4,518,776 discloses a process for the preparation of herbicidal sulfonamides of the formula

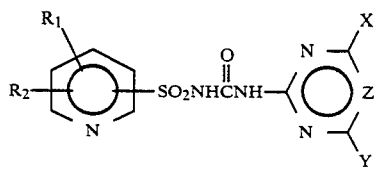

wherein
R$_1$ is S(O)$_n$C$_1$-C$_4$ alkyl or SO$_2$di-C$_1$-C$_4$ alkylamino; and
R$_2$ is H, halogen, CF$_3$, NO$_2$, C$_1$-C$_4$ alkyl or C$_1$-C$_4$ alkoxy.

This patent generically discloses, but does not claim, compounds of the instant invention.

EP-A-101,670, published Feb. 29, 1984, discloses a process for the preparation of herbicidal sulfonamides of the formula

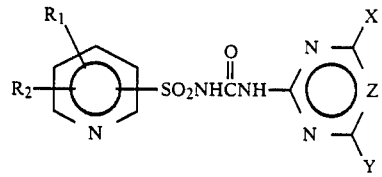

wherein
R$_1$ is Q-C$_1$-C$_4$ alkyl or SO$_2$-di-C$_1$-C$_4$ alkylamino;
Q is S or S(O)$_n$; and
R$_2$ is H, halogen, CF$_3$, NO$_2$, C$_1$-C$_4$ alkyl or C$_1$-C$_4$ alkoxy.

This application generically discloses compounds of the instant invention.

U.S. Pat. No. 4,521,597 discloses a process for the preparation of herbicidal sulfonamides of the formula

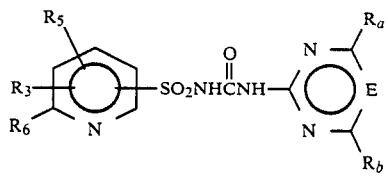

wherein
R$_3$ is H, F, Cl, Br, NO$_2$, OCH$_3$ or CF$_3$;
R$_5$ is S(O)$_m$C$_1$-C$_5$ alkyl or SO$_2$NR$_8$R$_9$; and
R$_6$ is H, F, CH$_3$ or OCH$_3$.

This patent generically discloses, but does not claim, compounds of the instant invention.

EP-A-184,385, published June 11, 1986, discloses the following compound for selective weed control in tomatoes and turf.

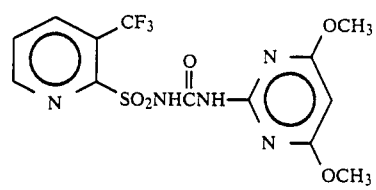

U.S. Ser. No. 874,307 discloses herbicidal o-alkylcarbonyl-pyridinesulfonylureas.
U.S. Ser. No. 943,137 discloses herbicidal o-substituted-pyridinesulfonylureas.

SUMMARY OF THE INVENTION

This application pertains to novel compounds of Formula I, agriculturally suitable compositions containing them and their method-of-use as preemergent and/or postemergent herbicides or plant growth regulants.

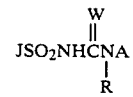

wherein
J is

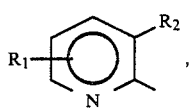 J-1

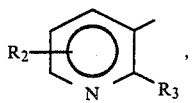 J-2

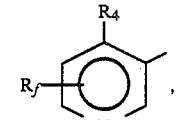 J-3

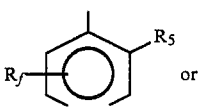 J-4 or

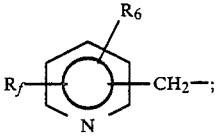 J-5

R is H or $CH_3$;
W is O or S;
$R_1$ is $R_f$ or $R_g$;
$R_f$ is H, $C_1-C_3$ alkyl, $C_1-C_3$ haloalkyl, halogen, $NO_2$, $C_1-C_3$ alkoxy, $C_1-C_3$ alkylthio or CN;
$R_g$ is $C_2-C_3$ alkyl, $C_1-C_3$ haloalkyl, cyclopropyl, $C_1-C_3$ alkyl substituted by $C_1-C_3$ alkoxy, OH, $C_1-C_2$ alkylthio or CN, $W_2R_{11}$, amino, $C_1-C_3$ alkylamino or $C_1-C_3$ dialkylamino;
$R_2$ is $SO_2NH_2$, $SO_2NR_dR_e$, $SO_2NR_7R_8$, $SO_2NR_7'R_8$, $CO_2R_9$ or $CO_2R_9'$;
$R_3$ is $SO_2NH_2$, $SO_2NR_dR_e$, $SO_2NR_7R_8$, $SO_2NR_7'R_8$; $CO_2R_9$ or $CO_2R_9'$;
$R_4$ is $SO_2NH_2$, $SO_2NR_dR_e$, $SO_2NR_7R_8$ or $CO_2R_9$;
$R_5$ is $SO_2NH_2$, $SO_2NR_dR_e$, $SO_2NR_7R_8$ or $CO_2R_9$;
$R_6$ is $SO_2NR_dR_e$, $SO_2NR_7R_8$ or $CO_2R_9$;
$R_7$ is H, $C_2-C_3$ cyanoalkyl, $C_3-C_4$ alkenyl or $C_3-C_4$ alkynyl;
$R_7'$ is $C_1-C_4$ alkyl;
$R_8$ is $C_1-C_4$ alkyl, $C_1-C_4$ haloalkyl, $C_3-C_4$ alkenyl, $C_3-C_4$ alkynyl, $C_2-C_4$ alkoxyalkyl or cyclopropyl; or
$R_7$ and $R_8$ may be taken together as $-(CH_2)_3-$, $-(CH_2)_4-$, $-(CH_2)_5-$ or $-CH_2CH_2OCH_2CH_2-$;
$R_9$ is $CH_2CH_2R_{10}$, $CH_2CF_3$, $C_3-C_4$ haloalkyl, $C_3-C_4$ alkynyl, $C_2-C_4$ alkylthioalkyl, $C_3-C_5$ cycloalkyl or $C_4-C_7$ cycloalkylalkyl;
$R_9'$ is $C_1-C_4$ alkyl, $C_3-C_4$ alkenyl, $CH_2CH_2Cl$, $CH_2CH_2Br$, $CH_2CH_2OCH_3$ or $CH_2CH_2OC_2H_5$;
$R_{10}$ is OH, F, CN, $OSO_2(C_1-C_3$ alkyl) or $OSO_2(C_1-C_3$ haloalkyl);
$R_{11}$ is $C_1-C_3$ alkyl, $C_1-C_3$ haloalkyl, $C_3-C_4$ alkenyl or $C_3-C_4$ alkynyl;
$W_2$ is O or S;
A is

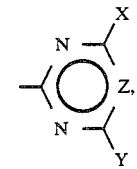 A-1

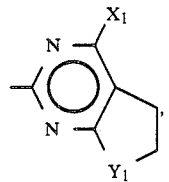 A-2

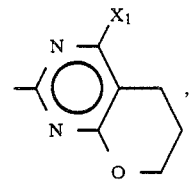 A-3

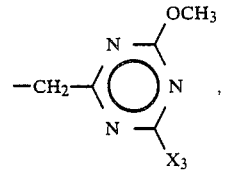 A-4

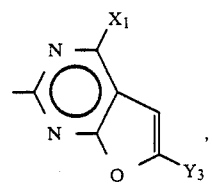 A-5

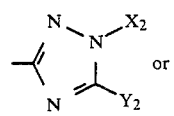 A-6 or

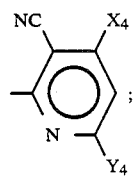 A-7

X is H, $C_1-C_4$ alkyl, $C_1-C_4$ alkoxy, $C_2-C_4$ haloalkoxy, $C_1-C_4$ haloalkyl, $C_2-C_4$ haloalkylthio, $C_1-C_4$ alkylthio, halogen, $C_2-C_5$ alkoxyalkyl, $C_2-C_5$ alkoxyalkoxy, amino, $C_1-C_3$ alkylamino or di($C_1-C_3$ alkyl)amino;

Y is H, $C_1-C_4$ alkyl, $C_1-C_4$ alkoxy, $C_2-C_4$ haloalkoxy, $C_2-C_4$ haloalkylthio, $C_1-C_4$ alkylthio, $C_2-C_5$ alkoxyalkyl, $C_2-C_5$ alkoxyalkoxy, amino, $C_1-C_3$ alkylamino, di($C_1-C_3$ alkyl)amino, $C_3-C_4$ alkenyloxy, $C_3-C_4$ alkynyloxy, $C_2-C_5$ alkylthioalkyl, $C_2-C_5$ alkylsulfinylalkyl, $C_2-C_5$ alkylsulfonylalkyl, $C_1-C_4$ haloalkyl, $C_2-C_4$ alkynyl, $C_3-C_5$ cycloalkyl, azido,

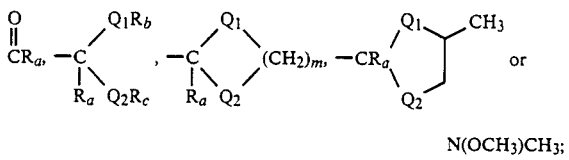

m is 2 or 3;
$Q_1$ and $Q_2$ are independently O or S;
$R_a$ is H or $C_1$-$C_3$ alkyl;
$R_b$ and $R_c$ are independently $C_1$-$C_3$ alkyl;
$R_d$ is H or $C_1$-$C_2$ alkyl;
$R_e$ is $C_1$-$C_2$ alkoxy;
Z is CH, N, $CCH_3$, $CC_2H_5$, CCl or CBr;
$Y_1$ is O or $CH_2$;
$X_1$ is $CH_3$, $OCH_3$, $OC_2H_5$ or $OCF_2H$;
$X_2$ is $CH_3$, $C_2H_5$ or $CH_2CF_3$;
$Y_2$ is $OCH_3$, $OC_2H_5$, $SCH_3$, $SC_2H_5$, $CH_3$ or $CH_2CH_3$;
$X_3$ is $CH_3$ or $OCH_3$;
$Y_3$ is H or $CH_3$;
$X_4$ is $CH_3$, $OCH_3$, $OC_2H_5$, $CH_2OCH_3$ or Cl;
$Y_4$ is $CH_3$, $OCH_3$, $OC_2H_5$ or Cl;
and their agriculturally suitable salts; provided that
(1) when X is halogen, then Z is CH and Y is $OCH_3$, $OC_2H_5$, $NH_2$, $NHCH_3$, $N(CH_3)_2$ or $N(OCH_3)CH_3$;
(2) when W is S, then R is H, A is A-1, Z is CH or N, and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or

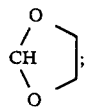

(3) when the total number of carbon atoms of X and Y is greater than four, then the combined number of carbons of $R_1$, $R_2$, $R_3$, $R_4$, $R_5$ or $R_6$ is less than or equal to six;
(4) when J is J-1 and $R_2$ is $SO_2NR_7'R_8$, $SO_2NR_dR_e$ or $CO_2R_9'$, or when J is $J_2$ and $R_3$ is $SO_2NR_dR_e$, $SO_2NR_7'R_8$ or $CO_2R_9'$, then Y is other than $C_2$-$C_5$ alkylthioalkyl, $C_2$-$C_5$ alkylsulfinylalkyl, $C_2$-$C_5$ alkylsulfonylalkyl,

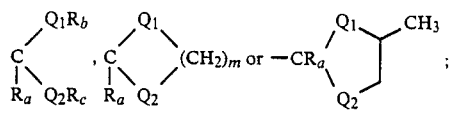

(5) when J is J-2 and $R_3$ is $SO_2NR_dR_e$ or $R_7$ is H, then X and Y are other than $C_2$-$C_4$ haloalkoxy;
(6) when J is J-5, then $R_7$ is other than H or $R_6$ is other than $SO_2NR_dR_e$;
(7) when J is $J_2$ and $R_3$ is $SO_2NH_2$ or $SO_2NR_dR_e$, or $R_7$ is H, then X is other than iodine; and
(8) when J is J-2 and $R_7$ is H or $R_3$ is $SO_2NR_dR_e$, then Y is other than $C_2$-$C_4$ alkynyl;
(9) $X_4$ and $Y_4$ are not simultaneously Cl;
(10) when J is J-1, J-2, J-3, J-4 and A is A-5, then $R_f$ is other than H;
(11) when J is J-1 or J-2, then A is other than A-6; and
(12) when $R_2$ or $R_3$ is $CO_2R_9'$ or $SO_2NR_7'R_8$, then $R_1$ is $R_g$ and when $R_2$ or $R_3$ is other than $CO_2R_9'$ or $SO_2NR_7'R_8$, then $R_1$ is $R_f$.

In the above definitions, the term "alkyl", used either alone or in compound words such as "alkylthio" or "haloalkyl", denotes straight chain or branched alkyl, e.g. methyl, ethyl, n-propyl, isopropyl or the different butyl isomers.

Alkoxy denotes methoxy, ethoxy, n-propyloxy or isopropyloxy.

Alkenyl denotes straight chain or branched alkenes, e.g. 1-propenyl, 2-propenyl, 3-propenyl and the different butenyl isomers.

Alkynyl denotes straight chain or branched alkynes, e.g. ethynyl, 1-propynyl, 2-propynyl and the different butynyl isomers.

Alkylsulfonyl denotes methylsulfonyl, ethylsulfonyl and the different propylsulfonyl and butylsulfonyl isomers.

Cycloalkyl denotes cyclopropyl, cyclobutyl and cyclopentyl.

The term "halogen", either alone or in compound words such as "haloalkyl", denotes fluorine, chlorine, bromine or iodine. Further, when used in compound words such as "haloalkyl" said alkyl may be partially halogenated or fully substituted with halogen atoms which may be the same or different. Examples of haloalkyl include $CH_2CH_2F$, $CF_2CF_3$ and $CH_2CHFCl$. Similarly, this definition applies to haloalkoxy and haloalkylthio.

The total number of carbon atoms in a substituent group is indicated by the $C_i$-$C_j$ prefix where i and j are numbers from 1 to 7. For example, $C_1$-$C_3$ alkylsulfonyl would designate methylsulfonyl through propylsulfonyl, $C_2$ alkoxyalkoxy would designate $OCH_2OCH_3$, $C_2$ cyanoalkyl would designate $CH_2CN$ and $C_3$ cyanoalkyl would designate $CH_2CH_2CN$ and $CH(CN)CH_3$.

PREFERRED COMPOUNDS

Preferred for reasons of increased ease of synthesis and/or greater herbicidal efficacy are:
1. Compounds of Formula I
where
X is $C_1$-$C_2$ alkyl, $C_1$-$C_2$ alkoxy, Cl, F, Br, I, $CH_2F$, $CF_3$, $OCH_2CH_2F$, $OCH_2CHF_2$, $OCH_2CF_3$, $CH_2Cl$ or $CH_2Br$; and
Y is H, $C_1$-$C_2$ alkyl, $C_1$-$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$,

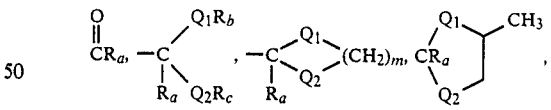

$CH_2SCH_3$, cyclopropyl, $C\equiv CH$ or $C\equiv CCH_3$;
$R_a$ is H or $CH_3$; and
Z is CH or N.
2. Compounds of Preferred 1
where
W is O;
$R_f$ is H, $CH_3$, $C_1$ haloalkyl, halogen or $OCH_3$;
$R_g$ is $C_1$-$C_2$ haloalkyl, ethyl, $W_2R_{11}$, $CH_2OCH_3$, $CH_2SCH_3$, $CH_2CN$, $C_1$-$C_2$ alkylamino or $N(CH_3)_2$;
$R_7$ is H, $C_2$-$C_3$ cyanoalkyl, $C_3$-$C_4$ alkenyl or $C_3$-$C_4$ alkynyl;
$R_8$ is $C_1$-$C_4$ alkyl, $C_1$-$C_4$ haloalkyl, $C_3$-$C_4$ alkenyl, $C_3$-$C_4$ alkynyl, $C_2$-$C_4$ alkoxyalkyl or cyclopropyl; and
$R_{11}$ is $C_1$-$C_3$ alkyl, $C_1$-$C_2$ haloalkyl, allyl or propargyl.
3. Compounds of Preferred 2 where J is J-1.

4. Compounds of Preferred 2 where J is J-2.
5. Compounds of Preferred 2 where J is J-3.
6. Compounds of Preferred 2 where J is J-4.
7. Compounds of Preferred 2 where J is J-5.
8. Compounds of Preferred 3
where
$R_7'$ is $C_1$–$C_3$ alkyl;
$R_7$ is H, $C_2$–$C_3$ cyanoalkyl, allyl or propargyl;
$R_8$ is $C_1$–$C_3$ alkyl, allyl, propargyl or cyclopropyl;
$R_9$ is $CH_2CH_2R_{10}$, $CH_2CH_2SCH_3$, propargyl or cyclopropylmethyl;
$R_9'$ is $C_1$–$C_3$ alkyl, allyl, $CH_2CH_2OCH_3$ or $CH_2CH_2Cl$; and
$R_{10}$ is OH, CN or $OSO_2CH_3$.
9. Compounds of Preferred 8 where
A is A-1;
X is $CH_3$, $OCH_3$, $OCH_2CH_3$, Cl or $OCH_2CF_3$; and
Y is $CH_3$, $OCH_3$, $CH_2CH_3$, $CH_2OCH_3$, $NHCH_3$ or $CH(OCH_3)_2$.
10. Compounds of Preferred 9 where Z is CH.
11. Compounds of Preferred 9 where Z is N.
12. Compounds of Preferred 4 where
$R_7$ is H, $C_2$–$C_3$ cyanoalkyl, allyl or propargyl; and
$R_8$ is $C_1$–$C_3$ alkyl, allyl, propargyl or cyclopropyl.
13. Compounds of Preferred 12
where
A is A-1;
X is $CH_3$, $OCH_3$, $OCH_2CH_3$, Cl or $OCH_2CF_3$; and
Y is $CH_3$, $OCH_3$, $CH_2CH_3$, $CH_2OCH_3$, $NHCH_3$ or $CH(OCH_3)_2$.
14. Compounds of Preferred 13 where Z is CH.
15. Compounds of Preferred 13 where Z iz N.
16. Compounds of Preferred 5
where
$R_7$ is H, $C_2$–$C_3$ cyanoalkyl, allyl or propargyl; and
$R_8$ is $C_1$–$C_3$ alkyl, allyl, propargyl or cyclopropyl.
17. Compounds of Preferred 16
where
A is A-1;
X is $CH_3$, $OCH_3$, $OCH_2CH_3$, Cl or $OCH_2CF_3$; and
Y is $CH_3$, $OCH_3$, $CH_2CH_3$, $CH_2OCH_3$, $NHCH_3$ or $CH(OCH_3)_2$.
18. Compounds of Preferred 17 where Z is CH.
19. Compounds of Preferred 17 where Z is N.
20. Compounds of Preferred 6
where
$R_7$ is H, $C_2$–$C_3$ cyanoalkyl, allyl or propargyl; and
$R_8$ is $C_1$–$C_3$ alkyl, allyl, propargyl or cyclopropyl.
21. Compounds of Preferred 20
where
A is A-1;
X is $CH_3$, $OCH_3$, $OCH_2CH_3$, Cl or $OCH_2CF_3$; and
Y is $CH_3$, $OCH_3$, $CH_2CH_3$, $CH_2OCH_3$, $NHCH_3$ or $CH(OCH_3)_2$.
22. Compounds of Preferred 21 where Z is CH.
23. Compounds of Preferred 21 where Z is N.
24. Compounds of Preferred 7
where
$R_6$ is $SO_2N(OCH_3)CH_3$, $SO_2NR_7R_8$, $CO_2CH_2CF_3$ or $CO_2CH_2CH_2R_{10}$;
$R_7$ is H, $C_2$–$C_3$ cyanoalkyl, allyl or propargyl;
$R_8$ is $C_1$–$C_3$ alkyl, allyl, propargyl or cyclopropyl.
25. Compounds of Preferred 24
where
A is A-1;
X is $CH_3$, $OCH_3$, $OCH_2CH_3$, Cl or $OCH_2CF_3$; and
Y is $CH_3$, $OCH_3$, $CH_2CH_3$, $CH_2OCH_3$, $NHCH_3$ or $CH(OCH_3)_2$.
26. Compounds of Preferred 25 where Z is CH.
27. Compounds of Preferred 25 where Z is N.

Specifically Preferred for reasons of greatest ease of synthesis and/or greatest herbicidal efficacy are:
N2-[(4,6-dimethoxyprimidin-2-yl)aminocarbonyl]-N3-ethyl-2,3-pyridinedisulfonamide; and
N2-[(4,6-dimethoxypyrimidin-2-yl)aminocarbonyl]-N3-methyl-2,3-pyridinedisulfonamide.

DETAILED DESCRIPTION OF THE INVENTION

Synthesis

Compounds of Formula I can be synthesized either by one or more of the methods described in U.S. Pat. No. 4,456,469, or by the reaction of sulfonamides II with the phenyl ester of the appropriate carbamic acid III in the presence of an equimolar quantity of a tertiary amine base such as 1,8-diazabicyclo[5.4.0]undec-7-ene (DBU) as shown in Equation 1.

Equation 1

$$JSO_2NH_2 + PhOC(=O)N(R)-A \xrightarrow[(2)\ H_3O^+]{(1)\ DBU} I$$

II    III wherein J, R, and A are as previously defined.

The reaction shown in Equation 1 is best carried out at 25° C. in a solvent such as dioxane or acetonitrile for 1–2 hours under an inert atmosphere as described in European Patent Application No. 70,804 (published Jan. 26, 1983). The desired products of Formula I can be conveniently isolated by acidifying the reaction solution with aqueous hydrochloric acid. Alternatively, the aqueous layer can be extracted with a solvent such as methylene chloride or ethyl acetate. Drying and evaporation of the solvent affords the desired products. The phenyl carbamates can be synthesized by treatment of the corresponding heterocyclic amines of Formula A-NHR with diphenyl carbonate or phenyl chloroformate in the presence of a base such as sodium hydride, pyridine, or potassium carbonate with a catalytic amount of 4-dimethylaminopyridine. The mixture is stirred at temperatures between 25° and 65° C. in a suitable solvent such as tetrahydrofuran for 12–36 hours.

The required sulfonamides of Formula II can be synthesized by either one of the methods shown below in Equations 2 and 3.

Equation 2 depicts the reaction of sulfonyl chlorides of Formula IV with ammonia to give sulfonamide of Formula II.

Equation 2

$$JSO_2Cl \xrightarrow{NH_3} JSO_2NH_2$$

IV    II wherein J is as previously defined.

The amination of Equation 2 is conveniently effected by adding at least two molar equivalents of either anhydrous ammonia or concentrated ammonium hydroxide to a solution of the sulfonyl chloride IV in a suitable solvent such as diethyl ether, tetrahydrofuran or methylene chloride at temperatures between −30° and 25° C. The desired sulfonamides of Formula II are isolated either by filtration, in which case the by-product ammonium chloride is removed by washing with water, or extraction into a suitable organic solvent such as methylene chloride or ethyl acetate. Drying and evaporation of the solvent then affords the products II which are usually sufficiently pure to be carried directly on to the next step.

Sulfonamides of Formula II can also be prepared as shown in Equation 3 by treatment of the corresponding N-t-butylsulfonamides VI with an appropriate acid such as trifluoroacetic (TFA), polyphosphoric (PPA), or p-toluenesulfonic acid (p-TSA).

Equation 3

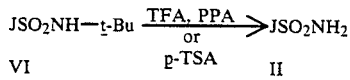

wherein J is as previously defined.

The reaction of Equation 3 is conveniently carried out by stirring a solution of the compound of Formula VI in excess trifluoroacetic acid (approximately 0.3M) at about 25° C. for 1–72 hours. The desired sulfonamides of Formula II are then isolated by removal of the volatiles in vacuo and crystallization from a suitable solvent such as diethyl ether, 1-chlorobutane, or ethyl acetate. Alternatively, the N-t-butylsulfonamides of Formula VI can be treated with a catalytic amount of p-toluenesulfonic acid monohydrate in a solvent such as toluene or xylenes at reflux temperature for 1–6 hours. The desired products are then isolated in a manner analogous to the one described above. For use of polyphosphoric acid in the deprotection of N-t-butylsulfonamides, see J. G. Lombardino, *J. Org. Chem.*, 36, 1843 (1971); for use of trifluoroacetic acid, see J. D. Catt and W. L. Matier, *J. Org. Chem.*, 38, 1974 (1973).

Sulfonamides of Formula VI can be prepared by the reaction of sulfonyl chlorides of Formula IV with excess t-butyl amine as shown in Equation 4.

Equation 4

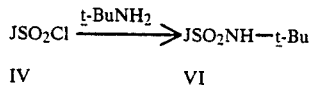

wherein J is as previously defined.

Sulfonyl chlorides of Formula IV can be prepared according to the procedures described in U.S. Pat. No. 4,456,469. Alternatively, the procedures of South African Patent Application No. 84/8844 may be utilized which describe the conversion of mercapto or arylmethylthio compounds to sulfonyl chlorides via treatment with hypochlorite solution.

Sulfonyl chlorides of Formula IVa may also be prepared via metallation of 2-fluoropyridine derivatives with lithium diisopropyl amide (LDA) according to the procedure of T. Gungor, F. Marsais and G. Queguiner, *J. Organomet. Chem.*, 1981, 215, 139–150, followed by treatment with sulfur dioxide and N-chlorosuccinimide (NCS) as shown in Equation 5.

Equation 5

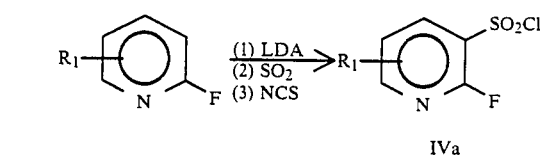

wherein $R_1$ is as previously defined.

Sulfonyl chlorides of Formula IVb can be prepared from compounds of Formula VII as shown in Equation 6 and described in U.S. Pat. No. 4,420,325.

Equation 6

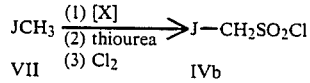

wherein
J is as previously defined; and
[X] is a suitable halogenating reagent which would be obvious to one skilled in the art.

The sulfides of Formula VIII can be prepared by the reaction of a halo pyridine compound of Formula IX with an appropriate mercaptan in the presence of a base as described in U.S. Pat. No. 4,456,469 and shown in Equation 7.

Equation 7

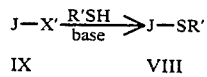

wherein
X' is F, Cl, or Br; and
R' is $C_1$–$C_4$ alkyl or benzyl.

The esters of Formula VIIIg, VIIIh, and VIIIj can be prepared by either of the two methods shown in Equation 8. The first method involves metallation of a 2-fluoropyridine derivative as previously described in Equation 5, followed by treatment with ethyl or methyl chloroformate which afforded esters of Formula XIII. Mercaptide displacement as described in Equation 7 resulted in esters of Formula VIIIg. Acid catalyzed transesterification using the appropriate alcohol as the solvent afforded esters of Formula VIIIh.

The second method involves the alkylation of a 2-mercaptonicotinic acid derivative VIIIi with alkyl halides utilizing a variety of bases such as potassium carbonate or potassium t-butoxide, followed by conversion to the acid halides by any number of standard reagents such as thionyl chloride, phosphorous trichloride or pentachloride, or oxalyl chloride. The acid chlorides were then treated with the appropriate alcohols in the presence of an acid acceptor such as triethylamine, to afford esters of Formula VIIIh. Conversion of the sulfides VIIIh to the sulfonamides VIIIj was carried out as previously described.

Equation 8

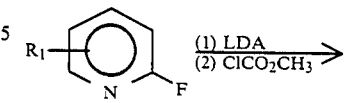

A

-continued
Equation 8

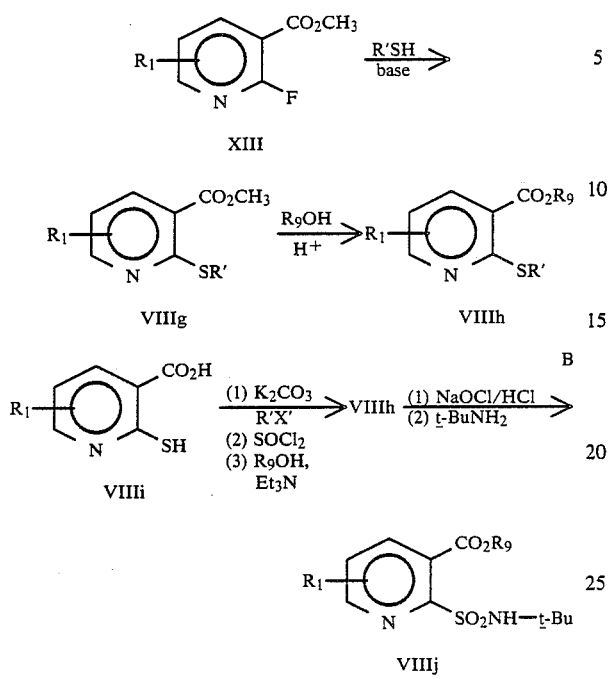

wherein
R' is $C_1$–$C_4$ alkyl or benzyl;
$R_9$ can also be $R'_9$; and
X', R', $R_1$, $R_9$ and $R'_9$ are as previously defined.

The sulfonamides of General Formula XIIa can be prepared as shown in Equation 9. However, for the preparation of primary or unhindered secondary sulfonamides, a protective group is needed for a later stage in the synthetic sequence. A representative example is shown in Equation 10 where a t-butyl protective group is utilized for the synthesis of sulfonamide IIa.

Equation 9

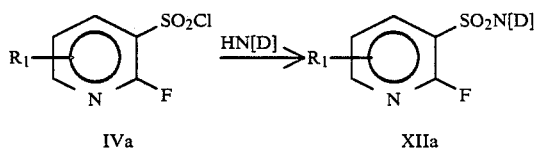

wherein
[D] is $R_dR_3$, $R_7R_8$, $R'_7R_8$, or $H_2$; and
$R_1$, $R_d$, $R_e$, $R_7$, $R_8$ and $R'_7$ are as previously defined.

Equation 10

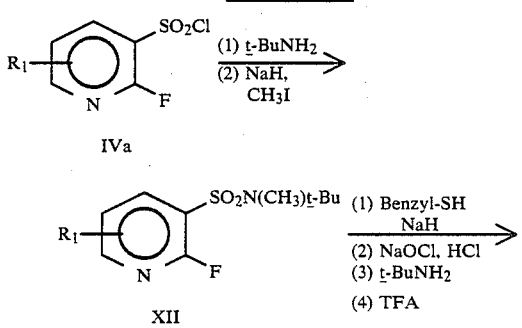

-continued
Equation 10

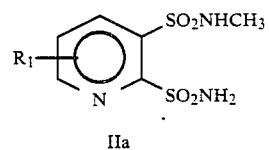

wherein $R_1$ is as previously defined.

The difluoro compounds of Formula XIVa in Equation 11 can be prepared using the reactions previously described. Treatment with one equivalent of various $R_1$ nucleophiles (those that are available in the art) results in a mixture of products which can be separated. An example of the use of sodium methoxide as the reactive nucelophile is shown. Intermediates XIVb and XIVc can be separated and further derivatized as previously described.

Equation 11

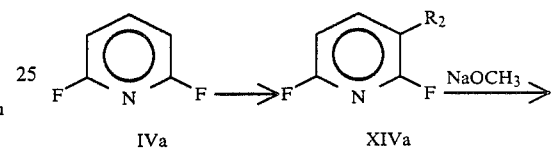

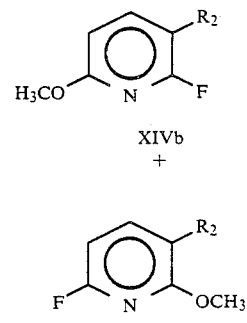

wherein $R_2$ is as previously defined.

An alternative method to prepare esters of Formula XVd is shown in Equation 12. Mercaptide displacement of a 2,6-dihalopyridine can be achieved followed by conversion to the sulfonamide XVa as previously described. Treatment with two equivalents of a strong base such as n-butyllithium in a similar manner to that described by P. Breant, F. Marsalis, and G. Queguiner, *Synthesis*, 1983, 822–824, followed by treatment with carbon dioxide affords the acids of Formula XVb. The acids can then be treated with various $R_1$ nucleophiles such as alkoxides, mercaptides or amines to afford the acids of Formula XVc (using sodium methoxide as an example) which can then be esterified with the appropriate alcohols utilizing standard 1,3-dicyclohexylcarbodiimide (DCC) coupling conditions to afford esters of Formula XVd.

Equation 12

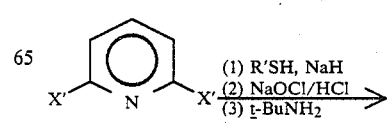

Equation 12

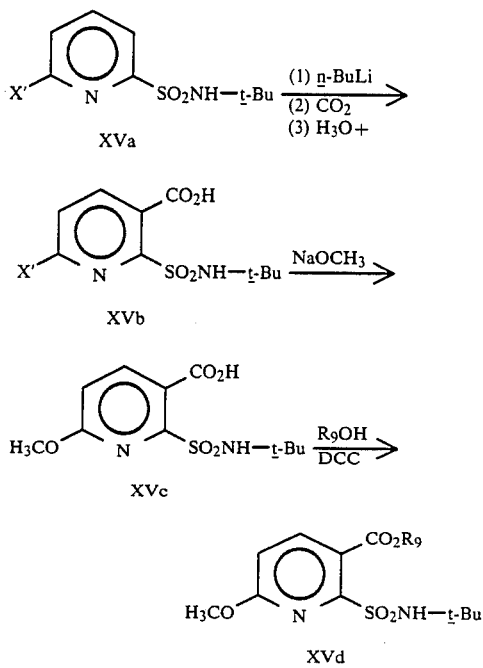

wherein
R₉ can also be R'₉;
X' is F or Cl; and
R', R₉ and R'₉ are as previously defined.

In an analogous manner, sulfonamides of General Formula XVIb can be prepared as shown in Equation 13. Treatment of XVa with strong base followed by an appropriate disulfide affords sulfides of Formula XVIa. Further elaboration utilizing chemistry previously described affords sulfonamides of Formula XVIb.

Equation 13

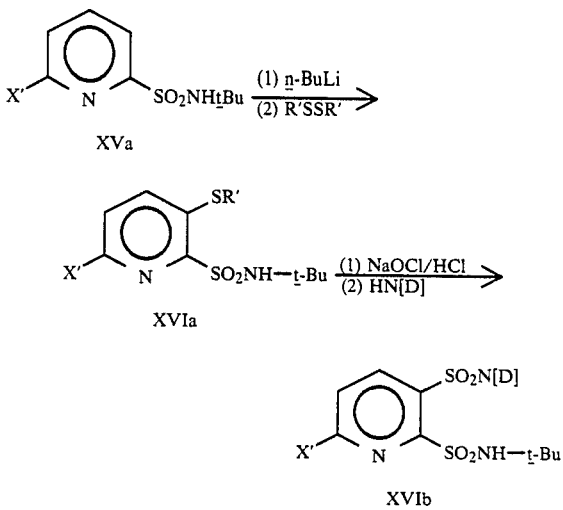

wherein
X' is F or Cl; and
R' and [D] are as previously defined.

A choice by one skilled in the art of the appropriate methods for preparing compounds of Formula I must take into account the nature of the substituents $R_1$ through $R_{11}$, and Rd through Rg, and their chemical compatibility with the reaction conditions of Equations 1 through 13.

The heterocyclic amines of Formula A-NHR in Equation 1 above can be prepared by methods known in the literature, or simple modifications thereof, by those skilled in the art. For instance, EP-A No. 84,224 (published July 27, 1983) and W. Braker et al., *J. Chem. Soc.*, 69, 3072 (1947) describes methods for preparing aminopyridines and triazines substituted by acetal groups such as dialkoxymethyl or 1,3-dioxolan-2-yl, among other groups. Also, for example, South African patent application Nos. 82/5045 and 82/5671 describe methods for preparing aminopyridines and triazines substituted by haloalkyl or haloalkylthio groups such as $OCH_2CH_2F$, $OCH_2CF_3$, $SCF_2H$, or $OCF_2H$, among other groups. South African patent application No. 83/7434 (published Oct. 5, 1983) describes methods for the synthesis of cyclopropylpyrimidines and triazines substituted by such groups as alkyl, haloalkyl, alkoxy, haloalkoxy, alkylamino, dialkylamino or alkoxyalkyl.

The 5,6-dihydrofuro[2.3-d]pyrimidine-2-amines, the cyclopenta[d]pyrimidine-2-amines (A is A-2) and the 6,7-dihydro-5H-pyrano[2.3-d]pyrimidin-2-amines (A is A-3) can be prepared as described in EP-A No. 15,683. The furo[2.3-d]pyrimidin-2-amines (A is A-4) are described in EP-A No. 46,677.

Compounds of Formula A-NHR where A is A-5 are described in EP-A-73,562. Compounds where A is A-6 are described in EP-A-94,260.

In addition, general methods for preparing aminopyrimidines and triazines have been reviewed in the following publications:

The Chemistry of Heterocyclic Compounds", a series published by Interscience Publishers, Inc., New York and London;

"Pyrimidines", Vol. 16 of the same series by D. J. Brown;

"s-Triazines and Derivatives", Vol. 13 of the same series by E. M. Smolin and L. Rappoport; and F. C. Schaefer, U.S. Pat. No. 3,154,547 and K. R. Huffman and F. C. Schaefer, *J. Org. Chem.*, 28, 1812 (1963), which describes the synthesis of triazines.

Preparation in view of the above would be obvious to one skilled in the art. Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following specific examples. Temperatures are reported in degrees Celsius; abbreviations for nuclear magnetic resonance (NMR) are: s=singlet, d=doublet, t=triplet, m=multiplet, and peak positions are reported as parts per million downfield from internal tetramethylsilane. Infrared (IR) peak positions are given in reciprocal centimeters (cm$^{-1}$).

EXAMPLE 1

Preparation of 2,6-Difluoro-3-pyridinecarboxylic acid, methyl ester

To a stirred solution of 91 ml (0.182 mol) of 2.0 molar lithium diisopropylamide (in hexanes) in 200 mL dry tetrahydrofuran cooled to −70° under nitrogen was added dropwise a solution of 20.0 g of 2,6-difluoropyridine (0.174 mol) in 75 mL dry tetrahydrofuran such that the temperature was maintained below −60°. The solution was stirred at −70° fo 3 hours and was then added via a cannula to a solution 21.7 g (0.230 mol) of methyl chloroformate in 100 mL dry tetrahydrofuran cooled to −70° under nitrogen. After stirring another hour at −70°, the mixture was poured into water and extracted with ether. The combined organic layers were washed with brine, dried over magnesium sulfate, and evaporated to a semisolid which was purified by flash chromatography to afford 13.0 g (43%) orange oil: NMR (CDCl$_3$, 200 MHz) 3.95 (3H, s), 6.9 (1H, m), 8.5 (1H, m); IR (neat) 1745, 1730, 1610, 1415, 1290 cm$^{-1}$.

EXAMPLE 2

Preparation of 2-Fluoro-6-Methoxy-3-Pyridinecarboxylic Acid, Methyl Ester

To a stirred solution of 15.0 g (0.0867 mol) of the product from Example 1 in 240 mL dry tetrahydrofuran cooled to −78° was added dropwise 22.7 mL (0.0993 mol) of 25% sodium methoxide in methanol solution over 45 minutes. After warming to −20°, the mixture was poured into ice water, acidified with 1 normal hydrochloric acid and extracted with ether. The combined organic layers were washed with brine, dried over magnesium sulfate, and evaporated to a semisolid which was purified by flash chromatography to afford 3.2 g (17%) light yellow solid: m.p. 81°-82°; NMR (CDCl$_3$, 200 MHz) 3.9 (3H, s), 3.98 (3H, s), 6.67 (1H, d, J=9 Hz), 8.25 (1H, m); IR (nujol) 1715, 1615, 1290 cm$^{-1}$.

EXAMPLE 3

Preparation of 6-Methoxy-2-(Phenylmethylthio)-3-Pyridinecarboxylic Acid, Methyl Ester To a stirred mixture of 0.8 g (0.0161 mol) of 50% sodium hydride (in mineral oil), which had been washed with hexanes, in 20 mL dry dimethylformamide cooled to −5° under nitrogen was added dropwise 1.9 mL (0.0161 mol) benzyl mercaptan The suspension was stirred at room temperature for 1 hour, cooled to 0°, and a solution of 3.2 g (0.0147 mol) of the product of Example 2 in 20 mL dry dimethylformamide was added dropwise. After warming to room temperature, the solution was poured into water and extracted with ether. The combined organic layers were washed with water and with brine, dried over magnesium sulfate, and evaporated to an oil which was purified by flash chromatography to afford 3.0 g (64%) of a yellow solid: m.p. 67°-71°; NMR (CDCl$_3$, 200 MHz) 3.88 (3H, s), 3.96 (3H, s), 4.46 (2H, s), 6.44 (1H, d, J=9 Hz), 7.2-7.5 (5H, m), 8.1 (1H, d, J=9 Hz); IR (nujol) 1700, 1580, 1305, 1255 cm$^{-1}$.

EXAMPLE 4

Preparation of 2-[1,1-Dimethylethyl)Aminosulfonyl]-6-Methoxy-3-Pyridinecarboxylic Acid, Methyl Ester To a vigorously stirred mixture of 3.7 g (0.0129 mol) of the product from Example 3 in 79 mL methylene chloride and 41 mL water cooled to 0° was added 6.3 mL (0.0759 mol) concentrated hydrochloric acid followed by the dropwise addition of 79 mL (0.053 mol) of a 5% sodium hypochlorite solution such that the temperature was maintained below 5°. After the mixture was stirred for an additional 30 minutes at 0° the reaction was poured into water and extracted with methylene chloride. The combined organic layers were washed with brine, dried over magnesium sulfate, and filtered. The filtrate was stirred and cooled to −70° under nitrogen, and 4.7 (0.0645 mol) of t-butyl amine was added dropwise. The reaction mixture was allowed to warm to −20°, poured into water, acidified with 1 normal hydrochloric acid, and extracted with methylene chloride. The combined organic layers were washed with brine, dried over magnesium sulfate, and evaporated to a semisolid which was purified by flash chromatography to afford 3.0 g (77%) yellow solid: m.p. 128°-130°; NMR (CDCl$_3$, 200 MHz) 1.27 (9H, s), 3.94 (3H, s), 4.05 (3H, s) 5.75 (NH), 6.9 (1H, d, J=9 Hz), 7.95 (1H, d, J=9 HZ); IR (nujol) 3260, 1740, 1605, 1325, 1125 cm$^{-1}$.

EXAMPLE 5

Preparation of 2-(Aminosulfonyl)-6-Methoxy-3-Pyridine-Carboxylic Acid, Methyl Ester A solution of 2.9 g (0.0096 mol) of the product from Example 4 was stirred in 50 mL trifluoroacetic acid at room temperature for 20 hours. The solution was evaporated to afford 2.4 g (100%) white solid: m.p. 142.5°-144.5°; NMR (CDCl, 200 MHz) 3.97 (3H, s), 4.1 (3H, s), 5.6 (NH$_2$), 6.9 (1H, d, J=9 Hz), 8.1 (1H, d, J=9 Hz); IR (nujol) 3305, 3205, 1715, 1590, 1355, 1320, 1175 cm$^{-1}$.

EXAMPLE 6

Preparation of 2-[[(4,6-Dimethoxypyrimidin-2-yl)aminocarbonyl]aminosulfonyl]-6-Methoxy-3-Pyridine-Carboxylic Acid, Methyl Ester To a stirred suspension of 0.4 g (0.0016 mol) of the product from Example 5 and 0.54 g (0.002 mol) of phenyl(4,6-dimethoxypyrimidin-2-yl) carbamate in 4 mL acetonitrile was added dropwise 0.30 g (0.002 mol) of 1,8-diazobicyclo[5.4.0]undec-7-ene and stirred for 30 minutes. The solution was diluted with water and acidified with 1 normal hydrochloric acid. The resulting precipitate was collected and washed with water and with ether to afford 0.57 g (84%) white solid: m.p.

194°–196°; NMR (CDCl$_3$, 200 MHz), 3.83 (3H, s), 3.95 (9H, s), 5.8 (1H, s), 6.95 (1H, d, J=9 Hz), 7.4 (NH), 8.1 (1H, d, J=9 Hz), 12.8 (NH); IR (nujol) 3140, 1740, 1720, 1640, 1360, 1195, 1140 cm$^{-1}$.

EXAMPLE 7

Preparation of N-(1,1-Dimethylethyl)-2-Fluoro-3-Pyridinesulfonamide

To a stirred solution of 396 mL (0.740 mol) of 1.9 molar lithium diisopropylamide (in hexanes) in 1.5 L dry tetrahydrofuran cooled to −70° under nitrogen was added dropwise a solution of 65 g (0.670 mol) of 2-fluoropyridine in 150 mL dry tetrahydrofuran such that the temperature was maintained below −65°. The suspension was stirred at −70° for another 3.5 hours and 86 g (1.34 mol) of sulfur dioxide was added while maintaining the temperature below −65°. After stirring another 15 minutes at −70°, the reaction was allowed to warm to 0° and evaporated to half the original volume and diluted with ether. The white precipitate was collected under nitrogen, washed with ether, and dried. The solid was dissolved in 800 mL acetic acid and cooled to 10°–20°. To this stirred solution was added portionwise 99.4 g (0.740 mol) of N-chlorosuccinimide while maintaining the temperature below 20°. After stirring another 30 minutes, the suspension was evaporated, diluted with water and extracted with methylene chloride. The combined organic phases were washed with saturated aqueous sodium bicarbonate solution until no more gas evolution, washed with brine, dried over magnesium sulfate, and filtered. The filtrate was cooled to −70° under nitrogen and to this stirred solution was added dropwise 199 g (2.7 mol) of t-butylamine. The suspension was poured into ice water, acidified with concentrated hydrochloric acid, and extracted with methylene chloride. The combined organic layers were washed with brine, dried over magnesium sulfate, and evaporated to an oil which was purified by flash chromatography to afford 29.1 g (19%) of a brown solid which was further washed with cold n-butylchloride to afford 22.4 g (14.5%) of a white solid: m.p. 95°–97°; NMR (CDCl$_3$, 200 MHz) 1.25 (9H, s), 4.9 (NH), 7.35 (1H, m), 8.3–8.5 (2H, m).

EXAMPLE 8

Preparation of N-(1,1-Dimethylethyl)-2-Fluoro-N-Methyl-3-Pyridinesulfonamide

To a stirred suspension of 3.4 g (0.071 mol) of 50% sodium hydride (in mineral oil), which had been washed with hexanes, in 120 mL dry dimethyldoramide cooled to 0° under nitrogen was added dropwise a solution of 15.0 g (0.065 mol) of the product from Example 7 in 120 mL dry dimethylformamide. After stirring at room temperature for 1 hour, the mixture was cooled to 0° and 12.2 g (0.086 mol) of methyl iodide was added dropwise. After warming to room temperature the reaction was poured into ice water and extracted with ether. The combined organic layers were washed with brine, dried over magnesium sulfate, and evaporated to 15.9 g (99%) oil; NMR (CDCl$_3$, 200 MHz), 1.32 (9H, s), 3.1 (3H, s), 7.3 (1H, m), 8.3–8.4 (2H, m); IR (neat) 1590, 1570, 1335, 1155 cm$^{-1}$.

EXAMPLE 9

Preparation of N-(1,1-Dimethylethyl)-N-Methyl-2-(Phenylmethylthio)-3-Pyridinesulfonamide Using the same procedure as in Example 3, 15.9 g (0.065 mol) of the product from Example 8 was converted to 19.5 g (86%) yellow solid: m.p. 92°–94°; NMR (CDCl$_3$), 200 MHz) 1.26 (9H, s), 3.1 (3H, s), 4.5 (2H, s), 7.0–7.5 (6H, m), 8.2 (1H, m); IR (nujol) 1570, 1385, 1315, 1150, 1120 cm$^{-1}$.

EXAMPLE 10

Preparation of N2, N3-Bis(1,1-Dimethylethyl)-N3-Methyl-2,3-Pyridinedisulfonamide Using the same procedure as in Example 4, 19.5 g (0.056 mol) of the product from Example 9 was converted to a tan solid which was washed with n-butylchloride to afford 13.1 g (66%) white solid: m.p. 155°–156.5°; NMR (CDCl$_3$, 200 MHz) 1.23 (9H, s), 1.33 (9H, s), 3.1 (3H, s), 6.0 (NH), 1H, m), 8.5 (1H, m), 8.8 (1H, m); IR (nujol) 3320, 1340, 1325, 1160, 1120 cm$^{-1}$.

EXAMPLE 11

Preparation of N3-Methyl-2,3-Pyridinedisulfonamide

A stirred solution of 13.1 g (0.036 mol) of the product from Example 10 in 150 mL trifluoroacetic acid was refluxed for 5 hours. After cooling to room temperature, the solution was evaporated to a solid which was washed with ether to afford 9.6 g (100%) white solid: m.p. 220°–223°; NMR (DMSO-d$_6$, 200 MHz), 2.5 (3H, d), 6.9 (NH), 7.65 (NH$_2$), 7.85 (1H, m), 8.45 (1H, m), 8.9 (1H, m); IR (nujol) 3380, 3320, 3180, 1355, 1170 cm$^{-1}$.

EXAMPLE 12

Preparation of N2-[(4,6-Dimethoxyprimidin-2-yl)aminocarbonyl]-N3-Methyl-2,3-Pyridinedisulfonamide To a stirred suspension of 4.15 g (0.0165 mol) of the product from Example 11 and 5.0 g (0.018 mol) of phenyl (4,6-dimethoxypyrimidin-2-yl)carbamate in 50 mL acetonitrile was added dropwise 2.8 g (0.018 mol) of 1,8-diazabicyclo[5.4.0]undec-4-ene and stirred for 30 minutes. The solution was diluted with water and acidified with 1 normal hydrochloric acid. The resulting precipitate was collected and washed with water and with ether to afford 6.4 g (82%) white solid: m.p. 147°–148.5°; NMR (CDCl$_3$, 200 MHz) 2.7 (3H, d, J=7 Hz), 3.97 (6H, s), 5.8 (1H, s), 6.15 (1H, m), 7.3 (NH), 7.7 (1H, m), 8.55 (1H, m), 8.8 (1H, m), 13.1 (NH); IR (nujol) 3310, 1740, 1610, 1340, 1190, 1165 cm$^{-1}$.

By applying the procedures of Examples 1 through 12 and Equations 1 through 13, the compounds in Tables I through X can be prepared by one skilled in the art.

| General Formula For Tables | |
|---|---|
| General Formula 1 | 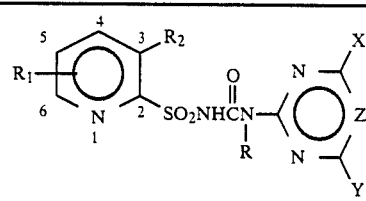 |

-continued
General Formula For Tables

General Formula 2
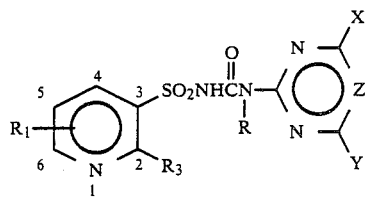

General Formula 3
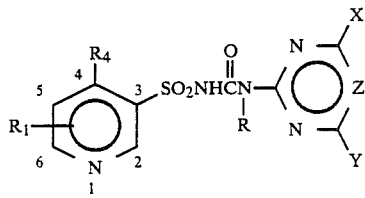

General Formula 4
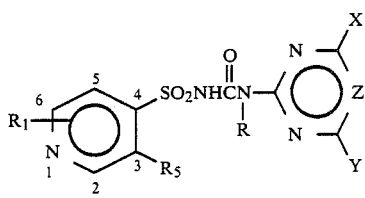

General Formula 5
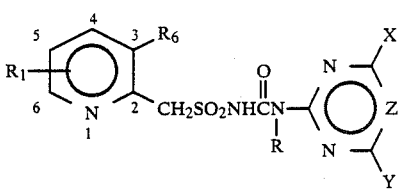

-continued
General Formula For Tables

General Formula 6
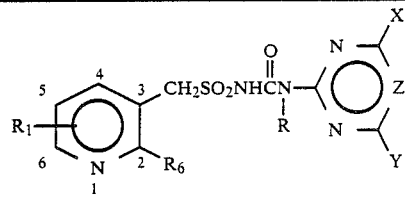

General Formula 7
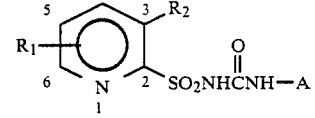

General Formula 8
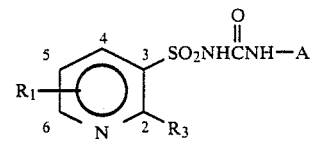

General Formula 9
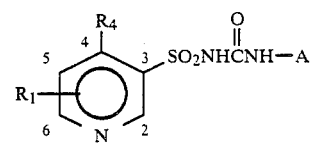

General Formula 10
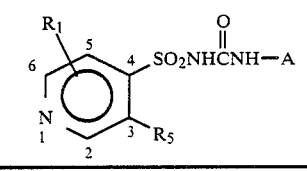

TABLE I

General Formula 1

| $R_1$ | $R_2$ | R | X | Y | Z | m.p. (°C.) |
|---|---|---|---|---|---|---|
| 6-$CH_2CH_3$ | $SO_2N(CH_3)_2$ | H | $OCH_3$ | $OCH_3$ | CH | |
| 6-$CH_2CH_3$ | $SO_2N(CH_3)_2$ | H | $OCH_3$ | $CH_3$ | CH | |
| 6-$CH_2CH_3$ | $SO_2N(CH_3)_2$ | H | Cl | $OCH_3$ | CH | |
| 6-$CH_2CH_3$ | $SO_2N(CH_3)_2$ | H | $CH_3$ | $CH_3$ | CH | |
| 6-$CH_2CH_3$ | $SO_2N(CH_3)_2$ | H | $OCH_3$ | $OCH_3$ | N | |
| 6-$CH_2CH_3$ | $SO_2N(CH_3)_2$ | H | $OCH_3$ | $CH_3$ | N | |
| 6-$CH_2CH_3$ | $SO_2N(CH_3)_2$ | H | $OCH_2CH_3$ | $NHCH_3$ | N | |
| 6-$CH_2CH_3$ | $SO_2N(CH_3)_2$ | $CH_3$ | $OCH_2CH_3$ | $CH_3$ | N | |
| 6-$OCH_3$ | $SO_2N(CH_3)_2$ | H | $OCH_3$ | $OCH_3$ | CH | |
| 6-$OCH_3$ | $SO_2N(CH_3)_2$ | H | $OCH_3$ | $CH_3$ | CH | |
| 6-$OCH_3$ | $SO_2N(CH_3)_2$ | H | Cl | $OCH_3$ | CH | |
| 6-$OCH_3$ | $SO_2N(CH_3)_2$ | H | $CH_3$ | $CH_3$ | CH | |
| 6-$OCH_3$ | $SO_2N(CH_3)_2$ | H | $OCH_3$ | $OCH_3$ | N | |
| 6-$OCH_3$ | $SO_2N(CH_3)_2$ | H | $OCH_3$ | $CH_3$ | N | |
| 6-$OCH_3$ | $SO_2N(CH_3)_2$ | H | $OCH_2CH_3$ | $NHCH_3$ | N | |
| 6-$OCH_3$ | $SO_2N(CH_3)_2$ | $CH_3$ | $OCH_3$ | $CH_3$ | N | |
| 6-$OCH_2CH_3$ | $SO_2N(CH_3)_2$ | H | $OCH_3$ | $OCH_3$ | CH | |
| 6-$OCH_2CH_3$ | $SO_2N(CH_3)_2$ | H | $OCH_3$ | $CH_3$ | CH | |
| 6-$OCH_2CH_3$ | $SO_2N(CH_3)_2$ | H | Cl | $OCH_3$ | CH | |
| 6-$OCH_2CH_3$ | $SO_2N(CH_3)_2$ | H | $CH_3$ | $CH_3$ | CH | |
| 6-$OCH_2CH_3$ | $SO_2N(CH_3)_2$ | H | $OCH_3$ | $OCH_3$ | N | |
| 6-$OCH_2CH_3$ | $SO_2N(CH_3)_2$ | H | $OCH_3$ | $CH_3$ | N | |
| 6-$OCH_2CH_3$ | $SO_2N(CH_3)_2$ | H | $OCH_2CH_3$ | $NHCH_3$ | N | |
| 6-$OCH_2CH_3$ | $SO_2N(CH_3)_2$ | $CH_3$ | $OCH_3$ | $CH_3$ | N | |
| 6-$SCH_2CH_3$ | $SO_2N(CH_3)_2$ | H | $OCH_3$ | $OCH_3$ | CH | |
| 6-$SCH_2CH_3$ | $SO_2N(CH_3)_2$ | H | $OCH_3$ | $CH_3$ | CH | |
| 6-$SCH_2CH_3$ | $SO_2N(CH_3)_2$ | H | Cl | $OCH_3$ | CH | |
| 6-$SCH_2CH_3$ | $SO_2N(CH_3)_2$ | H | $CH_3$ | $CH_3$ | CH | |
| 6-$SCH_2CH_3$ | $SO_2N(CH_3)_2$ | H | $OCH_3$ | $OCH_3$ | N | |
| 6-$SCH_2CH_3$ | $SO_2N(CH_3)_2$ | H | $OCH_3$ | $CH_3$ | N | |
| 6-$SCH_2CH_3$ | $SO_2N(CH_3)_2$ | H | $OCH_2CH_3$ | $NHCH_3$ | N | |
| 6-$SCH_2CH_3$ | $SO_2N(CH_3)_2$ | $CH_3$ | $OCH_3$ | $CH_3$ | N | |

TABLE I-continued

| | | General Formula 1 | | | | |
|---|---|---|---|---|---|---|
| $R_1$ | $R_2$ | R | X | Y | Z | m.p. (°C.) |
| 6-SCH$_3$ | SO$_2$N(CH$_3$)$_2$ | H | OCH$_3$ | OCH$_3$ | CH | |
| 6-SCH$_3$ | SO$_2$N(CH$_3$)$_2$ | H | OCH$_3$ | CH$_3$ | CH | |
| 6-SCH$_3$ | SO$_2$N(CH$_3$)$_2$ | H | Cl | OCH$_3$ | CH | |
| 6-SCH$_3$ | SO$_2$N(CH$_3$)$_2$ | H | CH$_3$ | CH$_3$ | CH | |
| 6-SCH$_3$ | SO$_2$N(CH$_3$)$_2$ | H | OCH$_3$ | OCH$_3$ | N | |
| 6-SCH$_3$ | SO$_2$N(CH$_3$)$_2$ | H | OCH$_3$ | CH$_3$ | N | |
| 6-SCH$_3$ | SO$_2$N(CH$_3$)$_2$ | H | OCH$_2$CH$_3$ | NHCH$_3$ | N | |
| 6-SCH$_3$ | SO$_2$N(CH$_3$)$_2$ | CH$_3$ | OCH$_3$ | CH$_3$ | N | |
| 6-N(CH$_3$)$_2$ | SO$_2$N(CH$_3$)$_2$ | H | OCH$_3$ | OCH$_3$ | CH | |
| 6-N(CH$_3$)$_2$ | SO$_2$N(CH$_3$)$_2$ | H | OCH$_3$ | CH$_3$ | CH | |
| 6-N(CH$_3$)$_2$ | SO$_2$N(CH$_3$)$_2$ | H | Cl | OCH$_3$ | CH | |
| 6-N(CH$_3$)$_2$ | SO$_2$N(CH$_3$)$_2$ | H | CH$_3$ | CH$_3$ | CH | |
| 6-N(CH$_3$)$_2$ | SO$_2$N(CH$_3$)$_2$ | H | OCH$_3$ | OCH$_3$ | N | |
| 6-N(CH$_3$)$_2$ | SO$_2$N(CH$_3$)$_2$ | H | OCH$_3$ | CH$_3$ | N | |
| 6-N(CH$_3$)$_2$ | SO$_2$N(CH$_3$)$_2$ | H | OCH$_2$CH$_3$ | NHCH$_3$ | N | |
| 6-N(CH$_3$)$_2$ | SO$_2$N(CH$_3$)$_2$ | CH$_3$ | OCH$_3$ | CH$_3$ | N | |
| 6-NHCH$_3$ | SO$_2$N(CH$_3$)$_2$ | H | OCH$_3$ | OCH$_3$ | CH | |
| 6-NHCH$_3$ | SO$_2$N(CH$_3$)$_2$ | H | OCH$_3$ | CH$_3$ | CH | |
| 6-NHCH$_3$ | SO$_2$N(CH$_3$)$_2$ | H | Cl | OCH$_3$ | CH | |
| 6-NHCH$_3$ | SO$_2$N(CH$_3$)$_2$ | H | CH$_3$ | CH$_3$ | CH | |
| 6-NHCH$_3$ | SO$_2$N(CH$_3$)$_2$ | H | OCH$_3$ | OCH$_3$ | N | |
| 6-NHCH$_3$ | SO$_2$N(CH$_3$)$_2$ | H | OCH$_3$ | CH$_3$ | N | |
| 6-NHCH$_3$ | SO$_2$N(CH$_3$)$_2$ | H | OCH$_2$CH$_3$ | NHCH$_3$ | N | |
| 6-NHCH$_3$ | SO$_2$N(CH$_3$)$_2$ | CH$_3$ | OCH$_3$ | CH$_3$ | N | |
| 6-OCH$_3$ | SO$_2$N(CH$_2$CH$_3$)$_2$ | H | OCH$_3$ | OCH$_3$ | CH | |
| 6-OCH$_3$ | SO$_2$N(CH$_2$CH$_3$)$_2$ | H | OCH$_3$ | CH$_3$ | CH | |
| 6-OCH$_3$ | SO$_2$N(CH$_2$CH$_3$)$_2$ | H | Cl | OCH$_3$ | CH | |
| 6-OCH$_3$ | SO$_2$N(CH$_2$CH$_3$)$_2$ | H | CH$_3$ | CH$_3$ | CH | |
| 6-OCH$_3$ | SO$_2$N(CH$_2$CH$_3$)$_2$ | H | OCH$_3$ | OCH$_3$ | N | |
| 6-OCH$_3$ | SO$_2$N(CH$_2$CH$_3$)$_2$ | H | OCH$_3$ | CH$_3$ | N | |
| 6-OCH$_3$ | SO$_2$N(CH$_2$CH$_3$)$_2$ | H | OCH$_2$CH$_3$ | NHCH$_3$ | N | |
| 6-OCH$_3$ | SO$_2$N(CH$_2$CH$_3$)$_2$ | CH$_3$ | OCH$_3$ | CH$_3$ | N | |
| 6-SCH$_3$ | SO$_2$N(CH$_2$CH$_3$)$_2$ | H | OCH$_3$ | OCH$_3$ | CH | |
| 6-SCH$_3$ | SO$_2$N(CH$_2$CH$_3$)$_2$ | H | OCH$_3$ | CH$_3$ | CH | |
| 6-SCH$_3$ | SO$_2$N(CH$_2$CH$_3$)$_2$ | H | Cl | OCH$_3$ | CH | |
| 6-SCH$_3$ | SO$_2$N(CH$_2$CH$_3$)$_2$ | H | CH$_3$ | CH$_3$ | CH | |
| 6-SCH$_3$ | SO$_2$N(CH$_2$CH$_3$)$_2$ | H | OCH$_3$ | OCH$_3$ | N | |
| 6-SCH$_3$ | SO$_2$N(CH$_2$CH$_3$)$_2$ | H | OCH$_3$ | CH$_3$ | N | |
| 6-SCH$_3$ | SO$_2$N(CH$_2$CH$_3$)$_2$ | H | OCH$_2$CH$_3$ | NHCH$_3$ | N | |
| 6-SCH$_3$ | SO$_2$N(CH$_2$CH$_3$)$_2$ | CH$_3$ | OCH$_3$ | CH$_3$ | N | |
| 6-N(CH$_3$)$_2$ | SO$_2$N(CH$_2$CH$_3$)$_2$ | H | OCH$_3$ | OCH$_3$ | CH | |
| 6-N(CH$_3$)$_2$ | SO$_2$N(CH$_2$CH$_3$)$_2$ | H | OCH$_3$ | CH$_3$ | CH | |
| 6-N(CH$_3$)$_2$ | SO$_2$N(CH$_2$CH$_3$)$_2$ | H | Cl | OCH$_3$ | CH | |
| 6-N(CH$_3$)$_2$ | SO$_2$N(CH$_2$CH$_3$)$_2$ | H | CH$_3$ | CH$_3$ | CH | |
| 6-N(CH$_3$)$_2$ | SO$_2$N(CH$_2$CH$_3$)$_2$ | H | OCH$_3$ | OCH$_3$ | N | |
| 6-N(CH$_3$)$_2$ | SO$_2$N(CH$_2$CH$_3$)$_2$ | H | OCH$_3$ | CH$_3$ | N | |
| 6-N(CH$_3$)$_2$ | SO$_2$N(CH$_2$CH$_3$)$_2$ | H | OCH$_2$CH$_3$ | NHCH$_3$ | N | |
| 6-N(CH$_3$)$_2$ | SO$_2$N(CH$_2$CH$_3$)$_2$ | CH$_3$ | OCH$_3$ | CH$_3$ | N | |
| 6-SCH$_3$ | SO$_2$NHOCH$_3$ | H | OCH$_3$ | OCH$_3$ | CH | |
| 6-SCH$_3$ | SO$_2$NHOCH$_3$ | H | OCH$_3$ | CH$_3$ | CH | |
| 6-SCH$_3$ | SO$_2$NHOCH$_3$ | H | Cl | OCH$_3$ | CH | |
| 6-SCH$_3$ | SO$_2$NHOCH$_3$ | H | CH$_3$ | CH$_3$ | CH | |
| 6-SCH$_3$ | SO$_2$NHOCH$_3$ | H | OCH$_3$ | OCH$_3$ | N | |
| 6-SCH$_3$ | SO$_2$NHOCH$_3$ | H | OCH$_3$ | CH$_3$ | N | |
| 6-SCH$_3$ | SO$_2$NHOCH$_3$ | H | OCH$_2$CH$_3$ | NHCH$_3$ | N | |
| 6-SCH$_3$ | SO$_2$NHOCH$_3$ | CH$_3$ | OCH$_3$ | CH$_3$ | N | |
| 6-SCH$_2$CH$_3$ | SO$_2$NHOCH$_3$ | H | OCH$_3$ | OCH$_3$ | CH | |
| 6-SCH$_2$CH$_3$ | SO$_2$NHOCH$_3$ | H | OCH$_3$ | CH$_3$ | CH | |
| 6-SCH$_2$CH$_3$ | SO$_2$NHOCH$_3$ | H | Cl | OCH$_3$ | CH | |
| 6-SCH$_2$CH$_3$ | SO$_2$NHOCH$_3$ | H | CH$_3$ | CH$_3$ | CH | |
| 6-SCH$_2$CH$_3$ | SO$_2$NHOCH$_3$ | H | OCH$_3$ | OCH$_3$ | N | |
| 6-SCH$_2$CH$_3$ | SO$_2$NHOCH$_3$ | H | OCH$_3$ | CH$_3$ | N | |
| 6-SCH$_2$CH$_3$ | SO$_2$NHOCH$_3$ | H | OCH$_2$CH$_3$ | NHCH$_3$ | N | |
| 6-SCH$_2$CH$_3$ | SO$_2$NHOCH$_3$ | CH$_3$ | OCH$_3$ | CH$_3$ | N | |
| 6-N(CH$_3$)$_2$ | SO$_2$NHOCH$_3$ | H | OCH$_3$ | OCH$_3$ | CH | |
| 6-N(CH$_3$)$_2$ | SO$_2$NHOCH$_3$ | H | OCH$_3$ | CH$_3$ | CH | |
| 6-N(CH$_3$)$_2$ | SO$_2$NHOCH$_3$ | H | Cl | OCH$_3$ | CH | |
| 6-N(CH$_3$)$_2$ | SO$_2$NHOCH$_3$ | H | CH$_3$ | CH$_3$ | CH | |
| 6-N(CH$_3$)$_2$ | SO$_2$NHOCH$_3$ | H | OCH$_3$ | OCH$_3$ | N | |
| 6-N(CH$_3$)$_2$ | SO$_2$NHOCH$_3$ | H | OCH$_3$ | CH$_3$ | N | |
| 6-N(CH$_3$)$_2$ | SO$_2$NHOCH$_3$ | H | OCH$_2$CH$_3$ | NHCH$_3$ | N | |
| 6-N(CH$_3$)$_2$ | SO$_2$NHOCH$_3$ | CH$_3$ | OCH$_3$ | CH$_3$ | N | |
| 6-OCH$_3$ | SO$_2$NHOCH$_3$ | H | OCH$_3$ | OCH$_3$ | CH | |
| 6-OCH$_3$ | SO$_2$NHOCH$_3$ | H | OCH$_3$ | CH$_3$ | CH | |
| 6-OCH$_3$ | SO$_2$NHOCH$_3$ | H | Cl | OCH$_3$ | CH | |
| 6-OCH$_3$ | SO$_2$NHOCH$_3$ | H | CH$_3$ | CH$_3$ | CH | |
| 6-OCH$_3$ | SO$_2$NHOCH$_3$ | H | OCH$_3$ | OCH$_3$ | N | |
| 6-OCH$_3$ | SO$_2$NHOCH$_3$ | H | OCH$_3$ | CH$_3$ | N | |
| 6-OCH$_3$ | SO$_2$NHOCH$_3$ | H | OCH$_2$CH$_3$ | NHCH$_3$ | N | |
| 6-OCH$_3$ | SO$_2$NHOCH$_3$ | CH$_3$ | OCH$_3$ | CH$_3$ | N | |

TABLE I-continued

General Formula 1

| R₁ | R₂ | R | X | Y | Z | m.p. (°C.) |
|---|---|---|---|---|---|---|
| 6-OCH₃ | SO₂NHCH₃ | H | OCH₃ | OCH₃ | CH | |
| 6-OCH₃ | SO₂NHCH₃ | H | OCH₃ | CH₃ | CH | |
| 6-OCH₃ | SO₂NHCH₃ | H | Cl | OCH₃ | CH | |
| 6-OCH₃ | SO₂NHCH₃ | H | CH₃ | CH₃ | CH | |
| 6-OCH₃ | SO₂NHCH₃ | H | OCH₃ | OCH₃ | N | |
| 6-OCH₃ | SO₂NHCH₃ | H | OCH₃ | CH₃ | N | |
| 6-OCH₃ | SO₂NHCH₃ | H | OCH₂CH₃ | NHCH₃ | N | |
| 6-OCH₃ | SO₂NHCH₃ | CH₃ | OCH₃ | CH₃ | N | |
| 6-SCH₃ | SO₂NHCH₃ | H | OCH₃ | OCH₃ | CH | |
| 6-SCH₃ | SO₂NHCH₃ | H | OCH₃ | CH₃ | CH | |
| 6-SCH₃ | SO₂NHCH₃ | H | Cl | OCH₃ | CH | |
| 6-SCH₃ | SO₂NHCH₃ | H | CH₃ | CH₃ | CH | |
| 6-SCH₃ | SO₂NHCH₃ | H | OCH₃ | OCH₃ | N | |
| 6-SCH₃ | SO₂NHCH₃ | H | OCH₃ | CH₃ | N | |
| 6-SCH₃ | SO₂NHCH₃ | H | OCH₂CH₃ | NHCH₃ | N | |
| 6-SCH₃ | SO₂NHCH₃ | CH₃ | OCH₃ | CH₃ | N | |
| H | SO₂NHCH₃ | H | OCH₃ | OCH₃ | CH | 147–148.5 |
| H | SO₂NHCH₃ | H | OCH₃ | CH₃ | CH | |
| H | SO₂NHCH₃ | H | Cl | OCH₃ | CH | 155–157 |
| H | SO₂NHCH₃ | H | CH₃ | CH₃ | CH | 150–152 |
| H | SO₂NHCH₃ | H | OCH₃ | OCH₃ | N | |
| H | SO₂NHCH₃ | H | OCH₃ | CH₃ | N | 153.5–155 |
| H | SO₂NHCH₃ | H | OCH₂CH₃ | NHCH₃ | N | |
| H | SO₂NHCH₃ | CH₃ | OCH₃ | CH₃ | N | |
| 4-CH₃ | SO₂NHCH₃ | H | OCH₃ | OCH₃ | CH | |
| 4-OCH₃ | SO₂NHCH₃ | H | OCH₃ | OCH₃ | CH | |
| 6-CH₃ | SO₂NHCH₃ | H | OCH₃ | OCH₃ | CH | |
| 6-F | SO₂NHCH₃ | H | OCH₃ | OCH₃ | CH | |
| 6-Cl | SO₂NHCH₃ | H | OCH₃ | OCH₃ | CH | |
| H | SO₂NHCH₂CH₃ | H | OCH₃ | OCH₃ | CH | 163–165.5 |
| H | SO₂NHCH₂CH₃ | H | OCH₃ | CH₃ | CH | |
| H | SO₂NHCH₂CH₃ | H | Cl | OCH₃ | CH | 158.5–161 |
| H | SO₂NHCH₂CH₃ | H | CH₃ | CH₃ | CH | 118–121.5 |
| H | SO₂NHCH₂CH₃ | H | OCH₃ | OCH₃ | N | 162–164 |
| H | SO₂NHCH₂CH₃ | H | OCH₃ | CH₃ | N | 158–160 |
| H | SO₂NHCH₂CH₃ | H | OCH₂CH₃ | NHCH₃ | N | |
| H | SO₂NHCH₂CH₃ | CH₃ | OCH₃ | CH₃ | N | 122–125.5 |
| 4-CH₃ | SO₂NHCH₂CH₃ | H | OCH₃ | OCH₃ | CH | |
| 4-OCH₃ | SO₂NHCH₂CH₃ | H | OCH₃ | OCH₃ | CH | |
| 6-CH₃ | SO₂NHCH₂CH₃ | H | OCH₃ | OCH₃ | CH | |
| 6-OCH₃ | SO₂NHCH₂CH₃ | H | OCH₃ | OCH₃ | CH | |
| 6-F | SO₂NHCH₂CH₃ | H | OCH₃ | OCH₃ | CH | |
| 6-Cl | SO₂NHCH₂CH₃ | H | OCH₃ | OCH₃ | CH | |
| H | SO₂NHCH₂CH₂CH₃ | H | OCH₃ | OCH₃ | CH | 138.5–141 |
| H | SO₂NHCH₂CH₂CH₃ | H | OCH₃ | CH₃ | CH | 117–120 |
| H | SO₂NHCH₂CH₂CH₃ | H | Cl | OCH₃ | CH | 125–129 |
| H | SO₂NHCH₂CH₂CH₃ | H | CH₃ | CH₃ | CH | |
| H | SO₂NHCH₂CH₂CH₃ | H | OCH₃ | OCH₃ | N | 132–135 |
| H | SO₂NHCH₂CH₂CH₃ | H | OCH₃ | CH₃ | N | |
| H | SO₂NHCH₂CH₂CH₃ | H | OCH₂CH₃ | NHCH₃ | N | |
| H | SO₂NHCH₂CH₂CH₃ | CH₃ | OCH₃ | CH₃ | N | |
| 4-CH₃ | SO₂NHCH₂CH₂CH₃ | H | OCH₃ | OCH₃ | CH | |
| 4-OCH₃ | SO₂NHCH₂CH₂CH₃ | H | OCH₃ | OCH₃ | CH | |
| 6-CH₃ | SO₂NHCH₂CH₂CH₃ | H | OCH₃ | OCH₃ | CH | |
| 6-OCH₃ | SO₂NHCH₂CH₂CH₃ | H | OCH₃ | OCH₃ | CH | |
| 6-F | SO₂NHCH₂CH₂CH₃ | H | OCH₃ | OCH₃ | CH | |
| 6-Cl | SO₂NHCH₂CH₂CH₃ | H | OCH₃ | OCH₃ | CH | |
| H | SO₂NHCH(CH₃)₂ | H | OCH₃ | OCH₃ | CH | 164–166 |
| H | SO₂NHCH(CH₃)₂ | H | OCH₃ | CH₃ | CH₃ | |
| H | SO₂NHCH(CH₃)₂ | H | Cl | OCH₃ | CH | 153.5–156 |
| H | SO₂NHCH(CH₃)₂ | H | CH₃ | CH₃ | CH | |
| H | SO₂NHCH(CH₃)₂ | H | OCH₃ | OCH₃ | N | 149–152 |
| H | SO₂NHCH(CH₃)₂ | H | OCH₃ | OCH₃ | N | 149–151 |
| H | SO₂NHCH(CH₃)₂ | H | OCH₂CH₃ | NHCH₃ | N | |
| H | SO₂NHCH(CH₃)₂ | CH₃ | OCH₃ | CH₃ | N | 141–143 |
| 4-CH₃ | SO₂NHCH(CH₃)₂ | H | OCH₃ | OCH₃ | CH | |
| 4-OCH₃ | SO₂NHCH(CH₃)₂ | H | OCH₃ | OCH₃ | CH | |
| 6-CH₃ | SO₂NHCH(CH₃)₂ | H | OCH₃ | OCH₃ | CH | |
| 6-OCH₃ | SO₂NHCH(CH₃)₂ | H | OCH₃ | OCH₃ | CH | |
| 6-F | SO₂NHCH(CH₃)₂ | H | OCH₃ | OCH₃ | CH | |
| 6-Cl | SO₂NHCH(CH₃)₂ | H | OCH₃ | OCH₃ | CH | |
| H | SO₂NHcyclopropyl | H | OCH₃ | OCH₃ | CH | |
| H | SO₂NHcyclopropyl | H | OCH₃ | CH₃ | CH | |
| H | SO₂NHcyclopropyl | H | Cl | OCH₃ | CH | |
| H | SO₂NHcyclopropyl | H | CH₃ | CH₃ | CH | |
| H | SO₂NHcyclopropyl | H | OCH₃ | OCH₃ | N | |
| H | SO₂NHcyclopropyl | H | OCH₃ | CH₃ | N | |
| H | SO₂NHcyclopropyl | H | OCH₂CH₃ | NHCH₃ | N | |
| H | SO₂NHcyclopropyl | CH₃ | OCH₃ | CH₃ | N | |
| 4-CH₃ | SO₂NHcyclopropyl | H | OCH₃ | OCH₃ | CH | |

TABLE I-continued

General Formula 1

| R₁ | R₂ | R | X | Y | Z | m.p. (°C.) |
|---|---|---|---|---|---|---|
| 4-OCH₃ | SO₂NHcyclopropyl | H | OCH₃ | OCH₃ | CH | |
| 6-CH₃ | SO₂NHcyclopropyl | H | OCH₃ | OCH₃ | CH | |
| 6-OCH₃ | SO₂NHcyclopropyl | H | OCH₃ | OCH₃ | CH | |
| 6-F | SO₂NHcyclopropyl | H | OCH₃ | OCH₃ | CH | |
| 6-Cl | SO₂NHcyclopropyl | H | OCH₃ | OCH₃ | CH | |
| H | SO₂NHCH₂CH=CH₂ | H | OCH₃ | OCH₃ | CH | |
| H | SO₂NHCH₂CH=CH₂ | H | OCH₃ | CH₃ | CH | |
| H | SO₂NHCH₂CH=CH₂ | H | CL | OCH₃ | CH | |
| H | SO₂NHCH₂CH=CH₂ | H | CH₃ | CH₃ | CH | |
| H | SO₂NHCH₂CH=CH₂ | H | OCH₃ | OCH₃ | N | |
| H | SO₂NHCH₂CH=CH₂ | H | OCH₃ | CH₃ | N | |
| H | SO₂NHCH₂CH=CH₂ | H | OCH₂CH₃ | NHCH₃ | N | |
| H | SO₂NHCH₂CH=CH₂ | CH₃ | OCH₃ | CH₃ | N | |
| 4-CH₃ | SO₂NHCH₂CH=CH₂ | H | OCH₃ | OCH₃ | CH | |
| 4-OCH₃ | SO₂NHCH₂CH=CH₂ | H | OCH₃ | OCH₃ | CH | |
| 6-CH₃ | SO₂NHCH₂CH=CH₂ | H | OCH₃ | OCH₃ | CH | |
| 6-OCH₃ | SO₂NHCH₂CH=CH₂ | H | OCH₃ | OCH₃ | CH | |
| 6-F | SO₂NHCH₂CH=CH₂ | H | OCH₃ | OCH₃ | CH | |
| 6-Cl | SO₂NHCH₂CH=CH₂ | H | OCH₃ | OCH₃ | CH | |
| H | SO₂NHCH₂C≡CH | H | OCH₃ | OCH₃ | CH | |
| H | SO₂NHCH₂C≡CH | H | OCH₃ | CH₃ | CH | |
| H | SO₂NHCH₂C≡CH | H | Cl | OCH₃ | CH | |
| H | SO₂NHCH₂C≡CH | H | CH₃ | CH₃ | CH | |
| H | SO₂NHCH₂C≡CH | H | OCH₃ | OCH₃ | N | |
| H | SO₂NHCH₂C≡CH | H | OCH₃ | CH₃ | N | |
| H | SO₂NHCH₂C≡CH | H | OCH₂CH₃ | NHCH₃ | N | |
| H | SO₂NHCH₂C≡CH | CH₃ | OCH₃ | CH₃ | N | |
| 4-CH₃ | SO₂NHCH₂C≡CH | H | OCH₃ | OCH₃ | CH | |
| 4-OCH₃ | SO₂NHCH₂C≡CH | H | OCH₃ | OCH₃ | CH | |
| 6-CH₃ | SO₂NHCH₂C≡CH | H | OCH₃ | OCH₃ | CH | |
| 6-OCH | SO₂NHCH₂C≡CH | H | OCH₃ | OCH₃ | CH | |
| 6-F | SO₂NHCH₂C≡CH | H | OCH₃ | OCH₃ | CH | |
| 6-Cl | SO₂NHCH₂C≡CH | H | OCH₃ | OCH₃ | CH | |
| H | SO₂NHCH₂OCH₃ | H | OCH₃ | OCH₃ | CH | |
| H | SO₂NHCH₂OCH₃ | H | OCH₃ | CH₃ | CH | |
| H | SO₂NHCH₂OCH₃ | H | CL | OCH₃ | CH | |
| H | SO₂NHCH₂OCH₃ | H | CH₃ | CH₃ | CH | |
| H | SO₂NHCH₂OCH₃ | H | OCH₃ | OCH₃ | N | |
| H | SO₂NHCH₂OCH₃ | H | OCH₃ | CH₃ | N | |
| H | SO₂NHCH₂OCH₃ | H | OCH₂CH₃ | NHCH₃ | N | |
| H | SO₂NHCH₂OCH₃ | CH₃ | OCH₃ | CH₃ | N | |
| 4-CH₃ | SO₂NHCH₂OCH₃ | H | OCH₃ | OCH₃ | CH | |
| 4-OCH₃ | SO₂NHCH₂OCH₃ | H | OCH₃ | OCH₃ | CH | |
| 6-CH₃ | SO₂NHCH₂OCH₃ | H | OCH₃ | OCH₃ | CH | |
| 6-OCH₃ | SO₂NHCH₂OCH₃ | H | OCH₃ | OCH₃ | CH | |
| 6-F | SO₂NHCH₂OCH₃ | H | OCH₃ | OCH₃ | CH | |
| 6-Cl | SO₂NHCH₂OCH₃ | H | OCH₃ | OCH₃ | CH | |
| H | SO₂NHCH₂CF₃ | H | OCH₃ | OCH₃ | CH | |
| H | SO₂NHCH₂CF₃ | H | OCH₃ | CH₃ | CH | |
| H | SO₂NHCH₂CF₃ | H | Cl | OCH₃ | CH | |
| H | SO₂NHCH₂CF₃ | H | CH₃ | CH₃ | CH | |
| H | SO₂NHCH₂CF₃ | H | OCH₃ | OCH₃ | N | |
| H | SO₂NHCH₂CF₃ | H | OCH₃ | CH₃ | N | |
| H | SO₂NHCH₂CF₃ | H | OCH₂CH₃ | NHCH₃ | N | |
| H | SO₂NHCH₂CF₃ | CH₃ | OCH₃ | CH₃ | N | |
| 4-CH₃ | SO₂NHCH₂CF₃ | H | OCH₃ | OCH₃ | CH | |
| 4-OCH₃ | SO₂NHCH₂CF₃ | H | OCH₃ | OCH₃ | CH | |
| 6-CH₃ | SO₂NHCH₂CF₃ | H | OCH₃ | OCH₃ | CH | |
| 6-OCH | SO₂NHCH₂CF₃ | H | OCH₃ | OCH₃ | CH | |
| 6-F | SO₂NHCH₂CF₃ | H | OCH₃ | OCH₃ | CH | |
| 6-Cl | SO₂NHCH₂CN | H | OCH₃ | OCH₃ | CH | |
| H | SO₂NHCH₂CN | H | OCH₃ | OCH₃ | CH | |
| H | SO₂NHCH₂CN | H | OCH₃ | CH₃ | CH | |
| H | SO₂NHCH₂CN | H | CL | OCH₃ | CH | |
| H | SO₂NHCH₂CN | H | CH₃ | CH₃ | CH | |
| H | SO₂NHCH₂CN | H | OCH₃ | OCH₃ | N | |
| H | SO₂NHCH₂CN | H | OCH₃ | CH₃ | N | |
| H | SO₂NHCH₂CN | H | OCH₂CH₃ | NHCH₃ | N | |
| H | SO₂NHCH₂CN | CH₃ | OCH₃ | CH₃ | N | |
| 4-CH₃ | SO₂NHCH₂CN | H | OCH₃ | OCH₃ | CH | |
| 4-OCH₃ | SO₂NHCH₂CN | H | OCH₃ | OCH₃ | CH | |
| 6-CH₃ | SO₂NHCH₂CN | H | OCH₃ | OCH₃ | CH | |
| 6-OCH₃ | SO₂NHCH₂CN | H | OCH₃ | OCH₃ | CH | |
| 6-F | SO₂NHCH₂CN | H | OCH₃ | OCH₃ | CH | |
| 6-Cl | SO₂NHCH₂CN | H | OCH₃ | OCH₃ | CH | |
| H | SO₂N(CH₂CH=CH₂)₂ | H | OCH₃ | OCH₃ | CH | |
| H | SO₂N(CH₂CH=CH₂)₂ | H | OCH₃ | CH₃ | CH | |
| H | SO₂N(CH₂CH=CH₂)₂ | H | Cl | OCH₃ | CH | |
| H | SO₂N(CH₂CH=CH₂)₂ | H | CH₃ | CH₃ | CH | |
| H | SO₂N(CH₂CH=CH₂)₂ | H | OCH₃ | OCH₃ | N | |

TABLE I-continued

General Formula 1

| R₁ | R₂ | R | X | Y | Z | m.p. (°C.) |
|---|---|---|---|---|---|---|
| H | SO₂N(CH₂CH=CH₂)₂ | H | OCH₃ | CH₃ | N | |
| H | SO₂N(CH₂CH=CH₂)₂ | H | OCH₂CH₃ | NHCH₃ | N | |
| H | SO₂N(CH₂CH=CH₂)₂ | CH₃ | OCH₃ | CH₃ | N | |
| 4-CH₃ | SO₂N(CH₂CH=CH₂)₂ | H | OCH₃ | OCH₃ | CH | |
| 4-OCH₃ | SO₂N(CH₂CH=CH₂)₂ | H | OCH₃ | OCH₃ | CH | |
| 6-CH₃ | SO₂N(CH₂CH=CH₂)₂ | H | OCH₃ | OCH₃ | CH | |
| 6-OCH₃ | SO₂N(CH₂CH=CH₂)₂ | H | OCH₃ | OCH₃ | CH | |
| 6-F | SO₂N(CH₂CH=CH₂)₂ | H | OCH₃ | OCH₃ | CH | |
| 6-Cl | SO₂—pyrrolidino | H | OCH₃ | OCH₃ | CH | |
| H | SO₂—pyrrolidino | H | OCH₃ | OCH₃ | CH | |
| H | SO₂—pyrrolidino | H | OCH₃ | CH₃ | CH | |
| H | SO₂—pyrrolidino | H | Cl | OCH₃ | CH | |
| H | SO₂—pyrrolidino | H | CH₃ | CH₃ | CH | |
| H | SO₂—pyrrolidino | H | OCH₃ | OCH₃ | N | |
| H | SO₂—pyrrolidino | H | OCH₃ | CH₃ | N | |
| H | SO₂—pyrrolidino | H | OCH₂CH₃ | NHCH₃ | N | |
| H | SO₂—pyrrolidino | CH₃ | OCH₃ | CH₃ | N | |
| 4-CH₃ | SO₂—pyrrolidino | H | OCH₃ | OCH₃ | CH | |
| 4-OCH₃ | SO₂—pyrrolidino | H | OCH₃ | OCH₃ | CH | |
| 6-CH₃ | SO₂—pyrrolidino | H | OCH₃ | OCH₃ | CH | |
| 6-OCH₃ | SO₂—pyrrolidino | H | OCH₃ | OCH₃ | CH | |
| 6-F | SO₂—pyrrolidino | H | OCH₃ | OCH₃ | CH | |
| 6-Cl | SO₂—pyrrolidino | H | OCH₃ | OCH₃ | CH | |
| H | SO₂NHCH₂CH₂OCH₃ | H | OCH₃ | OCH₃ | CH | |
| H | SO₂NHCH₂CH₂OCH₃ | H | OCH₃ | CH₃ | CH | |
| H | SO₂NHCH₂CH₂OCH₃ | H | Cl | OCH₃ | CH | |
| H | SO₂NHCH₂CH₂OCH₃ | H | CH₃ | CH₃ | CH | |
| H | SO₂NHCH₂CH₂OCH₃ | H | OCH₃ | OCH₃ | N | |
| H | SO₂NHCH₂CH₂OCH₃ | H | OCH₃ | CH₃ | N | |
| H | SO₂NHCH₂CH₂OCH₃ | H | OCH₂CH₃ | NHCH₃ | N | |
| H | SO₂NHCH₂CH₂OCH₃ | CH₃ | OCH₃ | CH₃ | N | |
| 4-CH₃ | SO₂NHCH₂CH₂OCH₃ | H | OCH₃ | OCH₃ | CH | |
| 4-OCH₃ | SO₂NHCH₂CH₂OCH₃ | H | OCH₃ | OCH₃ | CH | |
| 6-CH₃ | SO₂NHCH₂CH₂OCH₃ | H | OCH₃ | OCH₃ | CH | |
| 6-OCH₃ | SO₂NHCH₂CH₂OCH₃ | H | OCH₃ | OCH₃ | CH | |
| 6-F | SO₂NHCH₂CH₂OCH₃ | H | OCH₃ | OCH₃ | CH | |
| 6-Cl | SO₂NHCH₂CH₂OCH₃ | H | OCH₃ | OCH₃ | CH | |
| H | SO₂—pyrrolidino | H | OCH₃ | OCH₃ | CH | 146–149 |
| H | SO₂—pyrrolidino | H | CH₃ | CH₃ | CH | 169–171 |
| 6-CH₂CH₃ | CO₂CH₃ | H | OCH₃ | OCH₃ | CH | |
| 6-CH₂CH₃ | CO₂CH₃ | H | OCH₃ | CH₃ | CH | |
| 6-CH₂CH₃ | CO₂CH₃ | H | Cl | OCH₃ | CH | |
| 6-CH₂CH₃ | CO₂CH₃ | H | CH₃ | CH₃ | CH | |
| 6-CH₂CH₃ | CO₂CH₃ | H | OCH₃ | OCH₃ | N | |
| 6-CH₂CH₃ | CO₂CH₃ | H | OCH₃ | CH₃ | N | |
| 6-CH₂CH₃ | CO₂CH₃ | H | OCH₂CH₃ | NHCH₃ | N | |
| 6-CH₂CH₃ | CO₂CH₃ | CH₃ | OCH₃ | CH₃ | N | |
| 6-OCH₃ | CO₂CH₃ | H | OCH₃ | OCH₃ | CH | 194–196 |
| 6-OCH₃ | CO₂CH₃ | H | OCH₃ | CH₃ | CH | 165–167 |
| 6-OCH₃ | CO₂CH₃ | H | Cl | OCH₃ | CH | 173–175 |
| 6-OCH₃ | CO₂CH₃ | H | CH₃ | CH₃ | CH | 138.5–145 |
| 6-OCH₃ | CO₂CH₃ | H | OCH₃ | OCH₃ | N | 173–176 |
| 6-OCH₃ | CO₂CH₃ | H | OCH₃ | CH₃ | N | 158–161 |
| 6-OCH₃ | CO₂CH₃ | H | OCH₂CH₃ | NHCH₃ | N | |
| 6-OCH₃ | CO₂CH₃ | CH₃ | OCH₃ | CH₃ | N | |
| 6-OCH₂CH₃ | CO₂CH₃ | H | OCH₃ | OCH₃ | CH | |
| 6-OCH₂CH₃ | CO₂CH₃ | H | OCH₃ | CH₃ | CH | |
| 6-OCH₂CH₃ | CO₂CH₃ | H | Cl | OCH₃ | CH | |
| 6-OCH₂CH₃ | CO₂CH₃ | H | CH₃ | CH₃ | CH | |
| 6-OCH₂CH₃ | CO₂CH₃ | H | OCH₃ | OCH₃ | N | |
| 6-OCH₂CH₃ | CO₂CH₃ | H | OCH₃ | CH₃ | N | |
| 6-OCH₂CH₃ | CO₂CH₃ | H | OCH₂CH₃ | NHCH₃ | N | |
| 6-OCH₂CH₃ | CO₂CH₃ | CH₃ | OCH₃ | CH₃ | N | |
| 6-OCF₃ | CO₂CH₃ | H | OCH₃ | OCH₃ | CH | |
| 6-OCF₃ | CO₂CH₃ | H | OCH₃ | CH₃ | CH | |
| 6-OCF₃ | CO₂CH₃ | H | Cl | OCH₃ | CH | |
| 6-OCF₃ | CO₂CH₃ | H | CH₃ | CH₃ | CH | |
| 6-OCF₃ | CO₂CH₃ | H | OCH₃ | OCH₃ | N | |
| 6-OCF₃ | CO₂CH₃ | H | OCH₃ | CH₃ | N | |
| 6-OCH₂CF₃ | CO₂CH₃ | H | OCH₃ | OCH₃ | CH | |
| 6-OCH₂CF₃ | CO₂CH₃ | H | OCH₃ | CH₃ | CH | |
| 6-OCH₂CF₃ | CO₂CH₃ | H | Cl | OCH₃ | CH | |
| 6-OCH₂CF₃ | CO₂CH₃ | H | CH₃ | CH₃ | CH | |
| 6-OCH₂CF₃ | CO₂CH₃ | H | OCH₃ | OCH₃ | N | |
| 6-OCH₂CF₃ | CO₂CH₃ | H | OCH₃ | CH₃ | N | |
| 6-OCH₂CF₃ | CO₂CH₃ | H | OCH₂CH₃ | NHCH₃ | N | |
| 6-OCH₂CF₃ | CO₂CH₃ | CH₃ | OCH₃ | CH₃ | N | |
| 6-OCF₃ | CO₂CH₃ | H | OCH₂CH₃ | NHCH₃ | N | |
| 6-OCF₃ | CO₂CH₃ | CH₃ | OCH₃ | CH₃ | N | |
| 6-OCF₂H | CO₂CH₃ | H | OCH₃ | OCH₃ | CH | |

TABLE I-continued

General Formula 1

| R₁ | R₂ | R | X | Y | Z | m.p. (°C.) |
|---|---|---|---|---|---|---|
| 6-OCF₂H | CO₂CH₃ | H | OCH₃ | CH₃ | CH | |
| 6-OCF₂H | CO₂CH₃ | H | Cl | OCH₃ | CH | |
| 6-OCF₂H | CO₂CH₃ | H | CH₃ | CH₃ | CH | |
| 6-OCF₂H | CO₂CH₃ | H | OCH₃ | OCH₃ | N | |
| 6-OCF₂H | CO₂CH₃ | H | OCH₃ | CH₃ | N | |
| 6-OCF₂H | CO₂CH₃ | H | OCH₂CH₃ | NHCH₃ | N | |
| 6-OCF₂H | CO₂CH₃ | CH₃ | OCH₃ | CH₃ | N | |
| 6-SCH₃ | CO₂CH₃ | H | OCH₃ | OCH₃ | CH | |
| 6-SCH₃ | CO₂CH₃ | H | OCH₃ | CH₃ | CH | |
| 6-SCH₃ | CO₂CH₃ | H | Cl | OCH₃ | CH | |
| 6-SCH₃ | CO₂CH₃ | H | CH₃ | CH₃ | CH | |
| 6-SCH₃ | CO₂CH₃ | H | OCH₃ | OCH₃ | N | |
| 6-SCH₃ | CO₂CH₃ | H | OCH₃ | CH₃ | N | |
| 6-SCH₃ | CO₂CH₃ | H | OCH₂CH₃ | NHCH₃ | N | |
| 6-SCH₃ | CO₂CH₃ | CH₃ | OCH₃ | CH₃ | N | |
| 6-SCH₂CH₃ | CO₂CH₃ | H | OCH₃ | OCH₃ | CH | |
| 6-SCH₂CH₃ | CO₂CH₃ | H | OCH₃ | CH₃ | CH | |
| 6-SCH₂CH₃ | CO₂CH₃ | H | Cl | OCH₃ | CH | |
| 6-SCH₂CH₃ | CO₂CH₃ | H | CH₃ | CH₃ | CH | |
| 6-SCH₂CH₃ | CO₂CH₃ | H | OCH₃ | OCH₃ | N | |
| 6-SCH₂CH₃ | CO₂CH₃ | H | OCH₃ | CH₃ | N | |
| 6-SCH₂CH₃ | CO₂CH₃ | H | OCH₂CH₃ | NHCH₃ | N | |
| 6-SCH₂CH₃ | CO₂CH₃ | CH₃ | OCH₃ | CH₃ | N | |
| 6-N(CH₃)₂ | CO₂CH₃ | H | OCH₃ | OCH₃ | CH | |
| 6-N(CH₃)₂ | CO₂CH₃ | H | OCH₃ | CH₃ | CH | |
| 6-N(CH₃)₂ | CO₂CH₃ | H | Cl | OCH₃ | CH | |
| 6-N(CH₃)₂ | CO₂CH₃ | H | CH₃ | CH₃ | CH | |
| 6-N(CH₃)₂ | CO₂CH₃ | H | OCH₃ | OCH₃ | N | |
| 6-N(CH₃)₂ | CO₂CH₃ | H | OCH₃ | CH₃ | N | |
| 6-N(CH₃)₂ | CO₂CH₃ | H | OCH₂CH₃ | NHCH₃ | N | |
| 6-N(CH₃)₂ | CO₂CH₃ | CH₃ | OCH₃ | CH₃ | N | |
| 6-NHCH₃ | CO₂CH₃ | H | OCH₃ | OCH₃ | CH | |
| 6-NHCH₃ | CO₂CH₃ | H | OCH₃ | CH₃ | CH | |
| 6-NHCH₃ | CO₂CH₃ | H | Cl | OCH₃ | CH | |
| 6-NHCH₃ | CO₂CH₃ | H | CH₃ | CH₃ | CH | |
| 6-NHCH₃ | CO₂CH₃ | H | OCH₃ | OCH₃ | N | |
| 6-NHCH₃ | CO₂CH₃ | H | OCH₃ | CH₃ | N | |
| 6-NHCH₃ | CO₂CH₃ | H | OCH₂CH₃ | NHCH₃ | N | |
| 6-NHCH₃ | CO₂CH₃ | CH₃ | OCH₃ | CH₃ | N | |
| 6-CH₂CH₃ | CO₂CH₂CH₃ | H | OCH₃ | OCH₃ | CH | |
| 6-CH₂CH₃ | CO₂CH₂CH₃ | H | OCH₃ | CH₃ | CH | |
| 6-CH₂CH₃ | CO₂CH₂CH₃ | H | Cl | OCH₃ | CH | |
| 6-CH₂CH₃ | CO₂CH₂CH₃ | H | CH₃ | CH₃ | CH | |
| 6-CH₂CH₃ | CO₂CH₂CH₃ | H | OCH₃ | OCH₃ | N | |
| 6-CH₂CH₃ | CO₂CH₂CH₃ | H | OCH₃ | CH₃ | N | |
| 6-CH₂CH₃ | CO₂CH₂CH₃ | H | OCH₂CH₃ | NHCH₃ | N | |
| 6-CH₂CH₃ | CO₂CH₂CH₃ | CH₃ | OCH₃ | CH₃ | N | |
| 6-OCH₃ | CO₂CH₂CH₃ | H | OCH₃ | OCH₃ | CH | 158–161 |
| 6-OCH₃ | CO₂CH₂CH₃ | H | OCH₃ | CH₃ | CH | 147–149 |
| 6-OCH₃ | CO₂CH₂CH₃ | H | Cl | OCH₃ | CH | 124–127 |
| 6-OCH₃ | CO₂CH₂CH₃ | H | CH₃ | CH₃ | CH | 149–151 |
| 6-OCH₃ | CO₂CH₂CH₃ | H | OCH₃ | OCH₃ | N | 164–165 |
| 6-OCH₃ | CO₂CH₂CH₃ | H | OCH₃ | CH₃ | N | 131–132 |
| 6-OCH₃ | CO₂CH₂CH₃ | H | OCH₂CH₃ | NHCH₃ | N | |
| 6-OCH₃ | CO₂CH₂CH₃ | CH₃ | OCH₃ | CH₃ | N | |
| 6-OCH₂CH₃ | CO₂CH₂CH₃ | H | OCH₃ | OCH₃ | CH | 152–154 |
| 6-OCH₂CH₃ | CO₂CH₂CH₃ | H | OCH₃ | CH₃ | CH | 134–135 |
| 6-OCH₂CH₃ | CO₂CH₂CH₃ | H | Cl | OCH₃ | CH | 153–160 |
| 6-OCH₂CH₃ | CO₂CH₂CH₃ | H | CH₃ | CH₃ | CH | 159–163 |
| 6-OCH₂CH₃ | CO₂CH₂CH₃ | H | OCH₃ | OCH₃ | N | 320–330 |
| 6-OCH₂CH₃ | CO₂CH₂CH₃ | H | OCH₃ | CH₃ | N | |
| 6-OCH₂CH₃ | CO₂CH₂CH₃ | H | OCH₂CH₃ | NHCH₃ | N | |
| 6-OCH₂CH₃ | CO₂CH₂CH₃ | CH₃ | OCH₃ | CH₃ | N | |
| 6-OCH₂CF₃ | CO₂CH₂CH₃ | H | OCH₃ | OCH₃ | CH | 173–175 |
| 6-OCH₂CF₃ | CO₂CH₂CH₃ | H | OCH₃ | CH₃ | CH | 166–167 |
| 6-OCH₂CF₃ | CO₂CH₂CH₃ | H | Cl | OCH₃ | CH | 150–152 |
| 6-OCH₂CF₃ | CO₂CH₂CH₃ | H | CH₃ | CH₃ | CH | 142–144 |
| 6-OCH₂CF₃ | CO₂CH₂CH₃ | H | OCH₃ | OCH₃ | N | 138–141 |
| 6-OCH₂CF₃ | CO₂CH₂CH₃ | H | OCH₃ | CH₃ | N | 122–126 |
| 6-OCH₂CF₃ | CO₂CH₂CH₃ | H | OCH₂CH₃ | NHCH₃ | N | |
| 6-OCH₂CF₃ | CO₂CH₂CH₃ | CH₃ | OCH₃ | CH₃ | N | |
| 6-OCF₃ | CO₂CH₂CH₃ | H | OCH₃ | OCH₃ | CH | |
| 6-OCF₃ | CO₂CH₂CH₃ | H | OCH₃ | CH₃ | CH | |
| 6-OCF₃ | CO₂CH₂CH₃ | H | Cl | OCH₃ | CH | |
| 6-OCF₃ | CO₂CH₂CH₃ | H | CH₃ | CH₃ | CH | |
| 6-OCF₃ | CO₂CH₂CH₃ | H | OCH₃ | OCH₃ | N | |
| 6-OCF₃ | CO₂CH₂CH₃ | H | OCH₃ | CH₃ | N | |
| 6-OCF₃ | CO₂CH₂CH₃ | H | OCH₂CH₃ | NHCH₃ | N | |
| 6-OCF₃ | CO₂CH₂CH₃ | CH₃ | OCH₃ | CH₃ | N | |
| 6-OCF₂H | CO₂CH₂CH₃ | H | OCH₃ | OCH₃ | CH | |

TABLE I-continued

General Formula 1

| R₁ | R₂ | R | X | Y | Z | m.p. (°C.) |
|---|---|---|---|---|---|---|
| 6-OCF₂H | CO₂CH₂CH₃ | H | OCH₃ | OCH₃ | CH | |
| 6-OCF₂H | CO₂CH₂CH₃ | H | Cl | OCH₃ | CH | |
| 6-OCF₂H | CO₂CH₂CH₃ | H | CH₃ | CH₃ | CH | |
| 6-OCF₂H | CO₂CH₂CH₃ | H | OCH₃ | OCH₃ | N | |
| 6-OCF₂H | CO₂CH₂CH₃ | H | OCH₃ | CH₃ | N | |
| 6-OCF₂H | CO₂CH₂CH₃ | H | OCH₂CH₃ | NHCH₃ | N | |
| 6-OCF₂H | CO₂CH₂CH₃ | CH₃ | OCH₃ | CH₃ | N | |
| 6-SCH₃ | CO₂CH₂CH₃ | H | OCH₃ | OCH₃ | CH | |
| 6-SCH₃ | CO₂CH₂CH₃ | H | OCH₃ | CH₃ | CH | |
| 6-SCH₃ | CO₂CH₂CH₃ | H | Cl | OCH₃ | CH | |
| 6-SCH₃ | CO₂CH₂CH₃ | H | CH₃ | CH₃ | CH | |
| 6-SCH₃ | CO₂CH₂CH₃ | H | OCH₃ | OCH₃ | N | |
| 6-SCH₃ | CO₂CH₂CH₃ | H | OCH₃ | CH₃ | N | |
| 6-SCH₃ | CO₂CH₂CH₃ | H | OCH₂CH₃ | NHCH₃ | N | |
| 6-SCH₃ | CO₂CH₂CH₃ | CH₃ | OCH₃ | CH₃ | N | |
| 6-SCH₂CH₃ | CO₂CH₂CH₃ | H | OCH₃ | OCH₃ | CH | |
| 6-SCH₂CH₃ | CO₂CH₂CH₃ | H | OCH₃ | CH₃ | CH | |
| 6-SCH₂CH₃ | CO₂CH₂CH₃ | H | Cl | OCH₃ | CH | |
| 6-SCH₂CH₃ | CO₂CH₂CH₃ | H | CH₃ | CH₃ | CH | |
| 6-SCH₂CH₃ | CO₂CH₂CH₃ | H | OCH₃ | OCH₃ | N | |
| 6-SCH₂CH₃ | CO₂CH₂CH₃ | H | OCH₃ | CH₃ | N | |
| 6-SCH₂CH₃ | CO₂CH₂CH₃ | H | OCH₂CH₃ | NHCH₃ | N | |
| 6-SCH₂CH₃ | CO₂CH₂CH₃ | CH₃ | OCH₃ | CH₃ | N | |
| 6-N(CH₃)₂ | CO₂CH₂CH₃ | H | OCH₃ | OCH₃ | CH | 147–149 |
| 6-N(CH₃)₂ | CO₂CH₂CH₃ | H | OCH₃ | CH₃ | CH | 149–150 |
| 6-N(CH₃)₂ | CO₂CH₂CH₃ | H | Cl | OCH₃ | CH | 150–151 |
| 6-N(CH₃)₂ | CO₂CH₂CH₃ | H | CH₃ | CH₃ | CH | 172–175 |
| 6-N(CH₃)₂ | CO₂CH₂CH₃ | H | OCH₃ | OCH₃ | N | 152–153 |
| 6-N(CH₃)₂ | CO₂CH₂CH₃ | H | OCH₃ | CH₃ | N | 148–150 |
| 6-N(CH₃)₂ | CO₂CH₂CH₃ | H | OCH₂CH₃ | NHCH₃ | N | |
| 6-N(CH₃)₂ | CO₂CH₂CH₃ | CH₃ | OCH₃ | CH₃ | N | |
| 6-NHCH₃ | CO₂CH₂CH₃ | H | OCH₃ | OCH₃ | CH | |
| 6-NHCH₃ | CO₂CH₂CH₃ | H | OCH₃ | CH₃ | CH | |
| 6-NHCH₃ | CO₂CH₂CH₃ | H | Cl | OCH₃ | CH | |
| 6-NHCH₃ | CO₂CH₂CH₃ | H | CH₃ | CH₃ | CH | |
| 6-NHCH₃ | CO₂CH₂CH₃ | H | OCH₃ | OCH₃ | N | |
| 6-NHCH₃ | CO₂CH₂CH₃ | H | OCH₃ | CH₃ | N | |
| 6-NHCH₃ | CO₂CH₂CH₃ | H | OCH₂CH₃ | NHCH₃ | N | |
| 6-NHCH₃ | CO₂CH₂CH₃ | CH₃ | OCH₃ | CH₃ | N | |
| H | CO₂CH₂CH₂OH | H | OCH₃ | OCH₃ | CH | |
| H | CO₂CH₂CH₂OH | H | OCH₃ | CH₃ | CH | |
| H | CO₂CH₂CH₂OH | H | Cl | OCH₃ | CH | |
| H | CO₂CH₂CH₂OH | H | CH₃ | CH₃ | CH | |
| H | CO₂CH₂CH₂OH | H | OCH₃ | OCH₃ | N | |
| H | CO₂CH₂CH₂OH | H | OCH₃ | CH₃ | N | |
| H | CO₂CH₂CH₂OH | H | OCH₂CH₃ | NHCH₃ | N | |
| H | CO₂CH₂CH₂OH | CH₃ | OCH₃ | CH₃ | N | |
| 4-CH₃ | CO₂CH₂CH₂OH | H | OCH₃ | OCH₃ | CH | |
| 4-OCH₃ | CO₂CH₂CH₂OH | H | OCH₃ | OCH₃ | CH | |
| 6-CH₃ | CO₂CH₂CH₂OH | H | OCH₃ | OCH₃ | CH | |
| 6-OCH₃ | CO₂CH₂CH₂OH | H | OCH₃ | OCH₃ | CH | |
| 6-F | CO₂CH₂CH₂OH | H | OCH₃ | OCH₃ | CH | |
| 6-Cl | CO₂CH₂CH₂OH | H | OCH₃ | OCH₃ | CH | |
| H | CO₂CH₂CH₂CN | H | OCH₃ | OCH₃ | CH | |
| H | CO₂CH₂CH₂CN | H | OCH₃ | CH₃ | CH | |
| H | CO₂CH₂CH₂CN | H | Cl | OCH₃ | CH | |
| H | CO₂CH₂CH₂CN | H | CH₃ | CH₃ | CH | |
| H | CO₂CH₂CH₂CN | H | OCH₃ | OCH₃ | N | |
| H | CO₂CH₂CH₂CN | H | OCH₃ | CH₃ | N | |
| H | CO₂CH₂CH₂CN | H | OCH₂CH₃ | NHCH₃ | N | |
| H | CO₂CH₂CH₂CN | CH₃ | OCH₃ | CH₃ | N | |
| 4-CH₃ | CO₂CH₂CH₂CN | H | OCH₃ | OCH₃ | CH | |
| 4-OCH₃ | CO₂CH₂CH₂CN | H | OCH₃ | OCH₃ | CH | |
| 6-CH₃ | CO₂CH₂CH₂CN | H | OCH₃ | OCH₃ | CH | |
| 6-OCH₃ | CO₂CH₂CH₂CN | H | OCH₃ | OCH₃ | CH | |
| 6-F | CO₂CH₂CH₂CN | H | OCH₃ | OCH₃ | CH | |
| 6-Cl | CO₂CH₂CH₂CN | H | OCH₃ | OCH₃ | CH | |
| H | CO₂CH₂CH₂OSO₂CH₃ | H | OCH₃ | OCH₃ | CH | |
| H | CO₂CH₂CH₂OSO₂CH₃ | H | OCH₃ | CH₃ | CH | |
| H | CO₂CH₂CH₂OSO₂CH₃ | H | Cl | OCH₃ | CH | |
| H | CO₂CH₂CH₂OSO₂CH₃ | H | CH₃ | CH₃ | CH | |
| H | CO₂CH₂CH₂OSO₂CH₃ | H | OCH₃ | OCH₃ | N | |
| H | CO₂CH₂CH₂OSO₂CH₃ | H | OCH₃ | CH₃ | N | |
| H | CO₂CH₂CH₂OSO₂CH₃ | H | OCH₂CH₃ | NHCH₃ | N | |
| H | CO₂CH₂CH₂OSO₂CH₃ | CH₃ | OCH₃ | CH₃ | N | |
| 4-CH₃ | CO₂CH₂CH₂OSO₂CH₃ | H | OCH₃ | OCH₃ | CH | |
| 4-OCH₃ | CO₂CH₂CH₂OSO₂CH₃ | H | OCH₃ | OCH₃ | CH | |
| 6-CH₃ | CO₂CH₂CH₂OSO₂CH₃ | H | OCH₃ | OCH₃ | CH | |
| 6-OCH₃ | CO₂CH₂CH₂OSO₂CH₃ | H | OCH₃ | OCH₃ | CH | |
| 6-F | CO₂CH₂CH₂OSO₂CH₃ | H | OCH₃ | OCH₃ | CH | |

TABLE I-continued

General Formula 1

| $R_1$ | $R_2$ | R | X | Y | Z | m.p. (°C.) |
|---|---|---|---|---|---|---|
| 6-Cl | $CO_2CH_2CH_2OSO_2CH_3$ | H | $OCH_3$ | $OCH_3$ | CH | |
| H | $CO_2CH_2CH_2OSO_2CF_3$ | H | $OCH_3$ | $OCH_3$ | CH | |
| H | $CO_2CH_2CH_2OSO_2CF_3$ | H | $OCH_3$ | $CH_3$ | CH | |
| H | $CO_2CH_2CH_2OSO_2CF_3$ | H | Cl | $OCH_3$ | CH | |
| H | $CO_2CH_2CH_2OSO_2CF_3$ | H | $CH_3$ | $CH_3$ | CH | |
| H | $CO_2CH_2CH_2OSO_2CF_3$ | H | $OCH_3$ | $OCH_3$ | N | |
| H | $CO_2CH_2CH_2OSO_2CF_3$ | H | $OCH_3$ | $CH_3$ | N | |
| H | $CO_2CH_2CH_2OSO_2CF_3$ | H | $OCH_2CH_3$ | $NHCH_3$ | N | |
| H | $CO_2CH_2CH_2OSO_2CF_3$ | $CH_3$ | $OCH_3$ | $CH_3$ | N | |
| 4-$CH_3$ | $CO_2CH_2CH_2OSO_2CF_3$ | H | $OCH_3$ | $OCH_3$ | CH | |
| 4-$OCH_3$ | $CO_2CH_2CH_2OSO_2CF_3$ | H | $OCH_3$ | $OCH_3$ | CH | |
| 6-$CH_3$ | $CO_2CH_2CH_2OSO_2CF_3$ | H | $OCH_3$ | $OCH_3$ | CH | |
| 6-$OCH_3$ | $CO_2CH_2CH_2OSO_2CF_3$ | H | $OCH_3$ | $OCH_3$ | CH | |
| 6-F | $CO_2CH_2CH_2OSO_2CF_3$ | H | $OCH_3$ | $OCH_3$ | CH | |
| 6-Cl | $CO_2CH_2CH_2OSO_2CF_3$ | H | $OCH_3$ | $OCH_3$ | CH | |
| H | $CO_2CH_2CF_3$ | H | $OCH_3$ | $OCH_3$ | CH | |
| H | $CO_2CH_2CF_3$ | H | $OCH_3$ | $CH_3$ | CH | |
| H | $CO_2CH_2CF_3$ | H | Cl | $OCH_3$ | CH | |
| H | $CO_2CH_2CF_3$ | H | $CH_3$ | $CH_3$ | CH | |
| H | $CO_2CH_2CF_3$ | H | $OCH_3$ | $OCH_3$ | N | |
| H | $CO_2CH_2CF_3$ | H | $OCH_3$ | $CH_3$ | N | |
| H | $CO_2CH_2CF_3$ | H | $OCH_2CH_3$ | $NHCH_3$ | N | |
| H | $CO_2CH_2CF_3$ | $CH_3$ | $OCH_3$ | $CH_3$ | N | |
| 4-$CH_3$ | $CO_2CH_2CF_3$ | H | $OCH_3$ | $OCH_3$ | CH | |
| 4-$OCH_3$ | $CO_2CH_2CF_3$ | H | $OCH_3$ | $OCH_3$ | CH | |
| 6-$CH_3$ | $CO_2CH_2CF_3$ | H | $OCH_3$ | $OCH_3$ | CH | |
| 6-$OCH_3$ | $CO_2CH_2CF_3$ | H | $OCH_3$ | $OCH_3$ | CH | |
| 6-F | $CO_2CH_2CF_3$ | H | $OCH_3$ | $OCH_3$ | CH | |
| 6-Cl | $CO_2CH_2CF_3$ | H | $OCH_3$ | $OCH_3$ | CH | |
| H | $CO_2CH_2C\equiv CH$ | H | $OCH_3$ | $OCH_3$ | CH | |
| H | $CO_2CH_2C\equiv CH$ | H | $OCH_3$ | $CH_3$ | CH | |
| H | $CO_2CH_2C\equiv CH$ | H | Cl | $OCH_3$ | CH | |
| H | $CO_2CH_2C\equiv CH$ | H | $CH_3$ | $CH_3$ | CH | |
| H | $CO_2CH_2C\equiv CH$ | H | $OCH_3$ | $OCH_3$ | N | |
| H | $CO_2CH_2C\equiv CH$ | H | $OCH_3$ | $CH_3$ | N | |
| H | $CO_2CH_2C\equiv CH$ | H | $OCH_2CH_3$ | $NHCH_3$ | N | |
| H | $CO_2CH_2C\equiv CH$ | $CH_3$ | $OCH_3$ | $CH_3$ | N | |
| 4-$CH_3$ | $CO_2CH_2C\equiv CH$ | H | $OCH_3$ | $OCH_3$ | CH | |
| 4-$OCH_3$ | $CO_2CH_2C\equiv CH$ | H | $OCH_3$ | $OCH_3$ | CH | |
| 6-$CH_3$ | $CO_2CH_2C\equiv CH$ | H | $OCH_3$ | $OCH_3$ | CH | |
| 6-$OCH_3$ | $CO_2CH_2C\equiv CH$ | H | $OCH_3$ | $OCH_3$ | CH | |
| 6-F | $CO_2CH_2C\equiv CH$ | H | $OCH_3$ | $OCH_3$ | CH | |
| 6-Cl | $CO_2CH_2C\equiv CH$ | H | $OCH_3$ | $OCH_3$ | CH | |
| H | $CO_2CH_2CH_2CH_2Cl$ | H | $OCH_3$ | $OCH_3$ | CH | |
| H | $CO_2CH_2CH_2CH_2Cl$ | H | $OCH_3$ | $CH_3$ | CH | |
| H | $CO_2CH_2CH_2CH_2Cl$ | H | Cl | $OCH_3$ | CH | |
| H | $CO_2CH_2CH_2CH_2Cl$ | H | $CH_3$ | $CH_3$ | CH | |
| H | $CO_2CH_2CH_2CH_2Cl$ | H | $OCH_3$ | $OCH_3$ | N | |
| H | $CO_2CH_2CH_2CH_2Cl$ | H | $OCH_3$ | $CH_3$ | N | |
| H | $CO_2CH_2CH_2CH_2Cl$ | H | $OCH_2CH_3$ | $NHCH_3$ | N | |
| H | $CO_2CH_2CH_2CH_2Cl$ | $CH_3$ | $OCH_3$ | $CH_3$ | N | |
| 4-$CH_3$ | $CO_2CH_2CH_2CH_2Cl$ | H | $OCH_3$ | $OCH_3$ | CH | |
| 4-$OCH_3$ | $CO_2CH_2CH_2CH_2Cl$ | H | $OCH_3$ | $OCH_3$ | CH | |
| 6-$CH_3$ | $CO_2CH_2CH_2CH_2Cl$ | H | $OCH_3$ | $OCH_3$ | CH | |
| 6-$OCH_3$ | $CO_2CH_2CH_2CH_2Cl$ | H | $OCH_3$ | $OCH_3$ | CH | |
| 6-F | $CO_2CH_2CH_2CH_2Cl$ | H | $OCH_3$ | $OCH_3$ | CH | |
| 6-Cl | $CO_2CH_2CH_2CH_2Cl$ | H | $OCH_3$ | $OCH_3$ | CH | |
| H | $CO_2CH_2CH_2SCH_3$ | H | $OCH_3$ | $OCH_3$ | CH | |
| H | $CO_2CH_2CH_2SCH_3$ | H | $OCH_3$ | $CH_3$ | CH | |
| H | $CO_2CH_2CH_2SCH_3$ | H | Cl | $OCH_3$ | CH | |
| H | $CO_2CH_2CH_2SCH_3$ | H | $CH_3$ | $CH_3$ | CH | |
| H | $CO_2CH_2CH_2SCH_3$ | H | $OCH_3$ | $OCH_3$ | N | |
| H | $CO_2CH_2CH_2SCH_3$ | H | $OCH_3$ | $CH_3$ | N | |
| H | $CO_2CH_2CH_2SCH_3$ | H | $OCH_2CH_3$ | $NHCH_3$ | N | |
| H | $CO_2CH_2CH_2SCH_3$ | $CH_3$ | $OCH_3$ | $CH_3$ | N | |
| 4-$CH_3$ | $CO_2CH_2CH_2SCH_3$ | H | $OCH_3$ | $OCH_3$ | CH | |
| 4-$OCH_3$ | $CO_2CH_2CH_2SCH_3$ | H | $OCH_3$ | $OCH_3$ | CH | |
| 6-$CH_3$ | $CO_2CH_2CH_2SCH_3$ | H | $OCH_3$ | $OCH_3$ | CH | |
| 6-$OCH_3$ | $CO_2CH_2CH_2SCH_3$ | H | $OCH_3$ | $OCH_3$ | CH | |
| 6-F | $CO_2CH_2CH_2SCH_3$ | H | $OCH_3$ | $OCH_3$ | CH | |
| 6-Cl | $CO_2CH_2CH_2SCH_3$ | H | $OCH_3$ | $OCH_3$ | CH | |
| H | $CO_2CH_2$—cyclopropyl | H | $OCH_3$ | $OCH_3$ | CH | 143–145 |
| H | $CO_2CH_2$—cyclopropyl | H | Cl | $OCH_3$ | CH | 124–128 |
| H | $CO_2CH_2$—cyclopropyl | H | $CH_3$ | $CH_3$ | CH | 134–138 |
| H | $CO_2CH_2$—cyclopropyl | H | $OCH_3$ | $OCH_3$ | N | 154–161 |

TABLE II

General Formula 2

| R₁ | R₃ | R | X | Y | Z | m.p. (°C.) |
|---|---|---|---|---|---|---|
| H | SO₂NHCH₃ | H | OCH₃ | OCH₃ | CH | |
| H | SO₂NHCH₃ | H | OCH₃ | CH₃ | CH | |
| H | SO₂NHCH₃ | H | Cl | OCH₃ | CH | |
| H | SO₂NHCH₃ | H | CH₃ | CH₃ | CH | |
| H | SO₂NHCH₃ | H | OCH₃ | OCH₃ | N | |
| H | SO₂NHCH₃ | H | OCH₃ | CH₃ | N | |
| H | SO₂NHCH₃ | H | OCH₂CH₃ | NHCH₃ | N | |
| H | SO₂NHCH₃ | CH₃ | OCH₃ | CH₃ | N | |
| 4-CH₃ | SO₂NHCH₃ | H | OCH₃ | OCH₃ | CH | |
| 4-Cl | SO₂NHCH₃ | H | OCH₃ | OCH₃ | CH | |
| 6-CH₃ | SO₂NHCH₃ | H | OCH₃ | OCH₃ | CH | |
| 6-OCH₃ | SO₂NHCH₃ | H | OCH₃ | OCH₃ | CH | |
| 6-F | SO₂NHCH₃ | H | OCH₃ | OCH₃ | CH | |
| 6-Cl | SO₂NHCH₃ | H | OCH₃ | OCH₃ | CH | |
| H | SO₂NHCH₂CH₃ | H | OCH₃ | OCH₃ | CH | |
| H | SO₂NHCH₂CH₃ | H | OCH₃ | CH₃ | CH | |
| H | SO₂NHCH₂CH₃ | H | Cl | OCH₃ | CH | |
| H | SO₂NHCH₂CH₃ | H | CH₃ | CH₃ | CH | |
| H | SO₂NHCH₂CH₃ | H | OCH₃ | OCH₃ | N | |
| H | SO₂NHCH₂CH₃ | H | OCH₃ | CH₃ | N | |
| H | SO₂NHCH₂CH₃ | H | OCH₂CH₃ | NHCH₃ | N | |
| H | SO₂NHCH₂CH₃ | CH₃ | OCH₃ | CH₃ | N | |
| 4-CH₃ | SO₂NHCH₂CH₃ | H | OCH₃ | OCH₃ | CH | |
| 4-Cl | SO₂NHCH₂CH₃ | H | OCH₃ | OCH₃ | CH | |
| 6-CH₃ | SO₂NHCH₂CH₃ | H | OCH₃ | OCH₃ | CH | |
| 6-OCH₃ | SO₂NHCH₂CH₃ | H | OCH₃ | OCH₃ | CH | |
| 6-F | SO₂NHCH₂CH₃ | H | OCH₃ | OCH₃ | CH | |
| 6-Cl | SO₂NHCH₂CH₃ | H | OCH₃ | OCH₃ | CH | |
| H | SO₂NHCH₂CH₂CH₃ | H | OCH₃ | OCH₃ | CH | |
| H | SO₂NHCH₂CH₂CH₃ | H | OCH₃ | CH₃ | CH | |
| H | SO₂NHCH₂CH₂CH₃ | H | Cl | OCH₃ | CH | |
| H | SO₂NHCH₂CH₂CH₃ | H | CH₃ | CH₃ | CH | |
| H | SO₂NHCH₂CH₂CH₃ | H | OCH₃ | OCH₃ | N | |
| H | SO₂NHCH₂CH₂CH₃ | H | OCH₃ | CH₃ | N | |
| H | SO₂NHCH₂CH₂CH₃ | H | OCH₂CH₃ | NHCH₃ | N | |
| H | SO₂NHCH₂CH₂CH₃ | CH₃ | OCH₃ | CH₃ | N | |
| 4-CH₃ | SO₂NHCH₂CH₂CH₃ | H | OCH₃ | OCH₃ | CH | |
| 4-Cl | SO₂NHCH₂CH₂CH₃ | H | OCH₃ | OCH₃ | CH | |
| 6-CH₃ | SO₂NHCH₂CH₂CH₃ | H | OCH₃ | OCH₃ | CH | |
| 6-OCH₃ | SO₂NHCH₂CH₂CH₃ | H | OCH₃ | OCH₃ | CH | |
| 6-F | SO₂NHCH₂CH₂CH₃ | H | OCH₃ | OCH₃ | CH | |
| 6-Cl | SO₂NHCH₂CH₂CH₃ | H | OCH₃ | OCH₃ | CH | |
| H | SO₂NHCH(CH₃)₂ | H | OCH₃ | OCH₃ | CH | |
| H | SO₂NHCH(CH₃)₂ | H | OCH₃ | CH₃ | CH | |
| H | SO₂NHCH(CH₃)₂ | H | Cl | OCH₃ | CH | |
| H | SO₂NHCH(CH₃)₂ | H | CH₃ | CH₃ | CH | |
| H | SO₂NHCH(CH₃)₂ | H | OCH₃ | OCH₃ | N | |
| H | SO₂NHCH(CH₃)₂ | H | OCH₃ | CH₃ | N | |
| H | SO₂NHCH(CH₃)₂ | H | OCH₂CH₃ | NHCH₃ | N | |
| H | SO₂NHCH(CH₃)₂ | CH₃ | OCH₃ | CH₃ | N | |
| 4-CH₃ | SO₂NHCH(CH₃)₂ | H | OCH₃ | OCH₃ | CH | |
| 4-Cl | SO₂NHCH(CH₃)₂ | H | OCH₃ | OCH₃ | CH | |
| 6-CH₃ | SO₂NHCH(CH₃)₂ | H | OCH₃ | OCH₃ | CH | |
| 6-OCH₃ | SO₂NHCH(CH₃)₂ | H | OCH₃ | OCH₃ | CH | |
| 6-F | SO₂NHCH(CH₃)₂ | H | OCH₃ | OCH₃ | CH | |
| 6-Cl | SO₂NHCH(CH₃)₂ | H | OCH₃ | OCH₃ | CH | |
| H | SO₂NH—cyclopropyl | H | OCH₃ | OCH₃ | CH | |
| H | SO₂NH—cyclopropyl | H | OCH₃ | CH₃ | CH | |
| H | SO₂NH—cyclopropyl | H | Cl | OCH₃ | CH | |
| H | SO₂NH—cyclopropyl | H | CH₃ | CH₃ | CH | |
| H | SO₂NH—cyclopropyl | H | OCH₃ | OCH₃ | N | |
| H | SO₂NH—cyclopropyl | H | OCH₃ | CH₃ | N | |
| H | SO₂NH—cyclopropyl | H | OCH₂CH₃ | NHCH₃ | N | |
| H | SO₂NH—cyclopropyl | CH₃ | OCH₃ | CH₃ | N | |
| 4-CH₃ | SO₂NH—cyclopropyl | H | OCH₃ | OCH₃ | CH | |
| 4-Cl | SO₂NH—cyclopropyl | H | OCH₃ | OCH₃ | CH | |
| 6-CH₃ | SO₂NH—cyclopropyl | H | OCH₃ | OCH₃ | CH | |
| 6-OCH₃ | SO₂NH—cyclopropyl | H | OCH₃ | OCH₃ | CH | |
| 6-F | SO₂NH—cyclopropyl | H | OCH₃ | OCH₃ | CH | |
| 6-Cl | SO₂NH—cyclopropyl | H | OCH₃ | OCH₃ | CH | |
| H | SO₂NHCH₂CH=CH₂ | H | OCH₃ | OCH₃ | CH | |
| H | SO₂NHCH₂CH=CH₂ | H | OCH₃ | CH₃ | CH | |
| H | SO₂NHCH₂CH=CH₂ | H | Cl | OCH₃ | CH | |
| H | SO₂NHCH₂CH=CH₂ | H | CH₃ | CH₃ | CH | |
| H | SO₂NHCH₂CH=CH₂ | H | OCH₃ | OCH₃ | N | |
| H | SO₂NHCH₂CH=CH₂ | H | OCH₃ | CH₃ | N | |
| H | SO₂NHCH₂CH=CH₂ | H | OCH₂CH₃ | NHCH₃ | N | |
| H | SO₂NHCH₂CH=CH₂ | CH₃ | OCH₃ | CH₃ | N | |
| 4-CH₃ | SO₂NHCH₂CH=CH₂ | H | OCH₃ | OCH₃ | CH | |
| 4-Cl | SO₂NHCH₂CH=CH₂ | H | OCH₃ | OCH₃ | CH | |

TABLE II-continued

| | | General Formula 2 | | | | |
|---|---|---|---|---|---|---|
| R₁ | R₃ | R | X | Y | Z | m.p. (°C.) |
| 6-CH₃ | SO₂NHCH₂CH=CH₂ | H | OCH₃ | OCH₃ | CH | |
| 6-OCH₃ | SO₂NHCH₂CH=CH₂ | H | OCH₃ | OCH₃ | CH | |
| 6-F | SO₂NHCH₂CH=CH₂ | H | OCH₃ | OCH₃ | CH | |
| 6-Cl | SO₂NHCH₂CH=CH₂ | H | OCH₃ | OCH₃ | CH | |
| H | SO₂NHCH₂CF₃ | H | OCH₃ | OCH₃ | CH | |
| H | SO₂NHCH₂CF₃ | H | OCH₃ | CH₃ | CH | |
| H | SO₂NHCH₂CF₃ | H | Cl | OCH₃ | CH | |
| H | SO₂NHCH₂CF₃ | H | CH₃ | CH₃ | CH | |
| H | SO₂NHCH₂CF₃ | H | OCH₃ | OCH₃ | N | |
| H | SO₂NHCH₂CF₃ | H | OCH₃ | CH₃ | N | |
| H | SO₂NHCH₂CF₃ | H | OCH₂CH₃ | NHCH₃ | N | |
| H | SO₂NHCH₂CF₃ | CH₃ | OCH₃ | CH₃ | N | |
| 4-CH₃ | SO₂NHCH₂CF₃ | H | OCH₃ | OCH₃ | CH | |
| 4-Cl | SO₂NHCH₂CF₃ | H | OCH₃ | OCH₃ | CH | |
| 6-CH₃ | SO₂NHCH₂CF₃ | H | OCH₃ | OCH₃ | CH | |
| 6-OCH₃ | SO₂NHCH₂CF₃ | H | OCH₃ | OCH₃ | CH | |
| 6-F | SO₂NHCH₂CF₃ | H | OCH₃ | OCH₃ | CH | |
| 6-Cl | SO₂NHCH₂CF₃ | H | OCH₃ | OCH₃ | CH | |
| H | SO₂NHCH₂CN | H | OCH₃ | OCH₃ | CH | |
| H | SO₂NHCH₂CN | H | OCH₃ | CH₃ | CH | |
| H | SO₂NHCH₂CN | H | Cl | OCH₃ | CH | |
| H | SO₂NHCH₂CN | H | CH₃ | CH₃ | CH | |
| H | SO₂NHCH₂CN | H | OCH₃ | OCH₃ | N | |
| H | SO₂NHCH₂CN | H | OCH₃ | CH₃ | N | |
| H | SO₂NHCH₂CN | H | OCH₂CH₃ | NHCH₃ | N | |
| H | SO₂NHCH₂CN | CH₃ | OCH₃ | CH₃ | N | |
| 4-CH₃ | SO₂NHCH₂CN | H | OCH₃ | OCH₃ | CH | |
| 4-Cl | SO₂NHCH₂CN | H | OCH₃ | OCH₃ | CH | |
| 6-CH₃ | SO₂NHCH₂CN | H | OCH₃ | OCH₃ | CH | |
| 6-OCH₃ | SO₂NHCH₂CN | H | OCH₃ | OCH₃ | CH | |
| 6-F | SO₂NHCH₂CN | H | OCH₃ | OCH₃ | CH | |
| 6-Cl | SO₂NHCH₂CN | H | OCH₃ | OCH₃ | CH | |
| H | SO₂N(CH₂CH=CH₂)₂ | H | OCH₃ | OCH₃ | CH | |
| H | SO₂N(CH₂CH=CH₂)₂ | H | OCH₃ | CH₃ | CH | |
| H | SO₂N(CH₂CH=CH₂)₂ | H | Cl | OCH₃ | CH | |
| H | SO₂N(CH₂CH=CH₂)₂ | H | CH₃ | CH₃ | CH | |
| H | SO₂N(CH₂CH=CH₂)₂ | H | OCH₃ | OCH₃ | N | |
| H | SO₂N(CH₂CH=CH₂)₂ | H | OCH₃ | CH₃ | N | |
| H | SO₂N(CH₂CH=CH₂)₂ | H | OCH₂CH₃ | NHCH₃ | N | |
| H | SO₂N(CH₂CH=CH₂)₂ | CH₃ | OCH₃ | CH₃ | N | |
| 4-CH₃ | SO₂N(CH₂CH=CH₂)₂ | H | OCH₃ | OCH₃ | CH | |
| 4-Cl | SO₂N(CH₂CH=CH₂)₂ | H | OCH₃ | OCH₃ | CH | |
| 6-CH₃ | SO₂N(CH₂CH=CH₂)₂ | H | OCH₃ | OCH₃ | CH | |
| 6-OCH₃ | SO₂N(CH₂CH=CH₂)₂ | H | OCH₃ | OCH₃ | CH | |
| 6-F | SO₂N(CH₂CH=CH₂)₂ | H | OCH₃ | OCH₃ | CH | |
| 6-Cl | SO₂N(CH₂CH=CH₂)₂ | H | OCH₃ | OCH₃ | CH | |
| H | SO₂—pyrrolidino | H | OCH₃ | OCH₃ | CH | |
| H | SO₂—pyrrolidino | H | OCH₃ | CH₃ | CH | |
| H | SO₂—pyrrolidino | H | Cl | OCH₃ | CH | |
| H | SO₂—pyrrolidino | H | CH₃ | CH₃ | CH | |
| H | SO₂—pyrrolidino | H | OCH₃ | OCH₃ | N | |
| H | SO₂—pyrrolidino | H | OCH₃ | CH₃ | N | |
| H | SO₂—pyrrolidino | H | OCH₂CH₃ | NHCH₃ | N | |
| H | SO₂—pyrrolidino | CH₃ | OCH₃ | CH₃ | N | |
| 4-CH₃ | SO₂—pyrrolidino | H | OCH₃ | OCH₃ | CH | |
| 4-Cl | SO₂—pyrrolidino | H | OCH₃ | OCH₃ | CH | |
| 6-CH₃ | SO₂—pyrrolidino | H | OCH₃ | OCH₃ | CH | |
| 6-OCH₃ | SO₂—pyrrolidino | H | OCH₃ | OCH₃ | CH | |
| 6-F | SO₂—pyrrolidino | H | OCH₃ | OCH₃ | CH | |
| 6-Cl | SO₂—pyrrolidino | H | OCH₃ | OCH₃ | CH | |
| H | SO₂NHCH₂CH₂OCH₃ | H | OCH₃ | OCH₃ | CH | |
| H | SO₂NHCH₂CH₂OCH₃ | H | OCH₃ | CH₃ | CH | |
| H | SO₂NHCH₂CH₂OCH₃ | H | Cl | OCH₃ | CH | |
| H | SO₂NHCH₂CH₂OCH₃ | H | CH₃ | CH₃ | CH | |
| H | SO₂NHCH₂CH₂OCH₃ | H | OCH₃ | OCH₃ | N | |
| H | SO₂NHCH₂CH₂OCH₃ | H | OCH₃ | CH₃ | N | |
| H | SO₂NHCH₂CH₂OCH₃ | H | OCH₂CH₃ | NHCH₃ | N | |
| H | SO₂NHCH₂CH₂OCH₃ | CH₃ | OCH₃ | CH₃ | N | |
| 4-CH₃ | SO₂NHCH₂CH₂OCH₃ | H | OCH₃ | OCH₃ | CH | |
| 4-Cl | SO₂NHCH₂CH₂OCH₃ | H | OCH₃ | OCH₃ | CH | |
| 6-CH₃ | SO₂NHCH₂CH₂OCH₃ | H | OCH₃ | OCH₃ | CH | |
| 6-OCH₃ | SO₂NHCH₂CH₂OCH₃ | H | OCH₃ | OCH₃ | CH | |
| 6-F | SO₂NHCH₂CH₂OCH₃ | H | OCH₃ | OCH₃ | CH | |
| 6-Cl | SO₂NHCH₂CH₂OCH₃ | H | OCH₃ | OCH₃ | CH | |
| H | SO₂NH₂ | H | OCH₃ | OCH₃ | CH | |
| H | SO₂NH₂ | H | OCH₃ | CH₃ | CH | |
| H | SO₂NH₂ | H | Cl | OCH₃ | CH | |
| H | SO₂NH₂ | H | CH₃ | CH₃ | CH | |
| H | SO₂NH₂ | H | OCH₃ | OCH₃ | N | |
| H | SO₂NH₂ | H | OCH₃ | CH₃ | N | |

TABLE II-continued

General Formula 2

| $R_1$ | $R_3$ | R | X | Y | Z | m.p. (°C.) |
|---|---|---|---|---|---|---|
| H | $SO_2NH_2$ | H | $OCH_2CH_3$ | $NHCH_3$ | N | |
| H | $SO_2NH_2$ | $CH_3$ | $OCH_3$ | $CH_3$ | N | |
| 4-$CH_3$ | $SO_2NH_2$ | H | $OCH_3$ | $OCH_3$ | CH | |
| 4-Cl | $SO_2NH_2$ | H | $OCH_3$ | $OCH_3$ | CH | |
| 6-$CH_3$ | $SO_2NH_2$ | H | $OCH_3$ | $OCH_3$ | CH | |
| 6-$OCH_3$ | $SO_2NH_2$ | H | $OCH_3$ | $OCH_3$ | CH | |
| 6-F | $SO_2NH_2$ | H | $OCH_3$ | $OCH_3$ | CH | |
| 6-Cl | $SO_2NH_2$ | H | $OCH_3$ | $OCH_3$ | CH | |
| H | $CO_2CH_2CH_2OH$ | H | $OCH_3$ | $OCH_3$ | CH | |
| H | $CO_2CH_2CH_2OH$ | H | $OCH_3$ | $CH_3$ | CH | |
| H | $CO_2CH_2CH_2OH$ | H | Cl | $OCH_3$ | CH | |
| H | $CO_2CH_2CH_2OH$ | H | $CH_3$ | $CH_3$ | CH | |
| H | $CO_2CH_2CH_2OH$ | H | $OCH_3$ | $OCH_3$ | N | |
| H | $CO_2CH_2CH_2OH$ | H | $OCH_3$ | $CH_3$ | N | |
| H | $CO_2CH_2CH_2OH$ | H | $OCH_2CH_3$ | $NHCH_3$ | N | |
| H | $CO_2CH_2CH_2OH$ | $CH_3$ | $OCH_3$ | $CH_3$ | N | |
| 4-$CH_3$ | $CO_2CH_2CH_2OH$ | H | $OCH_3$ | $OCH_3$ | CH | |
| 4-Cl | $CO_2CH_2CH_2OH$ | H | $OCH_3$ | $OCH_3$ | CH | |
| 6-$CH_3$ | $CO_2CH_2CH_2OH$ | H | $OCH_3$ | $OCH_3$ | CH | |
| 6-$OCH_3$ | $CO_2CH_2CH_2OH$ | H | $OCH_3$ | $OCH_3$ | CH | |
| 6-F | $CO_2CH_2CH_2OH$ | H | $OCH_3$ | $OCH_3$ | CH | |
| 6-Cl | $CO_2CH_2CH_2OH$ | H | $OCO_3$ | $OCH_3$ | CH | |
| H | $CO_2CH_2CH_2OH$ | H | $OCH_3$ | $OCH_3$ | CH | |
| H | $CO_2CH_2CH_2OH$ | H | $OCH_3$ | $CH_3$ | CH | |
| H | $CO_2CH_2CH_2OH$ | H | Cl | $OCH_3$ | CH | |
| H | $CO_2CH_2CH_2OH$ | H | $CH_3$ | $CH_3$ | CH | |
| H | $CO_2CH_2CH_2OH$ | H | $OCH_3$ | $OCH_3$ | N | |
| H | $CO_2CH_2CH_2OH$ | H | $OCH_3$ | $CH_3$ | N | |
| H | $CO_2CH_2CH_2OH$ | H | $OCH_2CH_3$ | $NHCH_3$ | N | |
| H | $CO_2CH_2CH_2OH$ | $CH_3$ | $OCH_3$ | $CH_3$ | N | |
| 4-$CH_3$ | $CO_2CH_2CH_2OH$ | H | $OCH_3$ | $OCH_3$ | CH | |
| 4-Cl | $CO_2CH_2CH_2OH$ | H | $OCH_3$ | $OCH_3$ | CH | |
| 6-$CH_3$ | $CO_2CH_2CH_2OH$ | H | $OCH_3$ | $OCH_3$ | CH | |
| 6-$OCH_3$ | $CO_2CH_2CH_2OH$ | H | $OCH_3$ | $OCH_3$ | CH | |
| 6-F | $CO_2CH_2CH_2OH$ | H | $OCH_3$ | $OCH_3$ | CH | |
| 6-Cl | $CO_2CH_2CH_2OH$ | H | $OCH_3$ | $OCH_3$ | CH | |
| H | $CO_2CH_2CH_2OSO_2CH_3$ | H | $OCH_3$ | $OCH_3$ | CH | |
| H | $CO_2CH_2CH_2OSO_2CH_3$ | H | $OCH_3$ | $CH_3$ | CH | |
| H | $CO_2CH_2CH_2OSO_2CH_3$ | H | Cl | $OCH_3$ | CH | |
| H | $CO_2CH_2CH_2OSO_2CH_3$ | H | $CH_3$ | $CH_3$ | CH | |
| H | $CO_2CH_2CH_2OSO_2CH_3$ | H | $OCH_3$ | $OCH_3$ | N | |
| H | $CO_2CH_2CH_2OSO_2CH_3$ | H | $OCH_3$ | $CH_3$ | N | |
| H | $CO_2CH_2CH_2OSO_2CH_3$ | H | $OCH_2CH_3$ | $NHCH_3$ | N | |
| H | $CO_2CH_2CH_2OSO_2CH_3$ | $CH_3$ | $OCH_3$ | $CH_3$ | N | |
| 4-$CH_3$ | $CO_2CH_2CH_2OSO_2CH_3$ | H | $OCH_3$ | $OCH_3$ | CH | |
| 4-Cl | $CO_2CH_2CH_2OSO_2CH_3$ | H | $OCH_3$ | $OCH_3$ | CH | |
| 6-$CH_3$ | $CO_2CH_2CH_2OSO_2CH_3$ | H | $OCH_3$ | $OCH_3$ | CH | |
| 6-$OCH_3$ | $CO_2CH_2CH_2OSO_2CH_3$ | H | $OCH_3$ | $OCH_3$ | CH | |
| 6-F | $CO_2CH_2CH_2OSO_2CH_3$ | H | $OCH_3$ | $OCH_3$ | CH | |
| 6-Cl | $CO_2CH_2CH_2OSO_2CH_3$ | H | $OCH_3$ | $OCH_3$ | CH | |
| H | $CO_2CH_2CF_3$ | H | $OCH_3$ | $OCH_3$ | CH | |
| H | $CO_2CH_2CF_3$ | H | $OCH_3$ | $CH_3$ | CH | |
| H | $CO_2CH_2CF_3$ | H | Cl | $OCH_3$ | CH | |
| H | $CO_2CH_2CF_3$ | H | $CH_3$ | $CH_3$ | CH | |
| H | $CO_2CH_2CF_3$ | H | $OCH_3$ | $OCH_3$ | N | |
| H | $CO_2CH_2CF_3$ | H | $OCH_3$ | $CH_3$ | N | |
| H | $CO_2CH_2CF_3$ | H | $OCH_2CH_3$ | $NHCH_3$ | N | |
| H | $CO_2CH_2CF_3$ | $CH_3$ | $OCH_3$ | $CH_3$ | N | |
| 4-$CH_3$ | $CO_2CH_2CF_3$ | H | $OCH_3$ | $OCH_3$ | CH | |
| 4-Cl | $CO_2CH_2CF_3$ | H | $OCH_3$ | $OCH_3$ | CH | |
| 6-$CH_3$ | $CO_2CH_2CF_3$ | H | $OCH_3$ | $OCH_3$ | CH | |
| 6-$OCH_3$ | $CO_2CH_2CF_3$ | H | $OCH_3$ | $OCH_3$ | CH | |
| 6-F | $CO_2CH_2CF_3$ | H | $OCH_3$ | $OCH_3$ | CH | |
| 6-Cl | $CO_2CH_2CF_3$ | H | $OCH_3$ | $OCH_3$ | CH | |

TABLE III

General Formula 2

| $R_1$ | $R_3$ | R | X | Y | Z | m.p. (°C.) |
|---|---|---|---|---|---|---|
| H | $SO_2N(OCH_3)CH_3$ | H | $OCH_3$ | $OCH_3$ | CH | |
| H | $SO_2N(OCH_3)CH_3$ | H | $OCH_3$ | $CH_3$ | CH | |
| H | $SO_2N(OCH_3)CH_3$ | H | Cl | $OCH_3$ | CH | |
| H | $SO_2N(OCH_3)CH_3$ | H | $CH_3$ | $CH_3$ | CH | |
| H | $SO_2N(OCH_3)CH_3$ | H | $OCH_3$ | $OCH_3$ | N | |
| H | $SO_2N(OCH_3)CH_3$ | H | $OCH_3$ | $CH_3$ | N | |
| H | $SO_2N(OCH_3)CH_3$ | H | $OCH_2CH_3$ | $NHCH_3$ | N | |
| H | $SO_2N(OCH_3)CH_3$ | $CH_3$ | $OCH_3$ | $CH_3$ | N | |
| 2-Cl | $SO_2N(OCH_3)CH_3$ | H | $OCH_3$ | $OCH_3$ | CH | |

TABLE III-continued

General Formula 2

| R₁ | R₃ | R | X | Y | Z | m.p. (°C.) |
|---|---|---|---|---|---|---|
| 2-F | SO₂N(OCH₃)CH₃ | H | OCH₃ | OCH₃ | CH | |
| 6-CH₃ | SO₂N(OCH₃)CH₃ | H | OCH₃ | OCH₃ | CH | |
| 6-OCH₃ | SO₂N(OCH₃)CH₃ | H | OCH₃ | OCH₃ | CH | |
| 6-F | SO₂N(OCH₃)CH₃ | H | OCH₃ | OCH₃ | CH | |
| 6-Cl | SO₂N(OCH₃)CH₃ | H | OCH₃ | OCH₃ | CH | |
| H | SO₂NHCH₃ | H | OCH₃ | OCH₃ | CH | |
| H | SO₂NHCH₃ | H | OCH₃ | CH₃ | CH | |
| H | SO₂NHCH₃ | H | Cl | OCH₃ | CH | |
| H | SO₂NHCH₃ | H | CH₃ | CH₃ | CH | |
| H | SO₂NHCH₃ | H | OCH₃ | OCH₃ | N | |
| H | SO₂NHCH₃ | H | OCH₃ | CH₃ | N | |
| H | SO₂NHCH₃ | H | OCH₂CH₃ | NHCH₃ | N | |
| H | SO₂NHCH₃ | CH₃ | OCH₃ | CH₃ | N | |
| 2-Cl | SO₂NHCH₃ | H | OCH₃ | OCH₃ | CH | |
| 2-F | SO₂NHCH₃ | H | OCH₃ | OCH₃ | CH | |
| 6-CH₃ | SO₂NHCH₃ | H | OCH₃ | OCH₃ | CH | |
| 6-OCH₃ | SO₂NHCH₃ | H | OCH₃ | OCH₃ | CH | |
| 6-F | SO₂NHCH₃ | H | OCH₃ | OCH₃ | CH | |
| 6-Cl | SO₂NHCH₃ | H | OCH₃ | OCH₃ | CH | |
| H | SO₂NHCH₂CH₃ | H | OCH₃ | OCH₃ | CH | |
| H | SO₂NHCH₂CH₃ | H | OCH₃ | CH₃ | CH | |
| H | SO₂NHCH₂CH₃ | H | Cl | OCH₃ | CH | |
| H | SO₂NHCH₂CH₃ | H | CH₃ | CH₃ | CH | |
| H | SO₂NHCH₂CH₃ | H | OCH₃ | OCH₃ | N | |
| H | SO₂NHCH₂CH₃ | H | OCH₃ | CH₃ | N | |
| H | SO₂NHCH₂CH₃ | H | OCH₂CH₃ | NHCH₃ | N | |
| H | SO₂NHCH₂CH₃ | CH₃ | OCH₃ | CH₃ | N | |
| 2-Cl | SO₂NHCH₂CH₃ | H | OCH₃ | OCH₃ | CH | |
| 2-F | SO₂NHCH₂CH₃ | H | OCH₃ | OCH₃ | CH | |
| 6-CH₃ | SO₂NHCH₂CH₃ | H | OCH₃ | OCH₃ | CH | |
| 6-OCH₃ | SO₂NHCH₂CH₃ | H | OCH₃ | OCH₃ | CH | |
| 6-F | SO₂NHCH₂CH₃ | H | OCH₃ | OCH₃ | CH | |
| 6-Cl | SO₂NHCH₂CH₃ | H | OCH₃ | OCH₃ | CH | |
| H | SO₂NHCH₂CH₂OCH₃ | H | OCH₃ | OCH₃ | CH | |
| H | SO₂NHCH₂CH₂OCH₃ | H | OCH₃ | CH₃ | CH | |
| H | SO₂NHCH₂CH₂OCH₃ | H | Cl | OCH₃ | CH | |
| H | SO₂NHCH₂CH₂OCH₃ | H | CH₃ | CH₃ | CH | |
| H | SO₂NHCH₂CH₂OCH₃ | H | OCH₃ | OCH₃ | N | |
| H | SO₂NHCH₂CH₂OCH₃ | H | OCH₃ | CH₃ | N | |
| H | SO₂NHCH₂CH₂OCH₃ | H | OCH₂CH₃ | NHCH₃ | N | |
| H | SO₂NHCH₂CH₂OCH₃ | CH₃ | OCH₃ | CH₃ | N | |
| 2-Cl | SO₂NHCH₂CH₂OCH₃ | H | OCH₃ | OCH₃ | CH | |
| 2-F | SO₂NHCH₂CH₂OCH₃ | H | OCH₃ | OCH₃ | CH | |
| 6-CH₃ | SO₂NHCH₂CH₂OCH₃ | H | OCH₃ | OCH₃ | CH | |
| 6-OCH₃ | SO₂NHCH₂CH₂OCH₃ | H | OCH₃ | OCH₃ | CH | |
| 6-F | SO₂NHCH₂CH₂OCH₃ | H | OCH₃ | OCH₃ | CH | |
| 6-Cl | SO₂NHCH₂CH₂OCH₃ | H | OCH₃ | OCH₃ | CH | |
| H | CO₂CH₂CH₂OH | H | OCH₃ | OCH₃ | CH | |
| H | CO₂CH₂CH₂OH | H | OCH₃ | CH₃ | CH | |
| H | CO₂CH₂CH₂OH | H | Cl | OCH₃ | CH | |
| H | CO₂CH₂CH₂OH | H | CH₃ | CH₃ | CH | |
| H | CO₂CH₂CH₂OH | H | OCH₃ | OCH₃ | N | |
| H | CO₂CH₂CH₂OH | H | OCH₃ | CH₃ | N | |
| H | CO₂CH₂CH₂OH | H | OCH₂CH₃ | NHCH₃ | N | |
| H | CO₂CH₂CH₂OH | CH₃ | OCH₃ | CH₃ | N | |
| 2-Cl | CO₂CH₂CH₂OH | H | OCH₃ | OCH₃ | CH | |
| 2-F | CO₂CH₂CH₂OH | H | OCH₃ | OCH₃ | CH | |
| 6-CH₃ | CO₂CH₂CH₂OH | H | OCH₃ | OCH₃ | CH | |
| 6-OCH₃ | CO₂CH₂CH₂OH | H | OCH₃ | OCH₃ | CH | |
| 6-F | CO₂CH₂CH₂OH | H | OCH₃ | OCH₃ | CH | |
| 6-Cl | CO₂CH₂CH₂OH | H | OCH₃ | OCH₃ | CH | |
| H | CO₂CH₂CH₂OH | H | OCH₃ | OCH₃ | CH | |
| H | CO₂CH₂CH₂OH | H | OCH₃ | CH₃ | CH | |
| H | CO₂CH₂CH₂OH | H | Cl | OCH₃ | CH | |
| H | CO₂CH₂CH₂OH | H | CH₃ | CH₃ | CH | |
| H | CO₂CH₂CH₂OH | H | OCH₃ | OCH₃ | N | |
| H | CO₂CH₂CH₂OH | H | OCH₃ | CH₃ | N | |
| H | CO₂CH₂CH₂OH | H | OCH₃ | OCH₃ | N | |
| H | CO₂CH₂CH₂OH | CH₃ | OCH₃ | CH₃ | N | |
| 2-Cl | CO₂CH₂CH₂OH | H | OCH₃ | OCH₃ | CH | |
| 2-F | CO₂CH₂CH₂OH | H | OCH₃ | OCH₃ | CH | |
| 6-CH₃ | CO₂CH₂CH₂OH | H | OCH₃ | OCH₃ | CH | |
| 6-OCH₃ | CO₂CH₂CH₂OH | H | OCH₃ | OCH₃ | CH | |
| 6-F | CO₂CH₂CH₂OH | H | OCH₃ | OCH₃ | CH | |
| 6-Cl | CO₂CH₂CH₂OH | H | OCH₃ | OCH₃ | CH | |
| H | CO₂CH₂CH₂OSO₂CH₃ | H | OCH₃ | OCH₃ | CH | |
| H | CO₂CH₂CH₂OSO₂CH₃ | H | OCH₃ | CH₃ | CH | |
| H | CO₂CH₂CH₂OSO₂CH₃ | H | Cl | OCH₃ | CH | |
| H | CO₂CH₂CH₂OSO₂CH₃ | H | CH₃ | CH₃ | CH | |
| H | CO₂CH₂CH₂OSO₂CH₃ | H | OCH₃ | OCH₃ | N | |

TABLE III-continued

General Formula 2

| $R_1$ | $R_3$ | R | X | Y | Z | m.p. (°C.) |
|---|---|---|---|---|---|---|
| H | $CO_2CH_2CH_2OSO_2CH_3$ | H | $OCH_3$ | $CH_3$ | N | |
| H | $CO_2CH_2CH_2OSO_2CH_3$ | H | $OCH_2CH_3$ | $NHCH_3$ | N | |
| H | $CO_2CH_2CH_2OSO_2CH_3$ | $CH_3$ | $OCH_3$ | $CH_3$ | N | |
| 2-Cl | $CO_2CH_2CH_2OSO_2CH_3$ | H | $OCH_3$ | $OCH_3$ | CH | |
| 2-F | $CO_2CH_2CH_2OSO_2CH_3$ | H | $OCH_3$ | $OCH_3$ | CH | |
| 6-$CH_3$ | $CO_2CH_2CH_2OSO_2CH_3$ | H | $OCH_3$ | $OCH_3$ | CH | |
| 6-$OCH_3$ | $CO_2CH_2CH_2OSO_2CH_3$ | H | $OCH_3$ | $OCH_3$ | CH | |
| 6-F | $CO_2CH_2CH_2OSO_2CH_3$ | H | $OCH_3$ | $OCH_3$ | CH | |
| 6-Cl | $CO_2CH_2CH_2OSO_2CH_3$ | H | $OCH_3$ | $OCH_3$ | CH | |
| H | $CO_2CH_2CF_3$ | H | $OCH_3$ | $OCH_3$ | CH | |
| H | $CO_2CH_2CF_3$ | H | $OCH_3$ | $CH_3$ | CH | |
| H | $CO_2CH_2CF_3$ | H | Cl | $OCH_3$ | CH | |
| H | $CO_2CH_2CF_3$ | H | $CH_3$ | $CH_3$ | CH | |
| H | $CO_2CH_2CF_3$ | H | $OCH_3$ | $OCH_3$ | N | |
| H | $CO_2CH_2CF_3$ | H | $OCH_3$ | $CH_3$ | N | |
| H | $CO_2CH_2CF_3$ | H | $OCH_3$ | $OCH_3$ | N | |
| H | $CO_2CH_2CF_3$ | $CH_3$ | $OCH_3$ | $CH_3$ | N | |
| 2-Cl | $CO_2CH_2CF_3$ | H | $OCH_3$ | $OCH_3$ | CH | |
| 2-F | $CO_2CH_2CF_3$ | H | $OCH_3$ | $OCH_3$ | CH | |
| 6-$CH_3$ | $CO_2CH_2CF_3$ | H | $OCH_3$ | $OCH_3$ | CH | |
| 6-$OCH_3$ | $CO_2CH_2CF_3$ | H | $OCH_3$ | $OCH_3$ | CH | |
| 6-F | $CO_2CH_2CF_3$ | H | $OCH_3$ | $OCH_3$ | CH | |
| 6-Cl | $CO_2CH_2CF_3$ | H | $OCH_3$ | $OCH_3$ | CH | |

TABLE IV

General Formula 4

| $R_1$ | $R_5$ | R | X | Y | Z | m.p.(°C.) |
|---|---|---|---|---|---|---|
| H | $SO_2N(OCH_3)CH_3$ | H | $OCH_3$ | $OCH_3$ | CH | |
| H | $SO_2N(OCH_3)CH_3$ | H | $OCH_3$ | $CH_3$ | CH | |
| H | $SO_2N(OCH_3)CH_3$ | H | Cl | $OCH_3$ | CH | |
| H | $SO_2N(OCH_3)CH_3$ | H | $CH_3$ | $CH_3$ | CH | |
| H | $SO_2N(OCH_3)CH_3$ | H | $OCH_3$ | $OCH_3$ | N | |
| H | $SO_2N(OCH_3)CH_3$ | H | $OCH_3$ | $CH_3$ | N | |
| H | $SO_2N(OCH_3)CH_3$ | H | $OCH_2CH_3$ | $NHCH_3$ | N | |
| H | $SO_2N(OCH_3)CH_3$ | $CH_3$ | $OCH_3$ | $CH_3$ | N | |
| 5-$CH_3$ | $SO_2N(OCH_3)CH_3$ | H | $OCH_3$ | $OCH_3$ | CH | |
| 5-$OCH_3$ | $SO_2N(OCH_3)CH_3$ | H | $OCH_3$ | $OCH_3$ | CH | |
| 6-$CH_3$ | $SO_2N(OCH_3)CH_3$ | H | $OCH_3$ | $OCH_3$ | CH | |
| 6-$OCH_3$ | $SO_2N(OCH_3)CH_3$ | H | $OCH_3$ | $OCH_3$ | CH | |
| 6-F | $SO_2N(OCH_3)CH_3$ | H | $OCH_3$ | $OCH_3$ | CH | |
| 6-Cl | $SO_2N(OCH_3)CH_3$ | H | $OCH_3$ | $OCH_3$ | CH | |
| H | $SO_2NHCH_3$ | H | $OCH_3$ | $OCH_3$ | CH | |
| H | $SO_2NHCH_3$ | H | $OCH_3$ | $CH_3$ | CH | |
| H | $SO_2NHCH_3$ | H | Cl | $OCH_3$ | CH | |
| H | $SO_2NHCH_3$ | H | $CH_3$ | $CH_3$ | CH | |
| H | $SO_2NHCH_3$ | H | $OCH_3$ | $OCH_3$ | N | |
| H | $SO_2NHCH_3$ | H | $OCH_3$ | $CH_3$ | N | |
| H | $SO_2NHCH_3$ | H | $OCH_2CH_3$ | $NHCH_3$ | N | |
| H | $SO_2NHCH_3$ | $CH_3$ | $OCH_3$ | $CH_3$ | N | |
| 5-$CH_3$ | $SO_2NHCH_3$ | H | $OCH_3$ | $OCH_3$ | CH | |
| 5-$OCH_3$ | $SO_2NHCH_3$ | H | $OCH_3$ | $OCH_3$ | CH | |
| 6-$CH_3$ | $SO_2NHCH_3$ | H | $OCH_3$ | $OCH_3$ | CH | |
| 6-$OCH_3$ | $SO_2NHCH_3$ | H | $OCH_3$ | $OCH_3$ | CH | |
| 6-F | $SO_2NHCH_3$ | H | $OCH_3$ | $OCH_3$ | CH | |
| 6-Cl | $SO_2NHCH_3$ | H | $OCH_3$ | $OCH_3$ | CH | |
| H | $SO_2NHCH_2CH_3$ | H | $OCH_3$ | $OCH_3$ | CH | |
| H | $SO_2NHCH_2CH_3$ | H | $OCH_3$ | $CH_3$ | CH | |
| H | $SO_2NHCH_2CH_3$ | H | Cl | $OCH_3$ | CH | |
| H | $SO_2NHCH_2CH_3$ | H | $CH_3$ | $CH_3$ | CH | |
| H | $SO_2NHCH_2CH_3$ | H | $OCH_3$ | $OCH_3$ | N | |
| H | $SO_2NHCH_2CH_3$ | H | $OCH_3$ | $CH_3$ | N | |
| H | $SO_2NHCH_2CH_3$ | H | $OCH_2CH_3$ | $NHCH_3$ | N | |
| H | $SO_2NHCH_2CH_3$ | $CH_3$ | $OCH_3$ | $CH_3$ | N | |
| 5-$CH_3$ | $SO_2NHCH_2CH_3$ | H | $OCH_3$ | $OCH_3$ | CH | |
| 5-$OCH_3$ | $SO_2NHCH_2CH_3$ | H | $OCH_3$ | $OCH_3$ | CH | |
| 6-$CH_3$ | $SO_2NHCH_2CH_3$ | H | $OCH_3$ | $OCH_3$ | CH | |
| 6-$OCH_3$ | $SO_2NHCH_2CH_3$ | H | $OCH_3$ | $OCH_3$ | CH | |
| 6-F | $SO_2NHCH_2CH_3$ | H | $OCH_3$ | $OCH_3$ | CH | |
| 6-Cl | $SO_2NHCH_2CH_3$ | H | $OCH_3$ | $OCH_3$ | CH | |
| H | $CO_2CH_2CH_2OH$ | H | $OCH_3$ | $OCH_3$ | CH | |
| H | $CO_2CH_2CH_2OH$ | H | $OCH_3$ | $CH_3$ | CH | |
| H | $CO_2CH_2CH_2OH$ | H | Cl | $OCH_3$ | CH | |
| H | $CO_2CH_2CH_2OH$ | H | $CH_3$ | $CH_3$ | CH | |
| H | $CO_2CH_2CH_2OH$ | H | $OCH_3$ | $OCH_3$ | N | |
| H | $CO_2CH_2CH_2OH$ | H | $OCH_3$ | $CH_3$ | N | |
| H | $CO_2CH_2CH_2OH$ | H | $OCH_2CH_3$ | $NHCH_3$ | N | |
| H | $CO_2CH_2CH_2OH$ | $CH_3$ | $OCH_3$ | $CH_3$ | N | |

TABLE IV-continued

General Formula 4

| R₁ | R₅ | R | X | Y | Z | m.p.(°C.) |
|---|---|---|---|---|---|---|
| 5-CH₃ | CO₂CH₂CH₂OH | H | OCH₃ | OCH₃ | CH | |
| 5-OCH₃ | CO₂CH₂CH₂OH | H | OCH₃ | OCH₃ | CH | |
| 6-CH₃ | CO₂CH₂CH₂OH | H | OCH₃ | OCH₃ | CH | |
| 6-OCH₃ | CO₂CH₂CH₂OH | H | OCH₃ | OCH₃ | CH | |
| 6-OCH₃ | CO₂CH₂CH₂OH | H | OCH₃ | OCH₃ | CH | |
| 6-F | CO₂CH₂CH₂OH | H | OCH₃ | OCH₃ | CH | |
| 6-Cl | CO₂CH₂CH₂OH | H | OCH₃ | OCH₃ | CH | |
| H | CO₂CH₂CH₂CN | H | OCH₃ | OCH₃ | CH | |
| H | CO₂CH₂CH₂CN | H | OCH₃ | CH₃ | CH | |
| H | CO₂CH₂CH₂CN | H | Cl | OCH₃ | CH | |
| H | CO₂CH₂CH₂CN | H | CH₃ | CH₃ | CH | |
| H | CO₂CH₂CH₂CN | H | OCH₃ | OCH₃ | N | |
| H | CO₂CH₂CH₂CN | H | OCH₃ | CH₃ | N | |
| H | CO₂CH₂CH₂CN | H | OCH₂CH₃ | NHCH₃ | N | |
| H | CO₂CH₂CH₂CN | CH₃ | OCH₃ | CH₃ | N | |
| 5-CH₃ | CO₂CH₂CH₂CN | H | OCH₃ | OCH₃ | CH | |
| 5-OCH₃ | CO₂CH₂CH₂CN | H | OCH₃ | OCH₃ | CH | |
| 6-CH₃ | CO₂CH₂CH₂CN | H | OCH₃ | OCH₃ | CH | |
| 6-OCH₃ | CO₂CH₂CH₂CN | H | OCH₃ | OCH₃ | CH | |
| 6-F | CO₂CH₂CH₂CN | H | OCH₃ | OCH₃ | CH | |
| 6-Cl | CO₂CH₂CH₂CN | H | OCH₃ | OCH₃ | CH | |
| H | CO₂CH₂CH₂OSO₂CH₃ | H | OCH₃ | OCH₃ | CH | |
| H | CO₂CH₂CH₂OSO₂CH₃ | H | OCH₃ | CH₃ | CH | |
| H | CO₂CH₂CH₂OSO₂CH₃ | H | Cl | OCH₃ | CH | |
| H | CO₂CH₂CH₂OSO₂CH₃ | H | CH₃ | CH₃ | CH | |
| H | CO₂CH₂CH₂OSO₂CH₃ | H | OCH₃ | OCH₃ | N | |
| H | CO₂CH₂CH₂OSO₂CH₃ | H | OCH₃ | CH₃ | N | |
| H | CO₂CH₂CH₂OSO₂CH₃ | H | OCH₂CH₃ | NHCH₃ | N | |
| H | CO₂CH₂CH₂OSO₂CH₃ | CH₃ | OCH₃ | CH₃ | N | |
| 5-CH₃ | CO₂CH₂CH₂OSO₂CH₃ | H | OCH₃ | OCH₃ | CH | |
| 5-OCH₃ | CO₂CH₂CH₂OSO₂CH₃ | H | OCH₃ | OCH₃ | CH | |
| 6-CH₃ | CO₂CH₂CH₂OSO₂CH₃ | H | OCH₃ | OCH₃ | CH | |
| 6-OCH₃ | CO₂CH₂CH₂OSO₂CH₃ | H | OCH₃ | OCH₃ | CH | |
| 6-F | CO₂CH₂CH₂OSO₂CH₃ | H | OCH₃ | OCH₃ | CH | |
| 6-Cl | CO₂CH₂CH₂OSO₂CH₃ | H | OCH₃ | OCH₃ | CH | |

TABLE V

General Formula 5

| R₁ | R₆ | R | X | Y | Z | m.p.(°C.) |
|---|---|---|---|---|---|---|
| H | SO₂N(OCH₃)CH₃ | H | OCH₃ | OCH₃ | CH | |
| H | SO₂N(OCH₃)CH₃ | H | OCH₃ | CH₃ | CH | |
| H | SO₂N(OCH₃)CH₃ | H | Cl | OCH₃ | CH | |
| H | SO₂N(OCH₃)CH₃ | H | CH₃ | CH₃ | CH | |
| H | SO₂N(OCH₃)CH₃ | H | OCH₃ | OCH₃ | N | |
| H | SO₂N(OCH₃)CH₃ | H | OCH₃ | CH₃ | N | |
| H | SO₂N(OCH₃)CH₃ | H | OCH₂CH₃ | NHCH₃ | N | |
| H | SO₂N(OCH₃)CH₃ | CH₃ | OCH₃ | CH₃ | N | |
| 4-CH₃ | SO₂N(OCH₃)CH₃ | H | OCH₃ | OCH₃ | CH | |
| 4-OCH₃ | SO₂N(OCH₃)CH₃ | H | OCH₃ | OCH₃ | CH | |
| 6-CH₃ | SO₂N(OCH₃)CH₃ | H | OCH₃ | OCH₃ | CH | |
| 6-OCH₃ | SO₂N(OCH₃)CH₃ | H | OCH₃ | OCH₃ | CH | |
| 6-F | SO₂N(OCH₃)CH₃ | H | OCH₃ | OCH₃ | CH | |
| 6-Cl | SO₂N(OCH₃)CH₃ | H | OCH₃ | OCH₃ | CH | |
| H | CO₂CH₂CH₂OH | H | OCH₃ | OCH₃ | CH | |
| H | CO₂CH₂CH₂OH | H | OCH₃ | CH₃ | CH | |
| H | CO₂CH₂CH₂OH | H | Cl | OCH₃ | CH | |
| H | CO₂CH₂CH₂OH | H | CH₃ | CH₃ | CH | |
| H | CO₂CH₂CH₂OH | H | OCH₃ | OCH₃ | N | |
| H | CO₂CH₂CH₂OH | H | OCH₃ | CH₃ | N | |
| H | CO₂CH₂CH₂OH | H | OCH₂CH₃ | NHCH₃ | N | |
| H | CO₂CH₂CH₂OH | CH₃ | OCH₃ | CH₃ | N | |
| 4-CH₃ | CO₂CH₂CH₂OH | H | OCH₃ | OCH₃ | CH | |
| 4-OCH₃ | CO₂CH₂CH₂OH | H | OCH₃ | OCH₃ | CH | |
| 6-CH₃ | CO₂CH₂CH₂OH | H | OCH₃ | OCH₃ | CH | |
| 6-OCH₃ | CO₂CH₂CH₂OH | H | OCH₃ | OCH₃ | CH | |
| 6-F | CO₂CH₂CH₂OH | H | OCH₃ | OCH₃ | CH | |
| 6-Cl | CO₂CH₂CH₂OH | H | OCH₃ | OCH₃ | CH | |
| H | CO₂CH₂CH₂CN | H | OCH₃ | OCH₃ | CH | |
| H | CO₂CH₂CH₂CN | H | OCH₃ | CH₃ | CH | |
| H | CO₂CH₂CH₂CN | H | Cl | OCH₃ | CH | |
| H | CO₂CH₂CH₂CN | H | CH₃ | CH₃ | CH | |
| H | CO₂CH₂CH₂CN | H | OCH₃ | OCH₃ | N | |
| H | CO₂CH₂CH₂CN | H | OCH₃ | CH₃ | N | |
| H | CO₂CH₂CH₂CN | H | OCH₂CH₃ | NHCH₃ | N | |
| H | CO₂CH₂CH₂CN | CH₃ | OCH₃ | CH₃ | N | |
| 4-CH₃ | CO₂CH₂CH₂CN | H | OCH₃ | OCH₃ | CH | |
| 4-OCH₃ | CO₂CH₂CH₂CN | H | OCH₃ | OCH₃ | CH | |

TABLE V-continued

General Formula 5

| R₁ | R₆ | R | X | Y | Z | m.p.(°C.) |
|---|---|---|---|---|---|---|
| 6-CH₃ | CO₂CH₂CH₂CN | H | OCH₃ | OCH₃ | CH | |
| 6-OCH₃ | CO₂CH₂CH₂CN | H | OCH₃ | OCH₃ | CH | |
| 6-F | CO₂CH₂CH₂CN | H | OCH₃ | OCH₃ | CH | |
| 6-Cl | CO₂CH₂CH₂CN | H | OCH₃ | OCH₃ | CH | |
| H | CO₂CH₂CF₃ | H | OCH₃ | OCH₃ | CH | |
| H | CO₂CH₂CF₃ | H | OCH₃ | CH₃ | CH | |
| H | CO₂CH₂CF₃ | H | Cl | OCH₃ | CH | |
| H | CO₂CH₂CF₃ | H | CH₃ | CH₃ | CH | |
| H | CO₂CH₂CF₃ | H | OCH₃ | OCH₃ | N | |
| H | CO₂CH₂CF₃ | H | OCH₃ | CH₃ | N | |
| H | CO₂CH₂CF₃ | H | OCH₂CH₃ | NHCH₃ | N | |
| H | CO₂CH₂CF₃ | CH₃ | OCH₃ | CH₃ | N | |
| 4-CH₃ | CO₂CH₂CF₃ | H | OCH₃ | OCH₃ | CH | |
| 4-OCH₃ | CO₂CH₂CF₃ | H | OCH₃ | OCH₃ | CH | |
| 6-CH₃ | CO₂CH₂CF₃ | H | OCH₃ | OCH₃ | CH | |
| 6-OCH₃ | CO₂CH₂CF₃ | H | OCH₃ | OCH₃ | CH | |
| 6-F | CO₂CH₂CF₃ | H | OCH₃ | OCH₃ | CH | |
| 6-Cl | CO₂CH₂CF₃ | H | OCH₃ | OCH₃ | CH | |
| H | SO₂N(OCH₃)CH₃ | H | OCH₃ | OCH₃ | CH | |
| H | SO₂N(OCH₃)CH₃ | H | OCH₃ | CH₃ | CH | |
| H | SO₂N(OCH₃)CH₃ | H | Cl | OCH₃ | CH | |
| H | SO₂N(OCH₃)CH₃ | H | CH₃ | CH₃ | CH | |
| H | SO₂N(OCH₃)CH₃ | H | OCH₃ | OCH₃ | N | |
| H | SO₂N(OCH₃)CH₃ | H | OCH₃ | CH₃ | N | |
| H | SO₂N(OCH₃)CH₃ | H | OCH₂CH₃ | NHCH₃ | N | |
| H | SO₂N(OCH₃)CH₃ | CH₃ | OCH₃ | CH₃ | N | |
| 4-CH₃ | SO₂N(OCH₃)CH₃ | H | OCH₃ | OCH₃ | CH | |
| 4-Cl | SO₂N(OCH₃)CH₃ | H | OCH₃ | OCH₃ | CH | |
| 6-CH₃ | SO₂N(OCH₃)CH₃ | H | OCH₃ | OCH₃ | CH | |
| 6-OCH₃ | SO₂N(OCH₃)CH₃ | H | OCH₃ | OCH₃ | CH | |
| 6-F | SO₂N(OCH₃)CH₃ | H | OCH₃ | OCH₃ | CH | |
| 6-Cl | SO₂N(OCH₃)CH₃ | H | OCH₃ | OCH₃ | CH | |
| H | CO₂CH₂CH₂OH | H | OCH₃ | OCH₃ | CH | |
| H | CO₂CH₂CH₂OH | H | OCH₃ | CH₃ | CH | |
| H | CO₂CH₂CH₂OH | H | Cl | OCH₃ | CH | |
| H | CO₂CH₂CH₂OH | H | CH₃ | CH₃ | CH | |
| H | CO₂CH₂CH₂OH | H | OCH₃ | OCH₃ | N | |
| H | CO₂CH₂CH₂OH | H | OCH₃ | CH₃ | N | |
| H | CO₂CH₂CH₂OH | H | OCH₂CH₃ | NHCH₃ | N | |
| H | CO₂CH₂CH₂OH | CH₃ | OCH₃ | CH₃ | N | |
| 4-CH₃ | CO₂CH₂CH₂OH | H | OCH₃ | OCH₃ | CH | |
| 4-Cl | CO₂CH₂CH₂OH | H | OCH₃ | OCH₃ | CH | |
| 6-CH₃ | CO₂CH₂CH₂OH | H | OCH₃ | OCH₃ | CH | |
| 6-OCH₃ | CO₂CH₂CH₂OH | H | OCH₃ | OCH₃ | CH | |
| 6-F | CO₂CH₂CH₂OH | H | OCH₃ | OCH₃ | CH | |
| 6-Cl | CO₂CH₂CH₂OH | H | OCH₃ | OCH₃ | CH | |
| H | CO₂CH₂CH₂CN | H | OCH₃ | OCH₃ | CH | |
| H | CO₂CH₂CH₂CN | H | OCH₃ | CH₃ | CH | |
| H | CO₂CH₂CH₂CN | H | Cl | OCH₃ | CH | |
| H | CO₂CH₂CH₂CN | H | CH₃ | CH₃ | CH | |
| H | CO₂CH₂CH₂CN | H | OCH₃ | OCH₃ | N | |
| H | CO₂CH₂CH₂CN | H | OCH₃ | CH₃ | N | |
| H | CO₂CH₂CH₂CN | H | OCH₂CH₃ | NHCH₃ | N | |
| H | CO₂CH₂CH₂CN | CH₃ | OCH₃ | CH₃ | N | |
| 4-CH₃ | CO₂CH₂CH₂CN | H | OCH₃ | OCH₃ | CH | |
| 4-Cl | CO₂CH₂CH₂CN | H | OCH₃ | OCH₃ | CH | |
| 6-CH₃ | CO₂CH₂CH₂CN | H | OCH₃ | OCH₃ | CH | |
| 6-OCH₃ | CO₂CH₂CH₂CN | H | OCH₃ | OCH₃ | CH | |
| 6-F | CO₂CH₂CH₂CN | H | OCH₃ | OCH₃ | CH | |
| 6-Cl | CO₂CH₂CH₂CN | H | OCH₃ | OCH₃ | CH | |

TABLE VII

General Formula 7

| R₁ | R₂ | A | X | Y | m.p. (°C.) |
|---|---|---|---|---|---|
| H | SO₂NHCH₃ | A-2 | X₁ = CH₃ | Y₁ = CH₂ | |
| H | SO₂NHCH₃ | A-3 | X₁ = CH₃ | | |
| H | SO₂NHCH₃ | A-3 | X₁ = OCH₃ | | |
| H | SO₂NHCH₃ | A-4 | X₃ = OCH₃ | | |
| H | SO₂NHCH₂CH₂OCH₃ | A-2 | X₁ = CH₃ | Y₁ = CH₂ | |
| H | SO₂NHCH₂CH₂OCH₃ | A-3 | X₁ = CH₃ | | |
| H | SO₂NHCH₂CH₂OCH₃ | A-3 | X₁ = OCH₃ | | |
| H | SO₂NHCH₂CH₂OCH₃ | A-4 | X₃ = OCH₃ | | |
| H | CO₂CH₂CH₂OH | A-2 | X₁ = CH₃ | Y₁ = CH₂ | |
| H | CO₂CH₂CH₂OH | A-3 | X₁ = CH₃ | | |
| H | CO₂CH₂CH₂OH | A-3 | X₁ = OCH₃ | | |
| H | CO₂CH₂CH₂OH | A-4 | X₃ = OCH₃ | | |
| H | CO₂CH₂CH₂CN | A-2 | X₁ = CH₃ | Y₁ = CH₂ | |

TABLE VII-continued

General Formula 7

| R₁ | R₂ | A | X | Y | m.p. (°C.) |
|---|---|---|---|---|---|
| H | CO₂CH₂CH₂CN | A-3 | X₁ = CH₃ | | |
| H | CO₂CH₂CH₂CN | A-3 | X₁ = OCH₃ | | |
| H | CO₂CH₂CH₂CN | A-4 | X₃ = OCH₃ | | |
| H | CO₂CH₂CF₂ | A-2 | X₁ = CH₃ | Y₁ = CH₂ | |
| H | CO₂CH₂CF₂ | A-3 | X₁ = CH₃ | | |
| H | CO₂CH₂CF₂ | A-3 | X₁ = OCH₃ | | |
| 6-OCH₃ | SO₂N(CH₃)₂ | A-2 | X₁ = CH₃ | Y₁ = CH₂ | |
| 6-OCH₃ | SO₂N(CH₃)₂ | A-3 | X₁ = CH₃ | | |
| 6-OCH₃ | SO₂N(CH₃)₂ | A-3 | X₁ = OCH₃ | | |
| 6-OCH₃ | SO₂N(CH₃)₂ | A-4 | X₃ = OCH₃ | | |
| 6-SCH₃ | SO₂N(CH₃)₂ | A-2 | X₁ = CH₃ | Y₁ = CH₂ | |
| 6-SCH₃ | SO₂N(CH₃)₂ | A-3 | X₁ = CH₃ | | |
| 6-SCH₃ | SO₂N(CH₃)₂ | A-3 | X₁ = OCH₃ | | |
| 6-SCH₃ | SO₂N(CH₃)₂ | A-4 | X₃ = OCH₃ | | |
| 6-N(CH₃)₂ | SO₂N(CH₃)₂ | A-2 | X₁ = CH₃ | Y₁ = CH₂ | |
| 6-N(CH₃)₂ | SO₂N(CH₃)₂ | A-3 | X₁ = CH₃ | | |
| 6-N(CH₃)₂ | SO₂N(CH₃)₂ | A-3 | X₁ = OCH₃ | | |
| 6-N(CH₃)₂ | SO₂N(CH₃)₂ | A-4 | X₃ = OCH₃ | | |
| 6-NHCH₃ | SO₂N(CH₃)₂ | A-2 | X₁ = CH₃ | Y₁ = CH₂ | |
| 6-NHCH₃ | SO₂N(CH₃)₂ | A-3 | X₁ = CH₃ | | |
| 6-NHCH₃ | SO₂N(CH₃)₂ | A-3 | X₁ = OCH₃ | | |
| 6-NHCH₃ | SO₂N(CH₃)₂ | A-4 | X₃ = OCH₃ | | |
| 6-OCH₃ | CO₂CH₃ | A-2 | X₁ = CH₃ | Y₁ = CH₂ | |
| 6-OCH₃ | CO₂CH₃ | A-3 | X₁ = CH₃ | | |
| 6-OCH₃ | CO₂CH₃ | A-3 | X₁ = OCH₃ | | |
| 6-OCH₃ | CO₂CH₃ | A-4 | X₃ = OCH₃ | | |
| 6-SCH₃ | CO₂CH₃ | A-2 | X₁ = CH₃ | Y₁ = CH₂ | |
| 6-SCH₃ | CO₂CH₃ | A-3 | X₁ = CH₃ | | |
| 6-SCH₃ | CO₂CH₃ | A-3 | X₁ = OCH₃ | | |
| 6-SCH₃ | CO₂CH₃ | A-4 | X₃ = OCH₃ | | |
| 6-N(CH₃)₂ | CO₂CH₃ | A-2 | X₁ = CH₃ | Y₁ = CH₂ | |
| 6-N(CH₃)₂ | CO₂CH₃ | A-3 | X₁ = CH₃ | | |
| 6-N(CH₃)₂ | CO₂CH₃ | A-3 | X₁ = OCH₃ | | |
| 6-N(CH₃)₂ | CO₂CH₃ | A-4 | X₃ = OCH₃ | | |
| 6-NHCH₃ | SO₂N(CH₃)₂ | A-2 | X₁ = CH₃ | Y₁ = CH₂ | |
| 6-NHCH₃ | SO₂N(CH₃)₂ | A-3 | X₁ = CH₃ | | |
| 6-NHCH₃ | SO₂N(CH₃)₂ | A-3 | X₁ = OCH₃ | | |
| 6-NHCH₃ | SO₂N(CH₃)₂ | A-4 | X₃ = OCH₃ | | |
| 6-OCH₃ | SO₂N(CH₃)₂ | A-2 | X₁ = CH₃ | Y₁ = CH₂ | |
| 6-OCH₃ | SO₂N(CH₃)₂ | A-3 | X₁ = CH₃ | | |
| 6-OCH₃ | SO₂N(CH₃)₂ | A-3 | X₁ = OCH₃ | | |
| 6-OCH₃ | SO₂N(CH₃)₂ | A-4 | X₃ = OCH₃ | | |
| 6-SCH₃ | SO₂N(CH₃)₂ | A-2 | X₁ = CH₃ | Y₁ = CH₂ | |
| 6-SCH₃ | SO₂N(CH₃)₂ | A-3 | X₁ = CH₃ | | |
| 6-SCH₃ | SO₂N(CH₃)₂ | A-3 | X₁ = OCH₃ | | |
| 6-SCH₃ | SO₂N(CH₃)₂ | A-4 | X₃ = OCH₃ | | |
| 6-N(CH₃)₂ | SO₂N(CH₃)₂ | A-2 | X₁ = CH₃ | Y₁ = CH₂ | |
| 6-N(CH₃)₂ | SO₂N(CH₃)₂ | A-3 | X₁ = CH₃ | | |
| 6-N(CH₃)₂ | SO₂N(CH₃)₂ | A-3 | X₁ = OCH₃ | | |
| 6-N(CH₃)₂ | SO₂N(CH₃)₂ | A-4 | X₃ = OCH₃ | | |
| 6-NHCH₃ | CO₂CH₃ | A-2 | X₁ = CH₃ | Y₁ = CH₂ | |
| 6-NHCH₃ | CO₂CH₃ | A-3 | X₁ = CH₃ | | |
| 6-NHCH₃ | CO₂CH₃ | A-3 | X₁ = OCH₃ | | |
| 6-NHCH₃ | CO₂CH₃ | A-4 | X₃ = OCH₃ | | |
| 6-OCH₃ | SO₂NHOCH₃ | A-2 | X₁ = CH₃ | Y₁ = CH₂ | |
| 6-OCH₃ | SO₂NHOCH₃ | A-3 | X₁ = CH₃ | | |
| 6-OCH₃ | SO₂NHOCH₃ | A-3 | X₁ = OCH₃ | | |
| 6-OCH₃ | SO₂NHOCH₃ | A-4 | X₃ = OCH₃ | | |
| 6-SCH₃ | SO₂NHOCH₃ | A-2 | X₁ = CH₃ | Y₁ = CH₂ | |
| 6-SCH₃ | SO₂NHOCH₃ | A-3 | X₁ = CH₃ | | |
| 6-SCH₃ | SO₂NHOCH₃ | A-3 | X₁ = OCH₃ | | |
| 6-SCH₃ | SO₂NHOCH₃ | A-4 | X₃ = OCH₃ | | |
| 6-N(CH₃)₂ | SO₂NHOCH₃ | A-2 | X₁ = CH₃ | Y₁ = CH₂ | |
| 6-N(CH₃)₂ | SO₂NHOCH₃ | A-3 | X₁ = CH₃ | | |
| 6-N(CH₃)₂ | SO₂NHOCH₃ | A-3 | X₁ = OCH₃ | | |
| 6-N(CH₃)₂ | SO₂NHOCH₃ | A-4 | X₃ = OCH₃ | | |
| 6-NHCH₃ | SO₂NHOCH₃ | A-2 | X₁ = CH₃ | Y₁ = CH₂ | |
| 6-NHCH₃ | SO₂NHOCH₃ | A-3 | X₁ = CH₃ | | |
| 6-NHCH₃ | SO₂NHOCH₃ | A-3 | X₁ = OCH₃ | | |
| 6-NHCH₃ | SO₂NHOCH₃ | A-4 | X₃ = OCH₃ | | |
| 6-OCH₃ | CO₂CH₂CH₃ | A-2 | X₁ = CH₃ | Y₁ = CH₂ | |
| 6-OCH₃ | CO₂CH₂CH₃ | A-3 | X₁ = CH₃ | | |
| 6-OCH₃ | CO₂CH₂CH₃ | A-3 | X₁ = OCH₃ | | |
| 6-OCH₃ | CO₂CH₂CH₃ | A-4 | X₄ = OCH₃ | | |
| 6-OCH₃ | CO₂CH₂CH₃ | A-2 | X₁ = CH₃ | Y₁ = CH₂ | |
| 6-OCH₃ | CO₂CH₂CH₃ | A-3 | X₁ = CH₃ | | |
| 6-OCH₃ | CO₂CH₂CH₃ | A-3 | X₁ = OCH₃ | | |
| 6-OCH₃ | CO₂CH₂CH₃ | A-4 | X₃ = OCH₃ | | |
| 6-OCH₃ | CO₂CH₂CH₃ | A-2 | X₁ = CH₃ | Y₁ = CH₂ | |
| 6-OCH₃ | CO₂CH₂CH₃ | A-3 | X₁ = CH₃ | | |

TABLE VII-continued

General Formula 7

| $R_1$ | $R_2$ | A | X | Y | m.p. (°C.) |
|---|---|---|---|---|---|
| 6-OCH$_3$ | CO$_2$CH$_2$CH$_3$ | A-3 | $X_1$ = OCH$_3$ | | |
| 6-OCH$_3$ | CO$_2$CH$_2$CH$_3$ | A-4 | $X_3$ = OCH$_3$ | | |
| 6-OCH$_3$ | CO$_2$CH$_2$CH$_3$ | A-2 | $X_1$ = CH$_3$ | $Y_1$ = CH$_2$ | |
| 6-OCH$_3$ | CO$_2$CH$_2$CH$_3$ | A-3 | $X_1$ = CH$_3$ | | |
| 6-OCH$_3$ | CO$_2$CH$_2$CH$_3$ | A-3 | $X_1$ = OCH$_3$ | | |
| 6-OCH$_3$ | CO$_2$CH$_2$CH$_3$ | A-4 | $X_3$ = OCH$_3$ | | |

TABLE VIII

General Formula 8

| $R_1$ | $R_3$ | A | X | Y | m.p. (°C.) |
|---|---|---|---|---|---|
| H | SO$_2$NHCH$_3$ | A-2 | $X_1$ = CH$_3$ | $Y_1$ = CH$_2$ | |
| H | SO$_2$NHCH$_3$ | A-3 | $X_1$ = CH$_3$ | | |
| H | SO$_2$NHCH$_3$ | A-3 | $X_1$ = OCH$_3$ | | |
| H | SO$_2$NHCH$_3$ | A-4 | $X_3$ = OCH$_3$ | | |
| H | CO$_2$CH$_2$CH$_2$OH | A-2 | $X_1$ = CH$_3$ | $Y_1$ = CH$_2$ | |
| H | CO$_2$CH$_2$CH$_2$OH | A-3 | $X_1$ = CH$_3$ | | |
| H | CO$_2$CH$_2$CH$_2$OH | A-3 | $X_1$ = OCH$_3$ | | |
| H | CO$_2$CH$_2$CH$_2$OH | A-4 | $X_3$ = OCH$_3$ | | |
| H | CO$_2$CH$_2$CH$_2$CN | A-2 | $X_1$ = CH$_3$ | $Y_1$ = CH$_2$ | |
| H | CO$_2$CH$_2$CH$_2$CN | A-3 | $X_1$ = CH$_3$ | | |
| H | CO$_2$CH$_2$CH$_2$CN | A-3 | $X_1$ = OCH$_3$ | | |
| H | CO$_2$CH$_2$CH$_2$CN | A-4 | $X_3$ = OCH$_3$ | | |
| H | CO$_2$CH$_2$CF$_3$ | A-2 | $X_1$ = CH$_3$ | $Y_1$ = CH$_2$ | |
| H | CO$_2$CH$_2$CF$_3$ | A-3 | $X_1$ = CH$_3$ | | |
| H | CO$_2$CH$_2$CF$_3$ | A-3 | $X_1$ = OCH$_3$ | | |
| H | CO$_2$CH$_2$CF$_3$ | A-4 | $X_3$ = OCH$_3$ | | |

TABLE IX

General Formula 9

| $R_1$ | $R_4$ | A | X | Y | m.p. (°C.) |
|---|---|---|---|---|---|
| H | SO$_2$N(OCH$_3$)CH$_3$ | A-2 | $X_1$ = CH$_3$ | $Y_1$ = CH$_2$ | |
| H | SO$_2$N(OCH$_3$)CH$_3$ | A-3 | $X_1$ = CH$_3$ | | |
| H | SO$_2$N(OCH$_3$)CH$_3$ | A-3 | $X_1$ = OCH$_3$ | | |
| H | SO$_2$N(OCH$_3$)CH$_3$ | A-4 | $X_3$ = OCH$_3$ | | |
| H | SO$_2$NHCH$_3$ | A-2 | $X_1$ = CH$_3$ | $Y_1$ = CH$_2$ | |
| H | SO$_2$NHCH$_3$ | A-3 | $X_1$ = CH$_3$ | | |
| H | SO$_2$NHCH$_3$ | A-3 | $X_1$ = OCH$_3$ | | |
| H | SO$_2$NHCH$_3$ | A-4 | $X_3$ = OCH$_3$ | | |
| H | CO$_2$CH$_2$CH$_2$OH | A-2 | $X_1$ = CH$_3$ | $Y_1$ = CH$_2$ | |
| H | CO$_2$CH$_2$CH$_2$OH | A-3 | $X_1$ = CH$_3$ | | |
| H | CO$_2$CH$_2$CH$_2$OH | A-3 | $X_1$ = OCH$_3$ | | |
| H | CO$_2$CH$_2$CH$_2$OH | A-4 | $X_3$ = OCH$_3$ | | |
| H | CO$_2$CH$_2$CH$_2$CN | A-2 | $X_1$ = CH$_3$ | $Y_1$ = CH$_2$ | |
| H | CO$_2$CH$_2$CH$_2$CN | A-3 | $X_1$ = CH$_3$ | | |
| H | CO$_2$CH$_2$CH$_2$CN | A-3 | $X_1$ = OCH$_3$ | | |
| H | CO$_2$CH$_2$CH$_2$CN | A-4 | $X_3$ = OCH$_3$ | | |
| H | CO$_2$CH$_2$CF$_3$ | A-2 | $X_1$ = CH$_3$ | $Y_1$ = CH$_2$ | |
| H | CO$_2$CH$_2$CF$_3$ | A-3 | $X_1$ = CH$_3$ | | |
| H | CO$_2$CH$_2$CF$_3$ | A-3 | $X_1$ = OCH$_3$ | | |
| H | CO$_2$CH$_2$CF$_3$ | A-4 | $X_3$ = OCH$_3$ | | |

TABLE X

General Formula 10

| $R_1$ | $R_5$ | A | X | Y | m.p. (°C.) |
|---|---|---|---|---|---|
| H | SO$_2$N(OCH$_3$)CH$_3$ | A-2 | $X_1$ = CH$_3$ | $Y_1$ = CH$_2$ | |
| H | SO$_2$N(OCH$_3$)CH$_3$ | A-3 | $X_1$ = CH$_3$ | | |
| H | SO$_2$N(OCH$_3$)CH$_3$ | A-3 | $X_1$ = OCH$_3$ | | |
| H | SO$_2$N(OCH$_3$)CH$_3$ | A-4 | $X_3$ = OCH$_3$ | | |
| H | SO$_2$NHCH$_3$ | A-2 | $X_1$ = CH$_3$ | $Y_1$ = CH$_2$ | |
| H | SO$_2$NHCH$_3$ | A-3 | $X_1$ = CH$_3$ | | |
| H | SO$_2$NHCH$_3$ | A-3 | $X_1$ = OCH$_3$ | | |
| H | SO$_2$NHCH$_3$ | A-4 | $X_3$ = OCH$_3$ | | |
| H | SO$_2$NHCH$_2$CH$_3$ | A-2 | $X_1$ = CH$_3$ | $Y_1$ = CH$_2$ | |
| H | SO$_2$NHCH$_2$CH$_3$ | A-3 | $X_1$ = CH$_3$ | | |
| H | SO$_2$NHCH$_2$CH$_3$ | A-3 | $X_1$ = OCH$_3$ | | |
| H | SO$_2$NHCH$_2$CH$_3$ | A-4 | $X_3$ = OCH$_3$ | | |
| H | CO$_2$CH$_2$CH$_2$OH | A-2 | $X_1$ = CH$_3$ | $Y_1$ = CH$_2$ | |
| H | CO$_2$CH$_2$CH$_2$OH | A-3 | $X_1$ = CH$_3$ | | |
| H | CO$_2$CH$_2$CH$_2$OH | A-3 | $X_1$ = OCH$_3$ | | |
| H | CO$_2$CH$_2$CH$_2$OH | A-4 | $X_3$ = OCH$_3$ | | |
| H | CO$_2$CH$_2$CH$_2$CN | A-2 | $X_1$ = CH$_3$ | $Y_1$ = CH$_2$ | |
| H | CO$_2$CH$_2$CH$_2$CN | A-3 | $X_1$ = CH$_3$ | | |
| H | CO$_2$CH$_2$CH$_2$CN | A-3 | $X_1$ = OCH$_3$ | | |
| H | CO$_2$CH$_2$CH$_2$CN | A-4 | $X_3$ = OCH$_3$ | | |
| H | CO$_2$CH$_2$CF$_3$ | A-2 | $X_1$ = CH$_3$ | $Y_1$ = CH$_2$ | |
| H | CO$_2$CH$_2$CF$_3$ | A-3 | $X_1$ = CH$_3$ | | |
| H | CO$_2$CH$_2$CF$_3$ | A-3 | $X_1$ = OCH$_3$ | | |
| H | CO$_2$CH$_2$CF$_3$ | A-4 | $X_3$ = OCH$_3$ | | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to about 99.9% solid or liquid inert diluent(s). More specifically, they will contain these ingredients in the following approximate proportions:

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering,* Dec. 4, 1967, pp. 147ff. and "Perry's Chemical Engineer's Handbook", 5th Ed., McGraw-Hill, New York, 1963, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 and Examples 1-4;

G. C. Klingman, "Weed Control as a Science", John Wiley and Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 13

High Strength Concentrate

| | |
|---|---|
| N2-[(4,6-Dimethoxypyrimidin-2-yl)aminocarbonyl]-N3-methyl-2,3-pyridinedisulfonamide | 99% |
| trimethylnonyl polyethylene glycol ether | 1% |

The surfactant is sprayed upon the active ingredient in a blender and the mixture sifted through a U.S.S. No. 40 sieve (0.42 mm openings) prior to packaging. The concentrate may be formulated further for practical use.

EXAMPLE 14

Wettable Powder

| | |
|---|---|
| 2-[[(4,6-Dimethoxypyrimidin-2-yl)aminocarbonyl]-aminosulfonyl]-3-pyridinecarboxylic acid, methyl ester | 65% |
| dodecylphenol polyethylene glycol ether | 2% |
| sodium ligninsulfonate | 4% |
| sodium silicoaluminate | 6% |
| montmorillonite (calcined) | 23% |

The ingredients are thoroughly blended. The liquid surfactant is added by spraying upon the solid ingredients in the blender. After grinding in a hammer mill to produce particles essentially all below 100 microns, the material is reblended and sifted through a U.S.S. No. 50 sieve (0.3 mm opening) and packaged.

EXAMPLE 15

Aqueous Suspension

| | |
|---|---|
| N2-[(4,6-Dimethoxypyrimidin-2-yl)aminocarbonyl]-N3-methyl-2,3-pyridinedisulfonamide | 50.0% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 16

Oil Suspension

| | |
|---|---|
| 2-[[(4,6-Dimethoxypyrimidin-2-yl)aminocarbonyl]-aminosulfonyl]-3-pyridinecarboxylic acid, methyl ester | 35% |
| blend of polyalcohol carboxylic esters and oil soluble petroleum sulfonates | 6% |
| xylene | 59% |

The ingredients are combined and ground together in a sand mill to produce particles essentially all below 3 microns. The product can be used directly, extended with oils, or emulsified in water.

EXAMPLE 17

Oil Suspension

| | |
|---|---|
| 2-[[(4,6-Dimethoxypyrimidin-2-yl)aminocarbonyl]-aminosulfonyl]-3-pyridinecarboxylic acid, methyl ester | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 18

Aqueous Suspension

| | |
|---|---|
| 2-[[(4,6-Dimethoxypyrimidin-2-yl)aminocarbonyl]-aminosulfonyl]-3-pyridinecarboxylic acid, methyl ester | 25% |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to diameters under 10 microns.

EXAMPLE 19

Wettable Powder

| | |
|---|---|
| N2—[(4,6-Dimethoxypyrimidin-2-yl)aminocarbonyl]-N3—methyl-2,3-pyridinedisulfonamide | 40.0% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE 20

Granule

| | |
|---|---|
| wettable powder of Example 19 | 15% |
| gypsum | 69% |
| potassium sulfate | 16% |

The ingredients are blended in a rotating mixer and water sprayed on to accomplish granulation. When most of the material has reached the desired range of 1.0 to 0.42 cm (U.S.S. #18 to 40 sieves), the granules are removed, dried, and screened. Oversized material is crushed to produce additional material in the desired range. These granules contain % active ingredient.

EXAMPLE 21

Wettable Powder

| | |
|---|---|
| 2-[[(4,6-Dimethoxypyrimidin-2-yl)aminocarbonyl]-aminosulfonyl]-3-pyridinecarboxylic acid, methyl ester | 50% |
| sodium alkylnaphthalenesulfonate | 2% |
| low viscosity methyl cellulose | 2% |
| diatomaceous earth | 46% |

The ingredients are blended, coarsely hammer-milled and the air milled to produce particles of active essentially all below 10 microns in diameter. The product is reblended before packaging.

EXAMPLE 22

Extruded Pellet

| | |
|---|---|
| N2—[(4,6-Dimethoxypyrimidin-2-yl)aminocarbonyl]-N3—methyl-2,3-pyridinedisulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 23

Wettable Powder

| | |
|---|---|
| 2-[[(4,6-Dimethoxypyrimidin-2-yl)aminocarbonyl]-aminosulfonyl]-3-pyridinecarboxylic acid, methyl ester | 80% |
| sodium alkylnaphthalenesulfonate | 2% |
| sodium ligninsulfonate | 2% |
| synthetic amorphous silica | 3% |
| kaolinite | 13% |

The ingredients are blended and then ground in a hammermill to produce particles with an average particle size less than 25 microns in diameter. The material is reblended and sifted through a U.S.S. No. 50 sieve (0.3 mm opening) before being packaged.

EXAMPLE 24

High Strength Concentrate

| | |
|---|---|
| N2—[(4,6-Dimethoxypyrimidin-2-yl)aminocarbonyl]-N3—methyl-2,3-pyridinedisulfonamide | 98.5% |
| silica aerogel | 0.5% |
| synthetic amorphous fine silica | 1.0% |

The ingredients are blended and ground in a hammer mill to produce a high strength concentrate essentially all passing a U.S.S. No. 50 sieve (0.3 mm openings). This material may then be formulated in a variety of ways.

UTILITY

Test results indicate that the compounds of the present invention are highly active preemergent or postemergent herbicides or plant growth regulants. Many of them have utility for broad-spectrum pre- and/or post-emergence weed control in areas where complete control of all vegetation is desired, such as around fuel storage tanks, industrial storage areas, parking lots, drive-in theaters, around billboards, highway and railroad structures. Some of the compounds have utility for selective weed control in crops such as wheat, barley corn, cotton and soybeans. In particular some of the compounds of this invention control weeds in corn (maize) both pre- and postemergence without sig-nificant crop damage. They are particularly useful to control such problem weeds as the foxtail (Setaria spp.), fall panicum (*Panicum dichotomiflorum*), barn-yardgrass (*Echinochloa crusgalli*), seedling john-songrass (*Sorghum halepense*) and shattercane (*Sorghum bicolor*). *They can be used preemergence or post-emergence and are most effective when applied post-emergence to young weeds. They are also effective on certain broadleaf weeds such as lambsquarter (Chenopodium album),* pigweed (Amaranthus spp.) and velvet leaf (*Abutilon theophras*).

Alternatively, the subject compounds are useful to modify plant growth.

The rates of application of the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.001 to 20 kg/ha, the lower rates being suggested for use on lighter soils and/or those having a low organic matter content, for plant growth modification or for situations where only short-term persistence is required.

The compounds of the invention may be used in combination with any other commercial herbicide, examples of which are those of the triazine, triazole, imidazolinone, uracil, urea, amide, diphenylether, cineole, carbamate and bipyridiylium types. They are particularly useful in combination with the following herbicides.

| Common Name | Chemical Name |
|---|---|
| alachlor | 2-chloro-2',6'-diethyl-N—(methoxymethyl)-acetanilide |
| atrazine | 2-chloro-4-(ethylamino)-6-(isopropylamino)-s-triazine |
| butylate | s-ethyl-diisobutylthiocarbamate |
| cyanazine | 2-[[4-chloro-6-(ethylamino)-s-triazin-2-yl]amino]-2-methylpropionitrile |
| dicamba | 3,6-dichloro-o-anisic acid |
| EPTC | S—ethyl dipropylthiocarbamate |
| linuron | 3-(3,4-dichlorophenyl)-1-methoxy-1-methylurea |
| metolachlor | 2-chloro-N—(2-ethyl-6-methylphenyl)-N—(2-methoxy-1-methylethyl)acetamide |
| metribuzin | 4-amino-6-tert-butyl-3-(methylthio)-as-triazine-5(4H)—one |
| tridiphane | 2-(3,5-dichlorophenyl)-2-(2,2,2-trichloroethyl)oxirane |
| 2,4-D | (2,4-dichlorophenoxy)acetic acid |
| bromoxynil | 3,5-dibromo-4-hydroxyphenylcyanide |
| paraquat | 1,1'-dimethyl-4,4-bipyridinium ion |
| glyphosate | N—(phosphonomethyl)glycine |

| Trade Name | Chemical Name |
|---|---|
| Harmony TM | 3-[[(4-methoxy-6-methyl-1,3,5-triazin-2-yl)aminocarbonyl]aminosulfonyl]-2-thiophenecarboxylic acid, methyl ester |
| Cinch ® | 1-methyl-4-(1-methylethyl)-2-exo-[(2-methylphenyl)-methoxy]-7-oxabicyclo-[2.2.1]heptane |
| — | 2-ethoxy-N—[[4-2,2,2-trifluoroethoxy)-6-methoxy-1,3,5-triazin-2-yl]aminocarbonyl]benzenesulfonamide |

The herbicidal properties of the subject compounds were discovered in a number of greenhouse tests. The test procedures and results follow.

Compounds

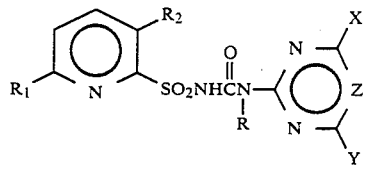

| Compound | $R_2$ | R | $R_1$ | X | Y | Z |
|---|---|---|---|---|---|---|
| 1 | $SO_2NHCH_3$ | H | H | $OCH_3$ | $OCH_3$ | CH |
| 2 | $SO_2NHCH_3$ | H | H | Cl | $OCH_3$ | CH |
| 3 | $SO_2NHCH_3$ | H | H | $CH_3$ | $CH_3$ | CH |
| 4 | $SO_2NHCH_3$ | H | H | $OCH_3$ | $CH_3$ | N |
| 5 | $SO_2N(OCH_3)CH_3$ | H | H | $OCH_3$ | $OCH_3$ | CH |
| 6 | $SO_2N(OCH_3)CH_3$ | H | H | $OCH_3$ | $CH_3$ | CH |
| 7 | $SO_2N(OCH_3)CH_3$ | H | H | $OCH_3$ | $CH_3$ | N |
| 8 | $SO_2N(OCH_2)CH_3$ | $CH_3$ | H | $OCH_3$ | $CH_3$ | N |
| 9 | $SO_2NHCH_2CH_3$ | H | H | $OCH_3$ | $OCH_3$ | CH |
| 10 | $SO_2NHCH_2CH_3$ | H | H | Cl | $OCH_3$ | CH |
| 11 | $SO_2NHCH_2CH_3$ | H | H | $CH_3$ | $CH_3$ | CH |
| 12 | $SO_2NHCH_2CH_3$ | H | H | $OCH_3$ | $OCH_3$ | N |
| 13 | $SO_2NHCH_2CH_3$ | H | H | $OCH_3$ | $CH_3$ | N |
| 14 | $SO_2NHCH_2CH_3$ | H | H | $OCH_3$ | $CH_3$ | N |
| 15 | $SO_2NHCH_2CH_2CH_3$ | H | H | $OCH_3$ | $OCH_3$ | CH |
| 16 | $SO_2NHCH_2CH_2CH_3$ | H | H | $CH_3$ | $OCH_3$ | CH |
| 17 | $SO_2NHCH_2CH_2CH_3$ | H | H | Cl | $OCH_3$ | CH |
| 18 | $SO_2NHCH_2CH_2CH_3$ | H | H | $OCH_3$ | $OCH_3$ | N |
| 19 | $SO_2N$⟨(CH_2)_4⟩ | H | H | $OCH_3$ | $OCH_3$ | CH |
| 20 | $SO_2N$⟨(CH_2)_4⟩ | H | H | $CH_3$ | $CH_3$ | CH |
| 21 | $CO_2CH_2$cyclopropyl | H | H | $OCH_3$ | $OCH_3$ | CH |
| 22 | $CO_2CH_2$cyclopropyl | H | H | Cl | $OCH_3$ | CH |
| 23 | $CO_2CH_2$cyclopropyl | H | H | $CH_3$ | $CH_3$ | CH |
| 24 | $CO_2CH_2$cyclopropyl | H | H | $OCH_3$ | $OCH_3$ | N |
| 25 | $CO_2CH_3$ | H | $OCH_3$ | $OCH_3$ | $OCH_3$ | CH |
| 26 | $CO_2CH_3$ | H | $OCH_3$ | $CH_3$ | $OCH_3$ | CH |
| 27 | $CO_2CH_3$ | H | $OCH_3$ | Cl | $OCH_3$ | CH |
| 28 | $CO_2CH_3$ | H | $OCH_3$ | $CH_3$ | $CH_3$ | CH |

-continued

Compounds

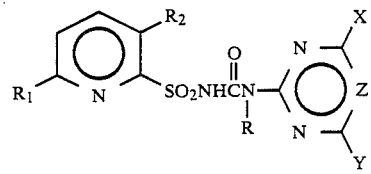

| Compound | R₂ | R | R₁ | X | Y | Z |
|---|---|---|---|---|---|---|
| 29 | CO₂CH₃ | H | OCH₃ | OCH₃ | OCH₃ | N |
| 30 | CO₂CH₃ | H | OCH₃ | CH₃ | OCH₃ | N |

TEST A

Seeds of crabgrass (Digitaria spp.), barnyardgrass (*Echinochloa crusgalli*), giant foxtail (*Setaria faberi*), wild oats (*Avena fatua*), cheatgrass (*Bromus secalinus*), velvetleaf (*Abutilon theophrasti*), morningglory (Ipomoea spp.), cocklebur (*Xanthium pensylvanicum*), sorghum, corn, soybean, sugarbeet, cotton, rice, wheat, barley and purple nutsedge (*Cyperus rotundus*) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
B=burn;
D=defoliation;
E=emergence inhibition;
G=growth retardation;
H=formative effect;
U=unusual pigmentation;
X=axillary stimulation;
S=albinism; and
6Y=abscised buds or flowers.

TABLE A

| RATE = KG/HA | CMPD 1 | | CMPD 2 | | CMPD 3 | | CMPD 4 | | CMPD 5 | | CMPD 6 | | CMPD 7 | | CMPD 8 | | CMPD 9 | | CMPD 10 | | CMPD 11 | |
|---|---|---|---|---|---|---|---|---|---|---|---|---|---|---|---|---|---|---|---|---|---|---|
| | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 |
| | | | | | | | | | POSOL | | | | | | | | | | | | | |
| COTTON | 10C | 10C | 6C,9G | 3C,7H | 4C,9G | 2C,5G | 0 | 0 | 5G | 4C,8G | 0 | 0 | 0 | 0 | 3C,9H | 4C,9G | 5C,9G | 5C,9G | 5C,9G | 3C,7G | 2C,3H |
| MORNING GLORY | 10C | 10C | 9C | 2G | 4C,9G | 1H | 0 | 2C | 10C | 10C | 2C,7G | 0 | 2G | 2C,5H | 3C,8G | 9C | 5C,9G | 3C,8H | 2C,3H |
| COCKLEBUR | 10C | 10C | 10C | 3C,9H | 3C,8H | 2G | 0 | 0 | 4C,9H | 10C | 2C | 0 | 0 | 3C,8H | 4C,9H | 9C | 10C | 2C,8H | 2H |
| NUTSEDGE | 5C,9G | 9C | 2C,9G | — | 2C,6G | 0 | 0 | 0 | 2C,5G | 9G | 5G | 4G | 0 | 0 | 0 | 0 | 2C,9G | 4C,9G | 9G | 0 |
| CRABGRASS | 5G | 8G | 5G | 0 | 0 | 1H | 0 | 0 | 9G | 10C | 0 | 0 | 0 | 0 | 0 | 0 | 3C,7G | 3C,7G | 2C,4G | 4G |
| BARNYARD GRASS | 9C | 9C | 3C,9H | 3C,9H | 0 | 0 | 0 | 0 | 9G | 10C | 0 | 0 | 0 | 0 | 0 | 0 | 4C,9G | 5C,9G | 3C,9H | 2H |
| WILD OATS | 3C,8G | 2C,7G | 5G | 0 | 0 | 0 | 0 | 0 | 3C,9G | 5C,9G | 2G | 0 | 0 | 0 | 0 | 0 | 3C,9G | 9C | 0 | 2C,8G |
| WHEAT | 9G | 9C | 8G | 3C,9H | 0 | 1H | 0 | 0 | 9G | 9C | 0 | 0 | 0 | 0 | 0 | 0 | 3C,9G | 5C,9G | 2C,7G | 2C,8G |
| CORN | 3G | 6G | 3G | 5G | 3C,4H | 0 | 0 | 0 | 9G | 3C,9G | 2G | 0 | 0 | 0 | 0 | 0 | 9C | 9G | 2C,5G | 0 |
| SOYBEAN | 9C | 9C | 2C,6H | 3G | 0 | 0 | 0 | 0 | 1C | 5C,9H | 2H | 0 | 0 | 0 | 0 | 0 | 1C | 5C,9G | 1C | 3G |
| RICE | 6C,9G | 6C,9G | 3C,7G | 10E | 0 | 0 | 0 | 0 | 6C,9G | 5C,9H | 0 | 0 | 0 | 0 | 0 | 2C,6G | 4C,9H | 9G | 3G | 0 |
| SORGHUM | 5C,9G | 5C,9G | 6C,9G | 7C,9H | 3C,4H | 0 | 0 | 0 | 5C,9G | 3C,9G | 2H | 0 | 0 | 0 | 3C,6H | 4C,8H | 5C,9G | 9C | 2C,8G | 3C,7G | 3C,4H |
| CHEATGRASS | 8G | 9C | 9C | 9H | 0 | 2G | 0 | 0 | 3C,8G | 9C | 4G | 0 | 0 | 0 | 0 | 2G | 9C | 4C,9G | 4C,9G | 4G |
| SUGAR BEETS | 9C | 9C | 2C,9G | 7C,9H | 0 | 0 | 0 | 0 | 9C | 9C | 8G | 7G | 3G | 0 | 6G | 3C,7H | 9C | 2C,9G | 0 |
| VELVETLEAF | 10C | 10C | 4C,9H | 4C,8H | 0 | 2G | 0 | 0 | 3C,7G | 10C | 0 | 0 | 7G | 2C | 6H | 5G | 9C | 5C,9H | 5C,9H | 5G |
| GIANT FOXTAIL | 9C | 10C | 3C,8G | 0 | 0 | 2C,7G | 0 | 0 | 9G | 10C | 0 | 0 | 3G | 0 | 7G | 10C | 9C | 3C,7H | 3C,7H | 3C,5G |
| BARLEY | 9C | 9C | 3C,8G | 3C,5G | 0 | 2G | 0 | 0 | 5C,9G | 10C | 0 | 0 | 0 | 0 | 9G | 1H | 9C | 3C,7G | 5G |
| DOWNY BROME | 2C,8G | 5C,9G | 7G | 0 | 3C,6G | 0 | 0 | 0 | 8G | 6C,9G | 0 | 0 | 0 | 0 | 4C,9G | 5C,9G | 2C,5G | 0 | 4G |

| RATE = KG/HA | CMPD 12 | | CMPD 13 | | CMPD 14 | | CMPD 15 | | CMPD 16 | | CMPD 17 | | CMPD 18 | | CMPD 19 | | CMPD 20 | | CMPD 21 | | CMPD 22 | |
|---|---|---|---|---|---|---|---|---|---|---|---|---|---|---|---|---|---|---|---|---|---|---|
| | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 |
| | | | | | | | | | | | | | | | | | | | | | | |
| | | | | | | | | | PRSOL | | | | | | | | | | | | | |
| COTTON | 8G | 7G | 1C | 3G | 3C,9H | 2C,4G | 2C,4G | 3C,6G | 0 | 0 | 2G | 0 | 0 | 0 | 4C,8H | 4C,9G | 2C,6G | 8H | 2C,3G | 4C,8H | 3C,7G | 3C,9H |
| MORNING GLORY | 0 | 0 | 1C | 2C,5H | 2C,4H | 3C,8H | 3C,8H | 9C | 0 | 0 | 2C,4G | 1C | 0 | 1C | 3C,8G | 6C,9G | 9G | 9G | 7H | 10C | 3C,8G | 10C |
| COCKLEBUR | 3G | 5G | 2H | 3C,8H | 3C,9H | 3C,9H | 2C,8H | 5C,9G | 0 | 0 | 1C | 0 | 0 | 0 | 3C,9G | 5C,9G | 3C,7H | 2C | 10C | 4C,9G | 9C |
| NUTSEDGE | 9G | — | 10E | 10E | 0 | 0 | 2C,2G | 2C,7G | 0 | 0 | 0 | 0 | 0 | 2G | 3G | 4G | 9G | 5G | 2C,5G | 0 | 4C,9G | 9C |
| CRABGRASS | 2G | 4G | 10E | — | 0 | 0 | 0 | 0 | 0 | 0 | 0 | 2G | 0 | 0 | 2G | 9C | 4G | 10E | 6G | 9H | 0 | 2C,8G |
| BARNYARD GRASS | 3C,8H | 9H | 2C,7G | 3C,8H | 0 | 0 | 0 | 0 | 0 | 0 | 0 | 0 | 0 | 0 | 3C,8H | 0 | 5H | 6G | 0 | 5G | 0 | 9C |
| WILD OATS | 5G | 2C,7G | 0 | 5G | 0 | 0 | 0 | 5C,9G | 0 | 0 | 0 | 0 | 0 | 0 | 2G | 9C | 6G | 9H | 6G | 9H | 3G | 3C,7G |
| WHEAT | 3C,8H | 3C,9H | 2H | 0 | 0 | 0 | 0 | 9C | 0 | 0 | 0 | 0 | 0 | 0 | 3C,8H | 0 | 2G | 5G | 0 | 2G | 0 | 0 |
| CORN | 3G | 2C,6G | 9H | 3G | 0 | 0 | 0 | 0 | 0 | 0 | 0 | 0 | 0 | 0 | 4G | 2C,7G | 3C,6H | 10C | 7G | 4G | 0 | 0 |
| SOYBEAN | 3C,7H | 3C,9H | 9H | 3G | 0 | 0 | 0 | 0 | 0 | 0 | 0 | 0 | 0 | 0 | 5G | 3C,9G | 10E | 9H | 2H | 9H | 0 | 0 |
| RICE | 10E | 10E | 10H | 10E | 0 | 0 | 0 | 0 | 3C,8H | 4C,9H | 0 | 2C,3G | 0 | 0 | 0 | 8G | 7H | 7H | 8H | 4C,9H | 0 | 0 |
| SORGHUM | 6C,9H | 6C,9H | 9G | 7C,9H | 0 | 0 | 0 | 9C | 9H | 9H | 4G | 0 | 0 | 0 | 8G | 0 | 9G | 5G | 5G | 5G | 0 | 0 |
| CHEATGRASS | 9G | 9G | 6G | 4C,8H | 0 | 2G | 0 | 9C | 2G | 5G | 3G | 0 | 0 | 0 | 5G | 8G | 7H | 9H | 5G | 0 | 0 | 0 |
| SUGAR BEETS | 9G | 5C,9G | 6H | 0 | 0 | 0 | 0 | 9C | 5G | 5G | 2G | 0 | 0 | 0 | 3G | 3G | 9G | 9G | 4G | 0 | 0 | 0 |
| VELVETLEAF | 4G | 3C,8G | 5H | 2G | 0 | 0 | 0 | 0 | 2G | 3C,8G | 0 | 0 | 0 | 0 | 4G | 9H | 4G | 3C,8H | 5G | 5G | 0 | 0 |
| GIANT FOXTAIL | 2C,8G | 0 | 3C,6G | 3C,5G | 0 | 0 | 0 | 0 | 2C,9G | 2C,7G | 0 | 0 | 0 | 0 | 5G | 2C,7G | 9H | 3C,5H | 5G | 2G | 0 | 0 |
| BARLEY | 7G | 0 | 0 | 7G | 0 | 0 | 0 | 0 | 2C,2G | 8G | 0 | 0 | 0 | 0 | 5G | 3C,9G | 8G | 9G | 7G | 0 | 0 | 0 |
| DOWNY BROME | | | | | | | | | | | | | | | | | | | | | | |

| RATE = KG/HA | CMPD 12 | | CMPD 13 | | CMPD 14 | | CMPD 15 | | CMPD 16 | | CMPD 17 | | CMPD 18 | | CMPD 19 | | CMPD 20 | | CMPD 21 | | CMPD 22 | |
|---|---|---|---|---|---|---|---|---|---|---|---|---|---|---|---|---|---|---|---|---|---|---|
| | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 |
| | | | | | | | | | POSOL | | | | | | | | | | | | | |
| COTTON | 0 | 0 | | | | | | | 0 | 0 | | | | | 4C,8H | 4C,9G | 0 | 0 | 4C,8H | 3C,7G | 3C,9H |
| MORNING GLORY | 0 | 0 | | | | | | | 0 | 0 | | | | | 3C,8G | 6C,9G | 0 | 0 | 10C | 3C,8G | 10C |
| COCKLEBUR | 3G | 3G | | | | | | | 0 | 0 | | | | | 3C,9G | 3C,9G | 0 | 0 | 10C | 4C,9G | 9C |
| NUTSEDGE | 4G | 4G | | | | | | | 0 | 0 | | | | | 3G | 4G | 0 | 0 | 0 | 4C,9G | 9C |
| CRABGRASS | 0 | 0 | | | | | | | 0 | 0 | | | | | 2G | 9C | 0 | 0 | 9H | 0 | 2C,8G |
| BARNYARD GRASS | 0 | 0 | | | | | | | 0 | 0 | | | | | 3C,8H | 0 | 0 | 0 | 5G | 0 | 9C |
| WILD OATS | 0 | 0 | | | | | | | 0 | 0 | | | | | 2G | 2C,7G | 0 | 0 | 9H | 3G | 3C,7G |
| WHEAT | 0 | 0 | | | | | | | 0 | 0 | | | | | 3C,8H | 0 | 0 | 0 | 2G | 0 | 0 |

TABLE A-continued

| | | | | | | | | | | | | | | | | | | | | | | |
|---|---|---|---|---|---|---|---|---|---|---|---|---|---|---|---|---|---|---|---|---|---|---|
| CORN | 0 | 0 | 0 | 0 | 0 | 0 | 2C | 2C,2G | 0 | 0 | 0 | 0 | 2C,4G | 3C,8H | 0 | 0 | 3C,9G | 5U,9C | 3C,7H |
| SOYBEAN | 0 | 0 | 4H | 2C,6H | 0 | 0 | 0 | 3C,9G | 0 | 0 | 0 | 0 | 2H | 3C,7H | 0 | 0 | 4C,9G | 0 | 0 |
| RICE | 0 | 0 | 0 | 0 | 0 | 0 | 3C,8H | 9C | 0 | 0 | 0 | 0 | 4G | 3C,9G | 0 | 0 | 2C,8G | 5C,9G | 2C,5G |
| SORGHUM | 0 | 0 | 0 | 0 | 0 | 0 | 4C,9G | 5C,9G | 0 | 0 | 0 | 0 | 9G | 9C | 0 | 0 | 3C,9H | 3C,9G | 3C,9G |
| CHEATGRASS | 0 | 0 | 0 | 0 | 0 | 0 | 9C | 9C | 0 | 0 | 0 | 0 | 5G | 2C,8G | 0 | 0 | | | |
| SUGAR BEETS | 0 | 0 | 3C,8H | 0 | 0 | 0 | 6G | 9C | 2C,8G | 0 | 0 | 0 | 9C | 5G | 0 | 0 | 9C | 10C | 3C,7H |
| VELVETLEAF | 0 | 0 | 5G | 3C,9H | 0 | 0 | 2C,6G | 9C | 5G | 0 | 0 | 0 | 3C,8G | 10C | 0 | 0 | 5C,9G | 10C | 2C,7G |
| GIANT FOXTAIL | 0 | 0 | 0 | 3C,9G | 0 | 0 | 3C,8G | 9C | 4G | 3G | 0 | 0 | 3C,7G | 4C,9H | 0 | 0 | 0 | 4C,9G | 0 |
| BARLEY | 0 | 0 | 0 | 0 | 0 | 0 | 3C,8G | 9C | 2G | 2G | 0 | 0 | 2C,5G | 3C,8G | 0 | 0 | 3G | 7G | 2G |
| DOWNY BROME | 0 | 0 | 0 | 0 | 0 | 0 | 2C,8G | 2C,9C | 3G | 0 | 0 | 0 | | | 0 | 0 | 9C | 9C | 3C,9G |
| | | | | | | | | | | | | | | | | | | | PRSOL | |
| COTTON | 0 | 0 | 0 | 0 | 0 | 0 | 0 | 0 | 0 | 0 | 0 | 0 | 0 | 1H | 0 | 0 | 2G | 7G | 4G |
| MORNING GLORY | 0 | — | 0 | 0 | 0 | 0 | 0 | 1C | 0 | 0 | 0 | 0 | 0 | 3G | 0 | 0 | 3C,4G | 9G | 0 |
| COCKLEBUR | 0 | 0 | 0 | 0 | 0 | 0 | 0 | 2G | 0 | 0 | 0 | 0 | 0 | 2C | 0 | 0 | 8H | 8H | 1C |
| NUTSEDGE | 0 | 0 | 0 | 0 | 0 | 0 | 0 | 10E | 0 | 0 | 0 | 0 | 0 | 10E | 0 | 0 | 10E | 10E | 5H |
| CRABGRASS | 0 | 0 | 0 | 0 | 0 | 0 | 0 | 3G | 0 | 0 | 0 | 0 | 4G | 7G | 0 | 0 | 0 | 0 | 9G |
| BARNYARD GRASS | 0 | 0 | 0 | 0 | 0 | 0 | 0 | 7H | 0 | 0 | 0 | 0 | 3G | 3C,5G | 0 | 0 | 7H | 8H | 0 |
| WILD OATS | 0 | 0 | 0 | 0 | 0 | 0 | 0 | 2C,3G | 0 | 0 | 0 | 0 | 0 | 5G | 0 | 0 | 2G | 2G | 8H |
| WHEAT | 0 | 0 | 0 | 0 | 0 | 0 | 0 | 6G | 0 | 0 | 0 | 0 | 0 | 3C,7G | 0 | 0 | 3G | 3G | 0 |
| CORN | 0 | 0 | 0 | 0 | 0 | 0 | 0 | 2C,4G | 0 | 0 | 0 | 0 | 2C,5G | 3C,7G | 0 | 0 | 8G | 9G | 2C,7G |
| SOYBEAN | 0 | — | 0 | 0 | 0 | 0 | 0 | 1C | 0 | 0 | 0 | 0 | 1C | 1H | 0 | 0 | 1C,1H | 3C,7G | 1C |
| RICE | 0 | 0 | 0 | 0 | 0 | 0 | 0 | 8H | 0 | 0 | 0 | 0 | 2G | 6G | 0 | 0 | 8H | 9H | 6G |
| SORGHUM | 0 | 0 | 0 | 0 | 0 | 0 | 0 | 2C,8H | 0 | 0 | 0 | 0 | 3C,3G | 10H | 0 | 0 | 7H | 9H | 8G |
| CHEATGRASS | 0 | 0 | 3H | 0 | 0 | 0 | 0 | 4G | 0 | 0 | 0 | 0 | 0 | 4G | 0 | 0 | | | |
| SUGAR BEETS | 0 | 0 | 0 | 0 | 0 | 0 | 0 | 2G | 0 | 0 | 0 | 0 | 4H | 6G | 0 | 0 | 2H | 4H | 8G |
| VELVETLEAF | 0 | 0 | 0 | 0 | 0 | 0 | 0 | 6G | 0 | 0 | 0 | 0 | 0 | 1H | 0 | 0 | 5H | 0 | 3H |
| GIANT FOXTAIL | 0 | 0 | 0 | 0 | 0 | 0 | 0 | 0 | 0 | 3G | 0 | 0 | 4G | 2C,8G | 0 | 0 | 0 | 0 | 0 |
| BARLEY | 0 | 0 | 0 | 0 | 0 | 0 | 0 | 9H | 0 | 0 | 0 | 0 | 2G | 3C,7G | 0 | 0 | 2C,3G | 0 | 2C,5G |
| DOWNY BROME | 0 | 0 | 0 | 0 | 0 | 0 | 0 | 5G | 0 | 0 | 0 | 0 | 0 | 0 | 0 | 0 | 7G | 3G | 10C |

| | CMPD 23 | | CMPD 24 | | CMPD 25 | | CMPD 26 | | CMPD 27 | | CMPD 28 | | CMPD 29 | | CMPD 30 | |
|---|---|---|---|---|---|---|---|---|---|---|---|---|---|---|---|---|
| RATE = KG/HA | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 |
| | | | | | | | POSOL | | | | | | | | | |
| COTTON | 0 | 6G | 0 | 2C,2G | 9C | 10C | 9C | 9C | 9C | 9C | 6C,9G | 9C | 3C,8G | 9C | 4C,8G | 5C,9G |
| MORNING GLORY | 0 | 0 | 2H | 1C | 9C | 9C | 10C | 10C | 10C | 10C | 2C,6G | 4C,8H | 4C,9G | 10C | 4C,9H | 10C |
| COCKLEBUR | 7G | 3C,7G | 0 | 3C,8G | 10C | 10C | 10C | 10C | — | 10C | 10C | 10C | 5C,9G | 10C | 4C,9H | 10C |
| NUTSEDGE | 0 | 3G | 0 | 0 | 10C | 10C | 10C | 10C | 6G | 10C | 10C | 10C | 9C | 7G | 2G | 6G |
| CRABGRASS | 0 | 0 | 0 | 3C,9H | 2G | 3C,5G | 3C,9G | 3C,9G | 5C,9H | 7G | 2C,7G | 4C,9G | 5G | 2C,7G | 2G | 3C,8G |
| BARNYARD GRASS | 0 | 3C,3G | 3C,7G | 3C,9H | 9C | 9C | 3C,9G | 3C,9G | 7G | 9G | 9C | 3C,9G | 4C,8H | 9C | 4C,9G | 9C |
| WILD OATS | 0 | 3G | 2G | 3C,7G | 2C,7G | 5C,9G | 5C,9G | 5C,9G | 8G | 2C,7G | 9G | 3C,9G | 3C,9G | 7G | 6U,9G | 3C,9G |
| WHEAT | 0 | 3G | 2G | 3C,6G | 9G | 7U,9C | 5C,9G | 4C,9G | 2C,7H | 5C,9G | 5C,9G | 6C,9G | 5G | 9C | 6G | 4C,9G |
| CORN | 2C,6G | 3C,7G | 2C,7H | 5C,9G | 5U,9C | 9C | 9C | 9C | 3C,8H | 5C,9G | 9C | 6C,9G | 5C,9G | 4C,9G | 5C,9G | 6U,9G |
| SOYBEAN | 2H | 3C,7G | 0 | 2H | 9C | 9C | 6C,9G | 9C | 4C,9G | 6C,9G | 5C,9G | 6C,9G | 3C,8H | 5C,9G | 5C,9G | 6C,9G |
| RICE | 3G | 0 | 4C,9G | 5C,9G | 9C | 5C,9G | 5C,9G | 4C,9G | 9H | 4C,9G | 4C,9G | 6C,9G | 3C,9G | 4C,9G | 9G | 9C |
| SORGHUM | 0 | 2G | 3C,8G | 3C,9G | 9C | 9C | 10C | 5C,9G | 7G | 9C | 10C | 10C | 10C | 5C,9G | 4C,8H | 3C |
| CHEATGRASS | 0 | 3G | 0 | 4C,9H | 9C | 10C | 10C | 10C | 10C | 10C | 10C | 10C | 4C,9H | 10C | 5C,9H | 10C |
| SUGAR BEETS | 5G | 3C,8G | 3C,7G | 0 | 10C | 10C | 9G | 10C | 9G | 4C,9G | 10C | 10C | 9G | 9G | 4C,9G | 10C |
| VELVETLEAF | 4G | 4G | 2G | 3C,7G | 4C,9G | 10C | 2C,9G | 10C | 3C,8G | 9G | 3C,9G | 10C | 3C,6G | 4C,9G | 4G | 6G |
| GIANT FOXTAIL | 0 | 3G | 3G | 3G | 7G | 9C | 9G | 5C,9G | 5G | 9C | 3C,9G | 3C,9G | 3G | | | |
| BARLEY | 0 | 3G | 3G | 3G | 2C,9G | 2C,9G | 5C,9G | 5C,9G | 5G | | 3C,9G | 3C,9G | | | | |
| DOWNY BROME | 2G | 2C,5G | 2G | 2C,5G | | | | | | | | | | | | |
| | | | | | | | PRSOL | | | | | | | | | |

TABLE A-continued

| | | | | | | | | | | | | | | | | |
|---|---|---|---|---|---|---|---|---|---|---|---|---|---|---|---|---|
| COTTON | 0 | 0 | 0 | 0 | 8G | 9G | 9G | 9G | 9G | 5G | 2C,5G | 4C,8G | 2C,6G | 9G | | |
| MORNING GLORY | 0 | 0 | 0 | 0 | 9G | 9G | 9G | 9G | 8G | 2C,5G | 9G | 9G | 9G | 9G | | |
| COCKLEBUR | 0 | 3G | 2G | 9H | 9H | 9H | — | 8H | 9H | 3C,6H | 8H | 9H | 9H | | | |
| NUTSEDGE | 0 | 0 | 0 | 9G | 9H | 9H | 7G | 10E | 10E | 10C | 2G | 5G | 8H | 9H | | |
| CRABGRASS | 0 | 0 | 7G | 2G | 5G | 5C,9G | 4G | 9G | 3C,9H | 2G | 2C,4G | 4C,9G | 2C,5G | 7G | | |
| BARNYARD GRASS | 0 | 0 | 0 | 0 | 2G | 4H | 2C,7G | 2C,7H | 3C,8G | 3C,9H | 2G | 3C,9H | 3C,7H | 4C,9H | | |
| WILD OATS | 0 | 0 | 0 | 0 | 4H | 9H | 9H | 9H | 6G | 9H | 0 | 5G | 5G | 2G | | |
| WHEAT | 0 | 0 | 0 | 0 | 2G | 7G | 0 | 2G | 8G | 3C,8G | 3C,8H | 2C,6G | 7G | 4G | | |
| CORN | 0 | 2C,5G | 5G | 4C,9G | 3C,8G | 9G | 8G | 2C,8G | 3C,9H | 5C,9H | 4C,8H | 2C,9G | 3C,7H | 3C,7H | | |
| SOYBEAN | 0 | 0 | 0 | 3C,7G | 3C,9G | 3C,6G | 3C,8G | 9G | 3C,8G | 3C,8G | 3C,7H | 9H | 4C,8H | 2G | | |
| RICE | 0 | 0 | 7G | 3C,8G | 4C,8G | 4C,8H | 3C,7H | 2C,9H | 3C,7H | 3C,7H | 4C,8H | 10H | 4C,8H | 4G | | |
| SORGHUM | 0 | 0 | 7G | 3C,7G | 10E | 9H | 9H | 10H | 9H | 9H | 10E | 10H | 5C,8H | 3C,7H | | |
| CHEATGRASS | 0 | 0 | 0 | 7G | 4C,8G | 9H | 8G | 3C,8H | 4C,9H | 3C,6H | 9H | 3C,6H | 4C,8H | 5C,8H | | |
| SUGAR BEETS | 0 | 3G | 0 | 3G | 9G | 4C,8G | 7G | 4C,9G | 7G | 3C,9G | 2C,4G | 4C,9G | 5C,9G | 3C,8H | | |
| VELVETLEAF | 0 | 0 | 0 | 0 | 9G | 3C,9G | 9G | 3C,9G | 3C,7G | 4C,9G | 2G | 5C,9G | 4C,9G | 4C,9G | | |
| GIANT FOXTAIL | 0 | 0 | 0 | 5G | 2H | 9G | 8G | 9G | 8G | 9C | 0 | 9C | 3C,3G | 5C,9G | | |
| BARLEY | 0 | 0 | 0 | 7G | 2C,6G | 9G | 9H | 9H | 9H | 9H | 0 | 7G | 7G | 9H | | |
| DOWNY BROME | 0 | 0 | 0 | 5G | 2C,6G | 2C,9G | 8G | 8G | 9G | 9G | 5G | 2C,8G | 7G | 9G | | |

It is noted that a few compounds such as Compounds 4, 12, 13, 16, 18 and 20 show little or no herbicidal activity at the rate tested. It is thought that they would show more herbicidal activity at higher rates.

TEST B

Postemergence

Three round pans (25 cm diameter by 12.5 cm deep) were filled with Sassafras sandy loam soil. One pan was planted with nutsedge (*Cyperus rotundus*) tubers, crabgrass (*Digitaris sanguinalis*), sicklepod (*Cassia obtusifolia*), jimsonweed (*Datura stramonium*), velvetleaf (*Abutilon theophrasti*), lambsquarters (*Chenopodium album*), rice (*Oryza sativa*) and teaweed (*Sida spinosa*). The second pot was planted with green foxtail (*Setaria viridis*), cocklebur (*Xanthium pensylvanicum*), morningglory (*Ipomoea hederacea*), cotton (*Gossypium hirsutum*), johnsongrass (*Sorghum halepense*), barnyardgrass (*Echinochloa crusgalli*), corn (*Zea mays*), soybean (*Glycine max*) and giant foxtail (*Setaria faberi*). The third pot was planted with wheat (*Triticum aestivum*), barley (*Hordeum vulgare*), wild buckwheat (*Polgonum convolvulus* L.), cheatgrass (*Bromus secalinus* L.), sugarbeet (*Beta vulgaris*), wild oats (*Avena fatua*), viola (*Viola arvensis*), blackgrass (*Alopecurus myosuroides*), and rape (*Brassica napus*). The plants were grown for approximately fourteen days, then sprayed postemergence with the chemicals dissolved in a non-phytotoxic solvent.

Preemergence

Three round pans (25 cm diameter by 12.5 cm deep) were filled with Sassafras sandy loam soil. One pan was planted with nutsedge tubers, crabgrass, sicklepod, jimsonweed, velvetleaf, lambsquarters, rice and teaweed. The second pot was planted with green foxtail, cocklebur, morningglory, cotton, johnsongrass, barnyardgrass, corn, soybean and giant foxtail. The third pot was planted with wheat, barley, wild buckwheat, cheatgrass, sugarbeet, wild oat, viola, blackgrass and rape. The three pans were sprayed preemergence with the chemicals dissolved in a non-phytotoxic solvent.

Treated plants and controls were maintained in the greenhouse for 24 days, then all rated plants were compared to controls and visually rated for plant response.

Response ratings are based on a scale of 0 to 100 were 0=no effect and 100=complete control. A dash (—) response means no test.

Response ratings are contained in Table B.

TABLE B

| | CMPD 1 | | CMPD 2 | | | | CMPD 5 | | | | CMPD 9 | | | | CMPD 15 | |
|---|---|---|---|---|---|---|---|---|---|---|---|---|---|---|---|---|
| RATE = G/HA | 0016 | 0062 | 0001 | 0004 | 0016 | 0062 | 0001 | 0004 | 0016 | 0062 | 0001 | 0004 | 0016 | 0062 | 0016 | 0062 |
| | | | | | | PRE | | | | | | | | | | |
| VELVETLEAF | 50 | 60 | 0 | 30 | 50 | 70 | 0 | 30 | 30 | 40 | 30 | 60 | 90 | 95 | 0 | 20 |
| USH11 SUGARBEAT | 80 | 90 | 30 | 50 | 80 | 90 | 0 | 0 | 60 | 80 | 70 | 90 | 100 | 100 | 30 | 80 |
| LARGE CRABGRASS | 60 | 70 | 0 | 20 | 30 | 60 | 0 | 0 | 40 | 100 | 0 | 30 | 50 | 80 | 40 | 80 |
| PRICKLY SIDA | — | 90 | 30 | 50 | 70 | 90 | 0 | 0 | 30 | 30 | 0 | 30 | 50 | 70 | 30 | 50 |
| JIMSONWEED | 70 | 90 | 0 | 30 | 60 | 90 | 0 | 60 | 80 | 90 | 0 | 30 | 50 | 80 | 0 | — |
| RICE DRY SEEDED | 100 | 100 | 30 | 50 | 90 | 100 | 0 | 50 | 90 | 90 | 30 | 60 | 80 | 90 | 90 | 100 |
| COCKLEBUR | 30 | 50 | 0 | 0 | 30 | 40 | 0 | 30 | 50 | 60 | 0 | 30 | 60 | 90 | 0 | 40 |
| COKER COTTON | 50 | 90 | 0 | 0 | 0 | 20 | 0 | 0 | 40 | 70 | 0 | 30 | 50 | 60 | 0 | 10 |
| WILLMS SOYBEANS | 70 | 100 | 0 | 0 | 0 | 0 | 0 | 20 | 50 | 60 | 0 | 30 | 40 | 60 | 0 | 0 |
| BARNYARDGRASS | 100 | 100 | 0 | 30 | 50 | 70 | 0 | 20 | 80 | 80 | 30 | 50 | 80 | 100 | 20 | 40 |
| WILD OATS | 30 | 50 | 0 | 0 | 30 | 50 | 0 | 30 | 40 | 40 | 0 | 0 | 30 | 50 | 20 | 60 |
| IVY MORNINGGLORY | 70 | 90 | 0 | 20 | 30 | 50 | 0 | 0 | 30 | 60 | 0 | 30 | 50 | 80 | 20 | 40 |
| ERA WHEAT | 40 | 70 | 0 | 0 | 20 | 40 | 0 | 0 | 30 | 60 | 0 | 30 | 60 | 90 | 0 | 20 |
| SICKLEPOD | 60 | 80 | 0 | 20 | 30 | 50 | 0 | 0 | 40 | 80 | 30 | 50 | 70 | 90 | 0 | 20 |
| JOHNSONGRASS | 90 | 100 | 70 | 80 | 90 | 100 | 0 | 40 | 70 | 90 | 50 | 70 | 80 | 90 | 70 | 90 |
| PURPLE NUTSEDGE | 80 | 90 | 0 | 0 | 30 | 70 | 0 | 20 | 40 | 60 | 0 | 30 | 60 | 90 | 40 | 50 |
| G4646 CORN | 0 | 40 | 0 | 0 | 0 | 0 | 0 | 0 | 0 | 0 | 0 | 0 | 0 | 0 | 0 | 0 |
| WILD BUCKWHEAT | 80 | 80 | 0 | 30 | 50 | 70 | 0 | 0 | 50 | 90 | 0 | 30 | 60 | 90 | 30 | 60 |
| BLACKGRASS | 70 | 100 | 30 | 50 | 70 | 100 | 0 | 50 | 50 | 70 | 50 | 60 | 70 | 90 | 80 | 100 |
| ALTEX RAPE | 90 | 100 | 50 | 70 | 80 | 90 | 0 | 70 | 70 | 90 | 70 | 100 | 100 | 100 | 80 | 90 |
| KLAGES BARLEY | 40 | 70 | 0 | 20 | 40 | 60 | 0 | 20 | 30 | 80 | 30 | 50 | 70 | 90 | 50 | 80 |
| GREEN FOXTAIL | 90 | 100 | 0 | 0 | 30 | 60 | 0 | 70 | 100 | 100 | 50 | 70 | 90 | 100 | 40 | 90 |
| CHEAT GRASS | 70 | 90 | 0 | 30 | 50 | 70 | 0 | 30 | 50 | 80 | 50 | 70 | 80 | 90 | 70 | 100 |
| LAMBSQUARTER | 90 | 100 | 0 | 30 | 60 | 90 | 0 | 20 | 30 | 70 | 70 | 100 | 100 | 100 | 80 | 90 |
| CHICKWEED SPP. | 50 | 80 | | | | | 0 | 0 | 40 | 40 | 30 | 50 | 70 | 90 | 0 | 10 |
| GIANT FOXTAIL | | | 30 | 50 | 70 | 80 | 0 | 20 | 90 | 100 | 70 | 90 | 100 | 100 | 40 | 90 |
| FIELD VIOLET | | | 20 | 30 | 60 | 80 | | | | | | | | | | |

| | CMPD 1 | | CMPD 2 | | | | CMPD 5 | | | | CMPD 9 | | | | CMPD 15 | | | |
|---|---|---|---|---|---|---|---|---|---|---|---|---|---|---|---|---|---|---|
| RATE = G/HA | 0004 | 0016 | 0001 | 0004 | 0016 | 0062 | 0.25 | 0001 | 0004 | 0016 | 0001 | 0004 | 0016 | 0062 | 0001 | 0004 | 0016 | 0062 |
| | | | | | | | POST | | | | | | | | | | | |
| GIANT FOXTAIL | 90 | 90 | — | 0 | 20 | 60 | 0 | — | 40 | 100 | — | 50 | 90 | 100 | 0 | 20 | 40 | 90 |

TABLE B-continued

| | | | | | | | | | | | | | | | | | | | |
|---|---|---|---|---|---|---|---|---|---|---|---|---|---|---|---|---|---|---|---|
| VELVETLEAF | 70 | 70 | 0 | 0 | 20 | 70 | 0 | 0 | 20 | 60 | 30 | 80 | 90 | 100 | 0 | 30 | 70 | 90 |
| USH11 SUGARBEET | 100 | 100 | — | 30 | 80 | — | — | 20 | 30 | 60 | — | 100 | 100 | 100 | 40 | 70 | 80 | 90 |
| LARGE CRABGRASS | 0 | 60 | 0 | 0 | 0 | 20 | 0 | 0 | 40 | 80 | 0 | 0 | 50 | 60 | 0 | 0 | 0 | 0 |
| PRICKLY SIDA | 20 | 60 | 0 | 0 | 0 | 50 | 0 | 0 | 20 | 70 | 0 | 30 | 50 | 70 | 0 | 0 | 20 | 30 |
| JIMSONWEED | 50 | 50 | 60 | 80 | 90 | 100 | 0 | 30 | 50 | 60 | 0 | 0 | 20 | 40 | 0 | 0 | 20 | 40 |
| RICE DRY SEEDED | 60 | 100 | 0 | 0 | 60 | 80 | 0 | 0 | 50 | 90 | 50 | 90 | 100 | 100 | 0 | 30 | 70 | 100 |
| COCKLEBUR | 80 | 100 | 60 | 60 | 70 | 90 | 0 | 0 | 30 | 70 | 70 | 100 | 100 | 100 | 0 | 50 | 70 | 100 |
| COKER COTTON | 90 | 90 | — | 40 | 50 | 70 | 0 | 0 | 0 | 20 | 50 | 80 | 90 | 90 | 0 | 0 | 10 | 20 |
| WILLMS SOYBEANS | 70 | 100 | — | 0 | 10 | 50 | 30 | 40 | 90 | 90 | — | 80 | 100 | 100 | 0 | 40 | 50 | 90 |
| BARNYARD-GRASS | 60 | 90 | 30 | 40 | 60 | 70 | 30 | 40 | 90 | 100 | 30 | 40 | 80 | 100 | 30 | 60 | 90 | 100 |
| WILD OATS | 60 | 80 | 0 | 0 | 0 | — | — | 30 | 50 | 70 | — | 70 | 100 | 100 | 0 | 60 | 90 | 100 |
| IVY MORNIN-GLORY | 70 | 100 | 70 | 70 | 80 | 80 | 0 | 0 | 30 | 60 | 60 | 90 | 100 | 100 | 0 | 50 | 90 | 90 |
| ERA WHEAT | 90 | 90 | 0 | 0 | 10 | 40 | — | 40 | 50 | 60 | — | 70 | 100 | 100 | 0 | 40 | 80 | 100 |
| SICKLEPOD | 90 | 100 | 0 | 0 | 40 | 70 | 0 | 0 | 40 | 80 | 50 | 70 | 100 | 100 | — | 20 | — | 50 |
| JOHNSON-GRASS | 100 | 100 | 90 | 90 | 100 | 100 | 0 | 70 | 90 | 100 | 70 | 100 | 100 | 100 | 50 | 50 | 70 | 90 |
| PURPLE NUTSEDGE | 0 | 60 | 0 | 0 | 30 | 40 | 0 | 20 | 30 | 60 | 0 | 30 | 60 | 100 | 0 | 0 | 20 | 30 |
| G4646 CORN | 0 | 0 | 0 | 0 | 0 | 10 | — | 0 | 20 | 80 | — | 0 | 20 | 40 | 0 | 0 | 0 | 20 |
| WILD BUCK-WHEAT | 70 | 80 | 0 | 0 | 30 | 30 | — | 0 | — | 80 | — | 60 | 90 | 100 | 0 | 0 | 50 | 70 |
| BLACKGRASS | 90 | 90 | 50 | 50 | 70 | — | — | 0 | 70 | 80 | — | 90 | 100 | 100 | 50 | 70 | 90 | 90 |
| ALTEX RAPE | 100 | 100 | 100 | 100 | 100 | — | — | 30 | 90 | 100 | — | 100 | 100 | 100 | 70 | 100 | 100 | 100 |
| KLAGES BARLEY | 70 | 80 | 0 | 0 | 0 | 10 | — | 20 | 40 | 90 | — | 70 | 100 | 100 | 0 | 30 | 50 | 90 |
| GREEN FOXTAIL | 70 | 80 | — | 40 | 50 | 90 | 0 | 40 | 70 | 90 | 30 | 50 | 80 | 90 | 20 | 40 | 80 | 90 |
| CHEAT GRASS | 90 | 100 | 0 | 0 | 30 | — | — | 0 | 70 | 70 | — | 80 | 100 | 100 | 0 | 30 | 70 | 90 |
| LAMBS-QUARTER | 80 | 90 | — | 50 | 60 | 70 | 0 | 0 | 0 | 40 | 50 | 70 | 100 | 100 | 40 | 60 | 80 | 90 |
| CHICKWEED SPP. | 70 | 90 | | | | | — | 0 | 40 | 60 | — | 70 | 90 | 100 | 0 | 0 | 30 | 70 |
| FIELD VIOLET DISPOSITION | | | 0 | 0 | 0 | — | | | | | | | | | BR | GC | TM | AG |

TEST C

Postemergence

Six round pots (17 cm diameter by 15 cm deep) were used to grow plants to the treatment stage. Four were planted with seeds or tubers of four species each and another with soybeans using Sassafras sandy loam as the growing media. The sixth pot was planted to corn using a Tama silt loam. During spraying, the soil of this pot was temporarily covered with perlite then later removed so any effects noted would be from foliar uptake only. A separate pot of corn (25.5 cm diameter by 19.5 cm deep) grown in Sassafras sandy loam was also included to determine foliar/soil treatment effects on plant growth. Plants were grown 10 to 20 days and were in the 2 to 5 leaf stage when sprayed postemergence with compounds of the invention. Species included were as follows: Corn [maize[ (*Zea maize*), Soybeans (*Glycine max*), Green foxtail (*Setaria viridis*), Giant foxtail (*Setaria faberii*), Fall Panicum (*Panicum dichotomiflorum*), Crabgrass (*Digitaria sanquinalis*), Barnyardgrass (*Echinochloa crus galli*), Johnsongrass (*Sorghum halepense*), Sorghum (*Sorghum vulgare*), Nutsedge (*Cyperus rotundus*), Velvetleaf (*Abutilon theophrasti*), Cockle bur (*Xanthium pensylvanicum*), Smartweed (*Polygonum persicaria*, Lambsquarter (*Chenopodium album*), Pigweed (*Amaranthus retroflexus*), Morningglory (*Ipomoea hederacea*), Jimsonweed (*Datura stramonium*), Ragweed (*Ambrosia artemisiifolia*).

Preemergence

Plantings were made as above except all in Tama silt loam. Compounds were sprayed preemergence the day after planting then all pots were watered to simulate rainfall.

After treatment all plantings were maintained in a greenhouse about 20 days then visually rated for plant respone. Ratings are based on a scale of 0 to 100 (&0) where 0=no effect and 100 (&0)=complete control. Response ratings are shown in Table C.

TABLE C

| | CMPD 1 | | | | CMPD 5 | | | | |
|---|---|---|---|---|---|---|---|---|---|
| RATE GM/HA | 0016 | 0032 | 0064 | 0125 | 0016 | 0032 | 0064 | 0125 | 0250 |
| | | | | PRE | | | | | |
| SOIL TYPE | TAM | TAM | TAM | TAM | TAM | TAM | TAM | TAM | TAM |
| G4646 CORN | 0 | 0 | 0 | 0 | 0 | 0 | 0 | 0 | 0 |
| WILLMS SOYBEANS | 0 | 25 | 50 | 80 | 0 | 0 | 0 | 20 | 45 |
| GREEN FOXTAIL | 0 | 35 | 70 | 100 | 0 | 15 | 20 | 35 | 50 |
| GIANT FOXTAIL | 0 | 30 | 70 | 95 | 0 | 15 | 20 | 35 | 50 |
| FALL PANICUM | 20 | 45 | 85 | 95 | 0 | 0 | 0 | 0 | 15 |
| LARGE CRABGRASS | 0 | 20 | 40 | 70 | 0 | 0 | 0 | 0 | 15 |
| BARNYARDGRASS | 25 | 45 | 85 | 100 | 0 | 15 | 30 | 70 | 85 |

TABLE C-continued

| | | | | | | | | | | |
|---|---|---|---|---|---|---|---|---|---|---|
| JOHNSONGRASS | 50 | 65 | 100 | 100 | 0 | 20 | 45 | 55 | 75 | |
| G522 SORGHUM | 45 | 55 | 90 | 100 | 20 | 35 | 55 | 75 | 95 | |
| PURPLE NUTSEDGE | 0 | 25 | 65 | 80 | 0 | 0 | 0 | 0 | 0 | |
| VELVETLEAF | 0 | 0 | 0 | 30 | 0 | 0 | 20 | 30 | 40 | |
| COCKLEBUR | 0 | 0 | 0 | 20 | 0 | 10 | 20 | 35 | 50 | |
| LADY SMARTWEED | 30 | 60 | 95 | 100 | 15 | 35 | 50 | 60 | 75 | |
| LAMBSQUARTER | 20 | 40 | 90 | 100 | 0 | 0 | 0 | 15 | 25 | |
| REDROOT PIGWEED | 50 | 70 | 100 | 100 | 0 | 25 | 45 | 65 | 85 | |
| IVY MORNINGLORY | 0 | 0 | 0 | 25 | 0 | 0 | 0 | 0 | 0 | |
| JIMSONWEED | 0 | 0 | 0 | 35 | 0 | 0 | 0 | 15 | 20 | |

| | CMPD 1 | | | | | | | CMPD 5 | | | | | |
|---|---|---|---|---|---|---|---|---|---|---|---|---|---|
| RATE GM/HA | 0002 | 0004 | 0008 | 0016 | 0032 | 0064 | 0125 | 0002 | 0004 | 0008 | 0016 | 0032 | 0064 |
| | POST | | | | | | | | | | | | |
| SOIL TYPE | SAS | SAS | SAS | SAS | SAS | SAS | SAS | SAS | SAS | SAS | SAS | SAS | SAS |
| G4646 CORN | 0 | 0 | 0 | 0 | 20 | 35 | 60 | 0 | 20 | 50 | 60 | 80 | 90 |
| WILLMS SOYBEANS | 65 | 85 | 100 | 100 | 100 | 100 | 100 | 90 | 90 | 98 | 98 | 100 | 100 |
| GREEN FOXTAIL | 40 | 60 | 80 | 90 | 95 | 100 | 100 | 50 | 60 | 70 | 70 | 90 | 98 |
| GIANT FOXTAIL | 40 | 65 | 80 | 100 | 100 | 100 | 100 | 40 | 50 | 60 | 70 | 98 | 100 |
| FALL PANICUM | 0 | 40 | 80 | 95 | 100 | 100 | 100 | | | | | | |
| LARGE CRABGRASS | 0 | 0 | 0 | 25 | 40 | 50 | 80 | 0 | 0 | 0 | 20 | 40 | 50 |
| BARNYARDGRASS | 0 | 30 | 50 | 70 | 100 | 100 | 100 | 70 | 98 | 100 | 100 | 100 | 100 |
| JOHNSONGRASS | 80 | 95 | 100 | 100 | 100 | 100 | 100 | 60 | 98 | 100 | 100 | 100 | 100 |
| G522 SORGHUM | 85 | 95 | 100 | 100 | 100 | 100 | 100 | 80 | 90 | 98 | 100 | 100 | 100 |
| PURPLE NUTSEDGE | 0 | 35 | 60 | 90 | 100 | 100 | 100 | 0 | 0 | 0 | 0 | 30 | 70 |
| VELVETLEAF | 0 | 25 | 40 | 65 | 85 | 95 | 100 | 0 | 0 | 30 | 50 | 60 | 90 |
| COCKLEBUR | 35 | 60 | 90 | 100 | 100 | 100 | 100 | 30 | 70 | 80 | 90 | 100 | 100 |
| LADY SMARTWEED | 25 | 40 | 50 | 60 | 70 | 85 | 95 | 20 | 30 | 30 | 50 | 70 | 98 |
| LAMBSQUARTER | 40 | 65 | 85 | 95 | 100 | 100 | 100 | 0 | 0 | 30 | 30 | 30 | 30 |
| REDROOT PIGWEED | 75 | 95 | 100 | 100 | 100 | 100 | 100 | 0 | 0 | 40 | 40 | 80 | 90 |
| IVY MORNINGLORY | 0 | 30 | 55 | 70 | 85 | 95 | 100 | 0 | 30 | 30 | 30 | 40 | 50 |
| JIMSONWEED | 0 | 0 | 20 | 40 | 60 | 70 | 85 | 40 | 60 | 60 | 60 | 100 | 100 |
| PERLITE CORN | 0 | 0 | 0 | 0 | 0 | 20 | 40 | 20 | 20 | 30 | 60 | 60 | 90 |

| | CMPD 9 | | | | |
|---|---|---|---|---|---|
| RATE GM/HA | 0016 | 0032 | 0064 | 0125 | 0250 |
| | PRE | | | | |
| SOIL TYPE | TAM | TAM | TAM | TAM | TAM |
| G4646 CORN | 0 | 0 | 0 | 0 | 20 |
| WILLMS SOYBEANS | 0 | 25 | 40 | 70 | 80 |
| GREEN FOXTAIL | 25 | 45 | 85 | 95 | 100 |
| GIANT FOXTAIL | 0 | 35 | 70 | 95 | 100 |
| FALL PANICUM | 40 | 85 | 100 | 100 | 100 |
| LARGE CRABGRASS | 0 | 20 | 35 | 50 | 65 |
| BARNYARDGRASS | 35 | 60 | 100 | 100 | 100 |
| JOHNSONGRASS | 70 | 90 | 100 | 100 | 100 |
| G522 SORGHUM | 75 | 95 | 100 | 100 | 100 |
| PURPLE NUTSEDGE | 30 | 50 | 70 | 90 | 100 |
| VELVETLEAF | 0 | 0 | 0 | 0 | 25 |
| COCKLEBUR | 0 | 0 | 20 | 35 | 50 |
| LADY SMARTWEED | 40 | 70 | 95 | 100 | 100 |
| LAMBSQUARTER | 25 | 40 | 65 | 95 | 100 |
| REDROOT PIGWEED | 30 | 65 | 90 | 100 | 100 |
| IVY MORNINGLORY | 0 | 0 | 0 | 0 | 35 |
| JIMSONWEED | 0 | 0 | 30 | 45 | 70 |

| | CMPD 9 | | | | | | |
|---|---|---|---|---|---|---|---|
| RATE GM/HA | 0002 | 0004 | 0008 | 0016 | 0032 | 0064 | 0125 |
| | POST | | | | | | |
| SOIL TYPE | SAS | SAS | SAS | SAS | SAS | SAS | SAS |
| G646 CORN | 0 | 0 | 0 | 0 | 0 | 0 | 30 |
| WILLMS SOYBEANS | 65 | 75 | 90 | 100 | 100 | 100 | 100 |
| GREEN FOXTAIL | 50 | 65 | 80 | 95 | 100 | 100 | 100 |
| GIANT FOXTAIL | 45 | 60 | 80 | 90 | 95 | 100 | 100 |
| FALL PANICUM | 50 | 65 | 80 | 95 | 95 | 100 | 100 |
| LARGE CRABGRASS | 0 | 0 | 0 | 30 | 40 | 50 | 80 |
| BARNYARDGRASS | 50 | 60 | 70 | 80 | 100 | 100 | 100 |
| JOHNSONGRASS | 95 | 100 | 100 | 100 | 100 | 100 | 100 |
| G522 SORGHUM | 100 | 100 | 100 | 100 | 100 | 100 | 100 |
| PURPLE NUTSEDGE | 0 | 20 | 40 | 65 | 85 | 90 | 95 |
| VELVETLEAF | 0 | 40 | 70 | 80 | 90 | 100 | 100 |
| COCKLEBUR | 45 | 95 | 100 | 100 | 100 | 100 | 100 |
| LADY SMARTWEED | 0 | 20 | 45 | 60 | 70 | 95 | 100 |
| LAMBSQUARTERS | 30 | 40 | 60 | 80 | 90 | 100 | 100 |
| REDROOT PIGWEED | 65 | 90 | 100 | 100 | 100 | 100 | 100 |
| IVY MORNINGLORY | 30 | 70 | 85 | 100 | 100 | 100 | 100 |
| JIMSONWEED | 0 | 0 | 0 | 0 | 25 | 45 | 70 |
| PERLITE CORN | 0 | 0 | 0 | 0 | 0 | 0 | 20 |

What is claimed is:

1. A 3-pyridinesulfonamide, represented by the formula
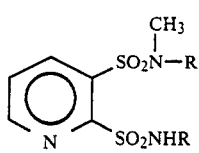
wherein
R is H or $C(CH_3)_3$.
2. The compound of claim 1 which is N3-methyl-2-3-pyridinedisulfonamide.
* * * * *